US012718567B2

(12) United States Patent
Wang et al.

(10) Patent No.: US 12,718,567 B2
(45) Date of Patent: Aug. 25, 2026

(54) SYSTEMS AND METHODS FOR SURGICAL DATA CENSORSHIP

(71) Applicant: Intuitive Surgical Operations, Inc., Sunnyvale, CA (US)

(72) Inventors: Ziheng Wang, Sandy Springs, GA (US); Kiran Bhattacharyya, Atlanta, GA (US); Samuel Bretz, Atlanta, GA (US); Anthony Jarc, Johns Creek, GA (US); Xi Liu, Peachtree Corners, GA (US); Andrea Villa, Ben Lomond, CA (US); Aneeq Zia, Atlanta, GA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 427 days.

(21) Appl. No.: 18/035,078

(22) PCT Filed: Nov. 18, 2021

(86) PCT No.: PCT/US2021/059952
§ 371 (c)(1),
(2) Date: May 2, 2023

(87) PCT Pub. No.: WO2022/109176
PCT Pub. Date: May 27, 2022

(65) Prior Publication Data

US 2023/0316756 A1 Oct. 5, 2023

Related U.S. Application Data

(60) Provisional application No. 63/116,906, filed on Nov. 22, 2020.

(51) Int. Cl.
*G06V 10/764* (2022.01)
*G06V 10/766* (2022.01)
(Continued)

(52) U.S. Cl.
CPC .......... *G06V 20/50* (2022.01); *G06V 10/7715* (2022.01); *G06V 10/809* (2022.01);
(Continued)

(58) Field of Classification Search
CPC .. G06V 20/50; G06V 10/7715; G06V 10/809; G06V 10/82; G06V 20/41;
(Continued)

(56) References Cited

U.S. PATENT DOCUMENTS 9,283,675 B2 3/2016 Hager et al.
10,799,090 B1 * 10/2020 Venkataraman ..... A61B 1/0655
(Continued)

OTHER PUBLICATIONS

Viola, Robust Real-Time Face Detection, International Journal of Computer Vision 57(2), 137-154, 2004 (Year: 2004).*
(Continued)

*Primary Examiner* — Vu Le
*Assistant Examiner* — Lei Zhao
(74) *Attorney, Agent, or Firm* — Foley & Lardner LLP

(57) ABSTRACT

Various of the disclosed embodiments relate to systems and methods for processing surgical data to facilitate further downstream operations. For example, some embodiments may include machine learning systems trained to recognize whether video from surgical visualization tools, such as endoscopes, depicts a field of view inside or outside the patient body. The system may excise or whiteout frames of video appearing outside the patient so as to remove potentially compromising personal information, such as the identities of members of the surgical team, the patients identity, configurations of the surgical theater, etc. Appropriate removal of such non-surgical data may facilitate downstream processing, e.g., by complying with regulatory requirements as well as by removing extraneous data poten-
(Continued)

tially inimical to further downstream processing, such as training a downstream classifier.

23 Claims, 19 Drawing Sheets

(51) Int. Cl.
*G06V 10/77* (2022.01)
*G06V 10/776* (2022.01)
*G06V 10/80* (2022.01)
*G06V 10/82* (2022.01)
*G06V 20/40* (2022.01)
*G06V 20/50* (2022.01)
*G16H 30/40* (2018.01)

(52) U.S. Cl.
CPC .............. *G06V 10/82* (2022.01); *G06V 20/41* (2022.01); *G06V 20/46* (2022.01); *G06V 2201/034* (2022.01); *G16H 30/40* (2018.01)

(58) Field of Classification Search
CPC ............. G06V 20/46; G06V 2201/034; G06V 10/764; G06V 10/766; G06V 10/776; G06V 2201/03; G06V 20/36; G06V 20/35; G16H 30/40
See application file for complete search history.

(56) References Cited

U.S. PATENT DOCUMENTS

2011/0026840 A1* 2/2011 Tao ........................ G06V 20/35 382/224
2020/0154080 A1 5/2020 Miller et al.
2020/0372180 A1* 11/2020 Venkataraman .... H04L 63/0407

OTHER PUBLICATIONS

Louizos, Multiplicative Normalizing Flows for Variational Bayesian Neural Networks, Proceedings of the 34th International Conference on Machine Learning, Sydney, Australia, PMLR 70, 2017 (Year: 2017).*
"Advantech—Enabling an Intelligent Planet—Accelerating the Intelligent Video Infrastructure" webpage, as of Oct. 20, 2020. Retrieved from Internet Archive Wayback Machine [URL: https://web.archive.org/web/20201020234151/https://www.advantech.com/solutions/video-solution?utm_source=CorpSiteHomepage-InPage&utm_medium=link&utm_campaign=CorpSiteHomepage-SolutionsClicks] on Jul. 6, 2023, 02 pages.
Brynolfsson, P., et al., "Haralick Texture Features from Apparent Diffusion Coefficient (ADC) MRI Images Depend on Imaging and Pre-processing Parameters," Scientific Reports, Jun. 2017, vol. 7(1): 4041. Retrieved from [URL: https://www.nature.com/articles/s41598-017-04151-4.pdf] on Jul. 6, 2023, 11 pages.
"Caffe", framework webpage [URL: https://caffe.berkeleyvision.org/] as of Nov. 18, 2020. Retrieved from Internet Archive Wayback Machine [URL: https://web.archive.org/web/20201118052534/ http://caffe.berkeleyvision.org/] on May 9, 2023, 02 pages.
Carreira, J., et al., "Quo Vadis, Action Recognition? A New Model and the Kinetics Dataset," Computer Vision and Pattern Recognition, 2017, pp. 6299-6308. Retrieved from [URL: https://openaccess.thecvf.com/content_cvpr_2017/papers/Carreira_Quo_Vadis_Action_CVPR_2017_paper.pdf] on Jul. 6, 2023, 10 pages.
Castellano, G., et al., "Texture Analysis of Medical Images," indicated as corresponding to Clinical Radiology, Dec. 2004, vol. 59 (12), pp. 1061-1069. Retrieved from [URL: http://facweb.cs.depaul.edu/research/vc/medix/2011/papers/Source2.pdf] on Jul. 6, 2023, 09 pages.
Chawla, N.V., et al. "SMOTE: Synthetic Minority Over-sampling Technique." arXiv preprint arXiv:1106.1813 (2011), though indicated as appearing earlier in Journal of Artificial Intelligence Research. 2002, pp. 321-357. Retrieved from [URL: https://arxiv.org/pdf/1106.1813.pdf] on Jul. 6, 2023, 37 pages.
"Scikit-learn Machine Learning in Python" toolset webpage [URL: https://scikit-learn.org/stable/] as of Nov. 19, 2020. Retrieved from Internet Archive Wayback Machine [URL: https://web.archive.org/web/20201119151816/https://scikit-learn.org/stable/] on May 10, 2023, 01 page.
"DMLC Decord v0.4.2" GitHub Repository Webpage, indicated as published Nov. 13, 2020. Retrieved from [URL: https://github.com/dmlc/decord/tree/v0.4.2] on May 9, 2023, 03 pages.
"Entropy (information theory)—Wikipedia" webpage, indicales last edit as Feb. 6, 2022, as received with the International Search Report for PCT/US2021/05992 as reference XP55889861AI, which indicated as retrieved from the Internet: [URL: https://en.wikipedia.org/wiki/Entropy_(information_theory)#Use_in_machine_ learning] on Feb. 9, 2022. 01 page.
Flouty, E., et al., "FaceOff: Anonymizing Videos in the Operating Rooms." arXiv preprint arXiv:1808.04440 (2018). Retrieved from [URL: https://arxiv.org/pdf/1808.04440] on Jul. 6, 2023, 08 pages.
Haralick, R.M., et al., "Textural Features for Image Classification," 1973, indicated as reprinted from IEEE Transactions on Systems, Man, and Cybernetics, Nov. 1973, vol. 3(6), pp. 610-621. Retrieved from [URL: http://haralick.org/journals/TexturalFeatures.pdf] on Jul. 6, 2023, 12 pages.
He, K., et al. "Identity Mappings in Deep Residual Networks." Sep. 2016, In European Conference on Computer Vision (pp. 630-645). Springer. Retrieved from [URL: https://link.springer.com/content/pdf/10.1007/978-3-319-46493-0_38.pdf?pdf=inline%20link] on Jul. 21, 2023, 16 pages.
Hu, M-K., "Visual Pattern Recognition by Moment Invariants," indicated as appearing in IRE Transactions on Information Theory, 1962, vol. 8(2), pp. 179-187. Retrieved from [URL: https://www.cs.utexas.edu/~grauman/courses/spring2011/psets/pset5/huMoments.pdf] on Jul. 6, 2023, 09 pages.
"Imbalanced-learn v0.7.0" package repository webpage, Jun. 9, 2020. Retrieved from [URL: https://pypi.org/project/imbalanced-learn/0.7.0/] on May 9, 2023, 03 pages.
International Preliminary Report on Patentability for Application No. PCT/US2021/059952, mailed Jun. 1, 2023, 10 pages.
International Search Report and Written Opinion for Application No. PCT/US2021/059952, mailed Mar. 4, 2022, 13 pages.
Issenhuth, T., et al. "Face detection in the operating room: Comparison of state-of-the-art methods and a self-supervised approach," International journal of computer assisted radiology and surgery 14 (2019): 1049-1058. Retrieved from an account with "Reprints Desk" [URL: https://www.researchsolutions.com/] in Jul. 2023, 10 pages.
Jia, Y., et al. "Caffe: Convolutional Architecture for Fast Feature Embedding." arXiv preprint arXiv:1408.5093 (2014) Retrieved from [URL: https://arxiv.org/pdf/1408.5093] on Jul. 6, 2023, 04 pages.
"Keras" Application Programming Interface webpage [URL: https://keras.io/], as of Nov. 19, 2020. Retrieved from Internet Archive Wayback Machine [URL: http://web.archive.org/web/20201119075317/https://keras.io/] on May 9, 2023, 02 pages.
Lemaitre, G., et al., "Imbalanced-learn: A Python Toolbox to Tackle the Curse of Imbalanced Datasets in Machine Leaming," Journal of Machine Learning Research, 2017, vol. 18, pp. 1-5. Retrieved from [URL: https://www.jmir.org/papers/volume18/16-365/16-365.pdf] on Jul. 6, 2023, 5 pages.
Li, J., et al., "A Comprehensive Review of Current Local Features for Computer Vision," indicated as appearing in Neurocomputing, Jun. 2008, vol. 71(10-12), pp. 1771-1787. Retrieved from [URL: https://www.labxing.com/files/iab_publications/4969-1556263566-uDiYlzJz.pdf] on Jul. 6, 2023, 17 pages.
"LIBSVM—A Library for Support Vector Machines" library webpage [URL: https://www.csie.ntu.edu.tw/~cjlin/libsvm/], as of Nov. 9, 2020. Retrieved from Internet Archive Wayback Machine [URL: https://web.archive.org/web/20201109215549/https://www.csie.ntu.edu.tw/~cjlin/libsvm/] on May 9, 2023, 02 pages.

(56) References Cited

OTHER PUBLICATIONS

Maier-Hein L., et al., "Surgical data science: enabling next-generation surgery." arXiv preprint arXiv:1701.06482 (2017). Retrieved from [URL: https://arxiv.org/pdf/1701.06482] on Jul. 6, 2023, 10 pages.

Munzer, B., et al., "Content-based Processing and Analysis of Endoscopic Images and Videos: A Survey," Multimedia Tools and Applications, 2018, vol. 77(1), pp. 1323-1362. Retrieved from [URL: https://link.springer.com/content/pdf/10.1007/s11042-016-4219-z.pdf?pdf=button] on Jul. 6, 2023, 40 pages.

Munzer, B., et al., "Relevance Segmentation of Laparoscopic Videos," IEEE International Symposium on Multimedia, 2013, pp. 84-91. Retrieved from an account with "Reprints Desk" [URL: https://www.researchsolutions.com/] in Jul. 2023, 8 pages.

"Read the Docs imblearn.over_sampling.SMOTE" API webpage, [URL: https://imbalanced-learn.readthedocs.lo/en/stable/generated/imblearn.over_sampling.SMOTE.html] as of Nov. 11, 2020. Retrieved from Internet Archive Wayback Machine [URL: http:/web.archive.org/web/20201111235644/https://imbalanced-learn.readthedocs.io/en/stable/generated/imblearn.over_sampling.SMOTE.html] on May 9, 2023. 03 pages.

Sandler, M., et al., "MobileNetV2: Inverted Residuals and Linear Bottlenecks." arXiv preprint arXiv:1801.04381 (2019). Retrieved from [URL: https://arxiv.org/pdf/1801.04381] on Jul. 6, 2023, 14 pages.

Simonyan, K., et al., "Very deep convolutional networks for large-scale image recognition." arXiv preprint arXiv:1409.1556 (2015). Indicated as being published as a conference paper at ICLR, 2015. Retrieved from [URL: https://arxiv.org/pdf/1409.1556.pdf] on Jul. 6, 2023, 14 pages.

Stanek, S.R., et al., "Automatic Real-time Detection of Endoscopic Procedures Using Temporal Features," Computer Methods and Programs in Biomedicine, Nov. 2012, vol. 108(2), pp. 524.535. Retrieved from an account with "Reprints Desk" [URL: https://www.researchhsolutions.com/] in Jul. 2023, 12 pages.

Tao, L., et al., "Surgical Gesture Segmentation and Recognition," Medical Image Computing and Computer-assisted Intervention, 2013, vol. 16 (Part III), pp. 339-346. Retrieved from [URL: https://link.springer.com/content/pdf/10.1007/978-3-642-40760-4_43.pdf?pdf-inline%20link] on Jul. 6, 2023, 08 pages.

"Tensorflow" platform webpage [URL: https://www.tensorflow.org/] as of Nov. 18, 2020. Retrieved from Internet Archive Wayback Machine [URL: https://web.archive.org/web/20201118224711/https://www.tensorflow.org/] on May 9, 2023, 03 pages.

"Torch, A Scientific Computing Framework for LUAJIT" framework webpage [URL: http://torch.ch/] as of Nov. 18, 2020. Retrieved from Internet Archive Wayback Machine [URL: https://web.archive.org/web/20201118030716/ http://torch.ch/] on May 9, 2023, 01 page.

Twinanda, A., "EndoNet: A Deep Architecture for Recognition Tasks on Laparoscopic Videos," in IEEE Transactions on Medical Imaging, vol. 36, No. 1, pp. 86-97. Jan. 2017. Retrieved from an account with "Reprints Desk" [URL: https://www.researchsolutions.com/] in Jul. 2023, 12 pages.

Vedula, S.S., et al., "Objective Assessment of Surgical Technical Skill and Competency in the Operating Room," Annual Review of Biomedical Engineering, Jun. 2017, vol. 19, pp. 301-325. Retrieved from [URL: https://www.ncbi.nlm.nih.gov/pmc/articles/PMC5555216/pdf/nihms889635.pdf] on Jul. 6, 2023. 31 Pages.

Vedula, S.S., et al., "Surgical Data Science: the New Knowledge Domain," Innovative Surgical Sciences, Apr. 2017, vol. 2(3), pp. 109-121. Retrieved from https://www.ncbi.nim.nih.gov/pmc/articles/PMC5602563/pdf/iss-2-20170004.pdf on Jul. 6, 2023, 21 pages.

"VEGA-6301 Datasheet" [online], indicated as last updated Jan. 10, 2017. Retrieved from [URL: https://advdownload.advantech.com/productfile/PIS/VEGA- 6301/Product%20-%20Datasheet/VEGA-6301_OS(Oct. 1, 2017) 20170116092830.pdf] on Jul. 6, 2023, 02 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Wang, Z., et al., "Automated Video Scrubbing When Endoscopes Are Out of Body during Minimally Invasive Surgery," submitted Feb. 7, 2020 to the 2020 International Symposium on Medical Robotics (ISMR2020), 01 page.

Zia, A., et al. "Surgical activity recognition in robot-assisted radical prostatectomy using deep learning." Medical Image Computing and Computer Assisted Intervention—MICCAI 2018: 21st International Conference, Granada, Spain, Sep. 16-20, 2018, Proceedings, Part IV 11. Springer International Publishing, 2018. Retrieved from an account with "Reprints Desk" [URL: https://www.researchsolutions.com/] in Jul. 2023, 08 pages.

Zohar, M., et al., "Accurate Detection of Out of Body Segments in Surgical Video using Semi-Supervised Learning." Proceedings of Machine Learning Research, Jul. 2020, vol. 121, pp. 923-936 ("Jul. 6-8, 2020" conference date identified at [URL: https://proceedings.mir.press/v121/] retrieved Jul. 6, 2023). Retrieved from [URL: http://proceedings.mir.press//121/zohar20a/zohar20a.pdf] on Jul. 6, 2023, 14 pages.

* cited by examiner

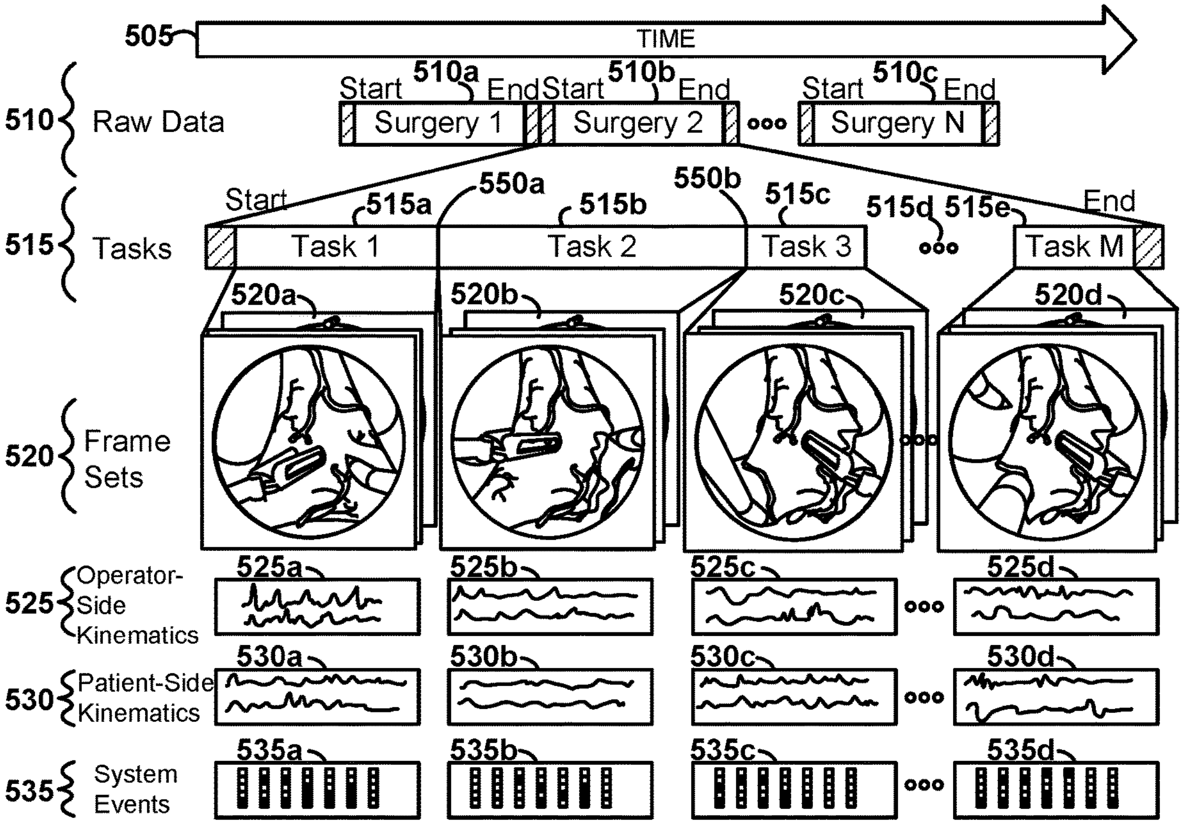

FIG. 5A

| Task name | Description | Start point | End point |
|---|---|---|---|
| Mobilize Colon | Exposing the prostate in the retropubic space by mobilizing the colon | First tool interaction with colon or surrounding tissue | Last tool interaction with colon or surrounding tissue |
| Endopelvic Fascia Dissection | Separation of the lateral edges of prostate from the endopelvic fascia (blunt sweeping motions) and exposing apex | First tool-tissue interaction that is directed at the endopelvic fascia (EPF) | Last tissue interaction with the EPF after the prostate is defatted and separated from EPF |
| Apical Dissection | Dissection of the apex of the prostate ultimately results in freed specimen | First tool-tissue interaction, often to orient the prostate for apical dissection | Prostate has been freed from all attachments |

ooo

FIG. 5B

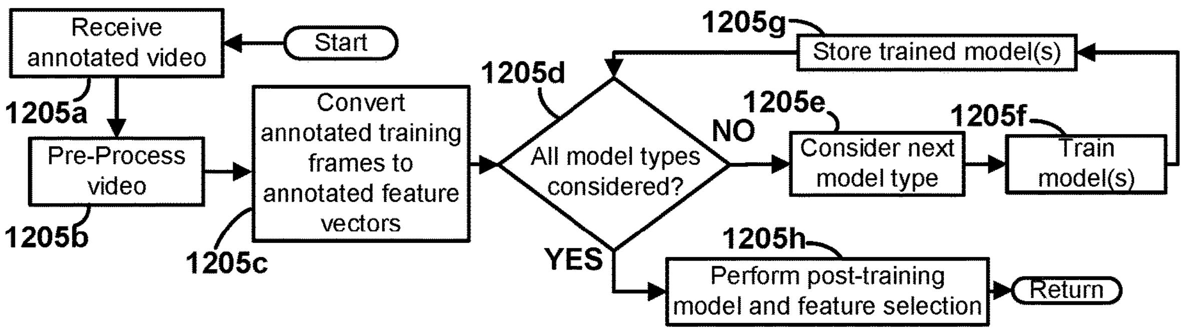

*FIG. 12A*

1210k
Select highest performing model
Start
1210a
All feature types for model considered?
YES
Return
NO
1210b
Consider training feature vectors of next feature type
1210c
Select fold allocations in training data
1210i
Save validation results
1210d
YES
All folds of training performed?
NO
1210h
Save trained model
1210l
Data in training fold balanced?
YES
1210g
Evaluate model
NO
1210e
Oversample unbalanced data in training fold(s)
Train model
1210f

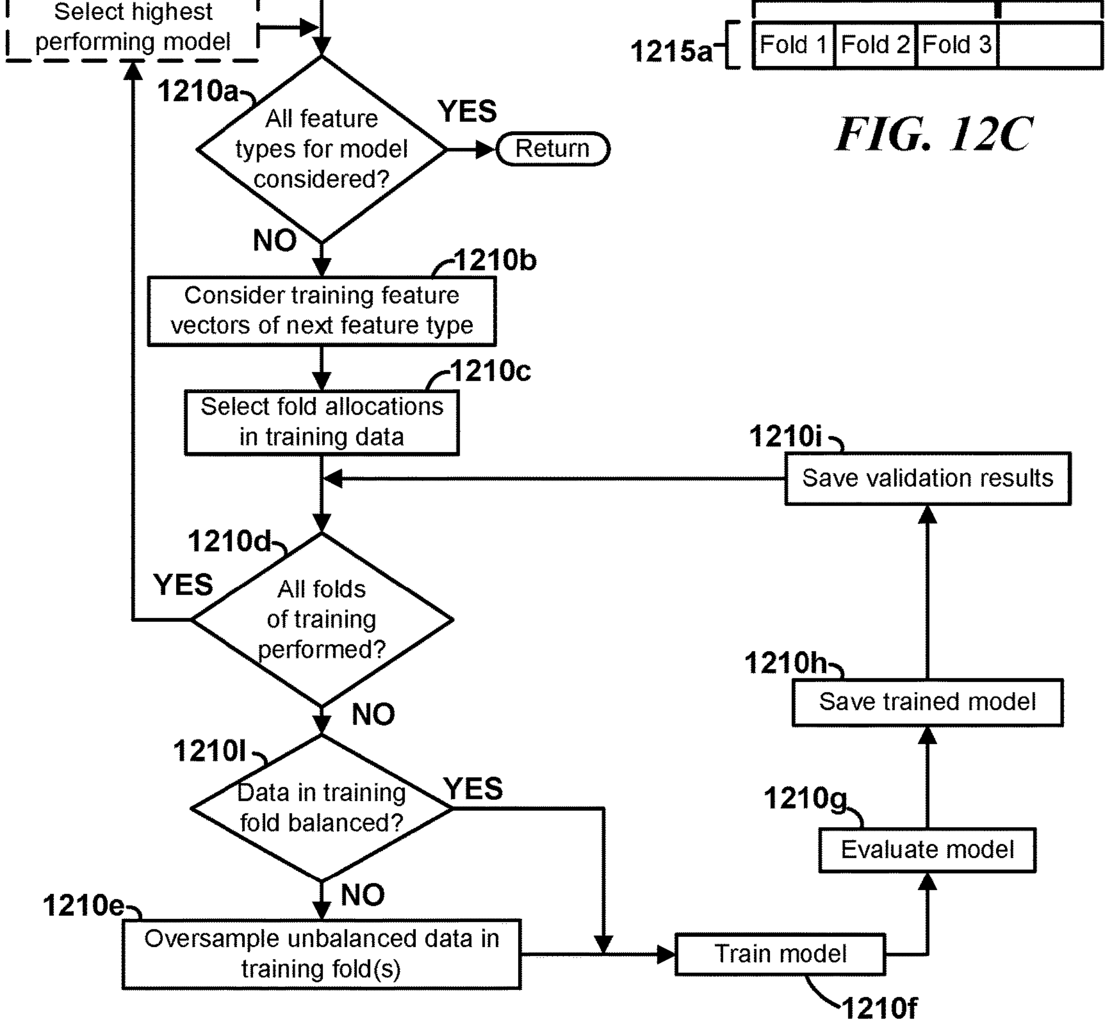

*FIG. 12B*

1215b
Training Portion
1215c
Test Portion
1215a
Fold 1 Fold 2 Fold 3

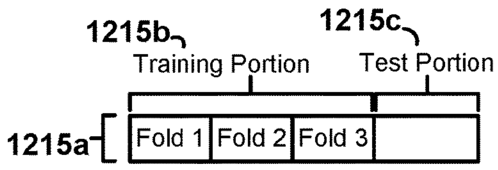

*FIG. 12C*

| | Class "Inside" | Class "Outside" |
|---|---|---|
| Intermediate Classifier 1 | 0.5 | 0.5 |
| Intermediate Classifier 2 | 0.8 | 0.2 |
| Intermediate Classifier 3 | 0.6 | 0.4 |
| Intermediate Classifier 4 | 0.2 | 0.8 |
| Intermediate Classifier 5 | 1.0 | 0.0 |
| max_cnt | 4 | 2 |
| means | 0.62 | 0.38 |
*FIG. 14A*
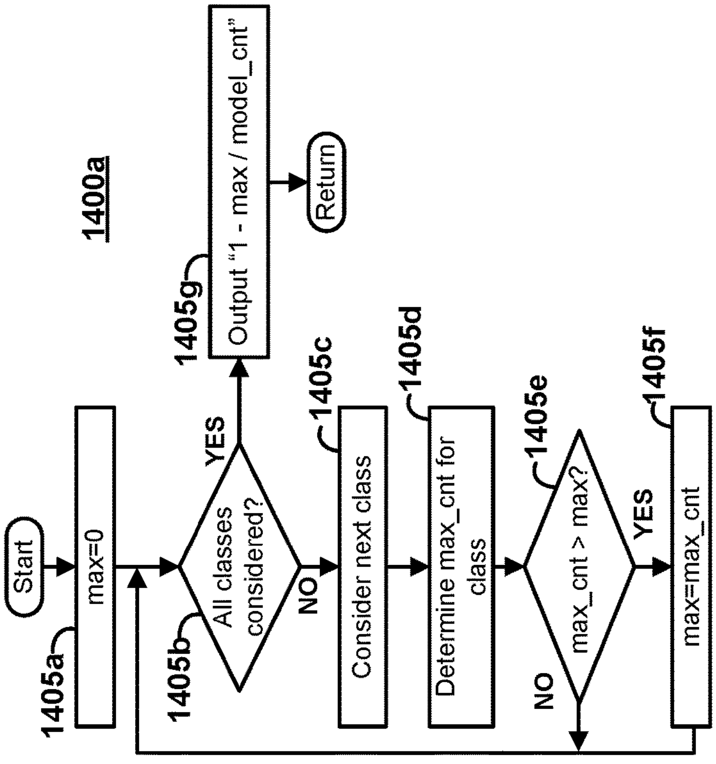
*FIG. 14B*
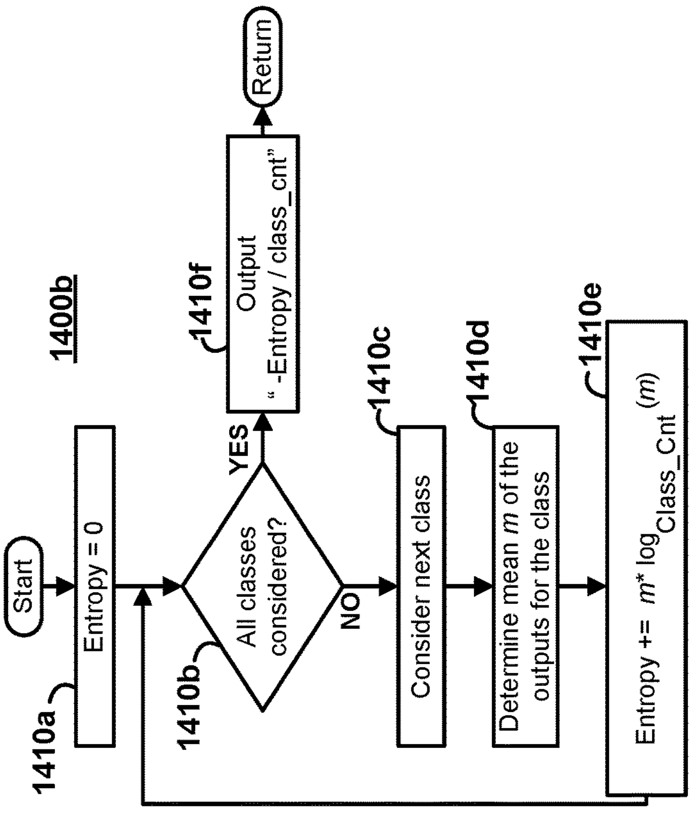
*FIG. 14C*
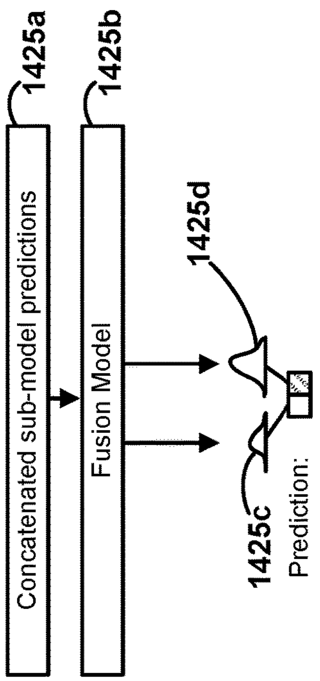
*FIG. 14D*

| Name | Surgery Type | Video Sessions | Duration (minutes) | Number of Frames | Number of Out-of-Body Frames |
|---|---|---|---|---|---|
| DaVinci16 | Robotic-Assisted | 16 | 88.15 (+/- 33.25) | 84622 | 16271 |
| Cholec80 | Not Robotic-Assisted | 80 | 36.70 (+/- 16.81) | 176192 | 3444 |
*FIG. 16A*
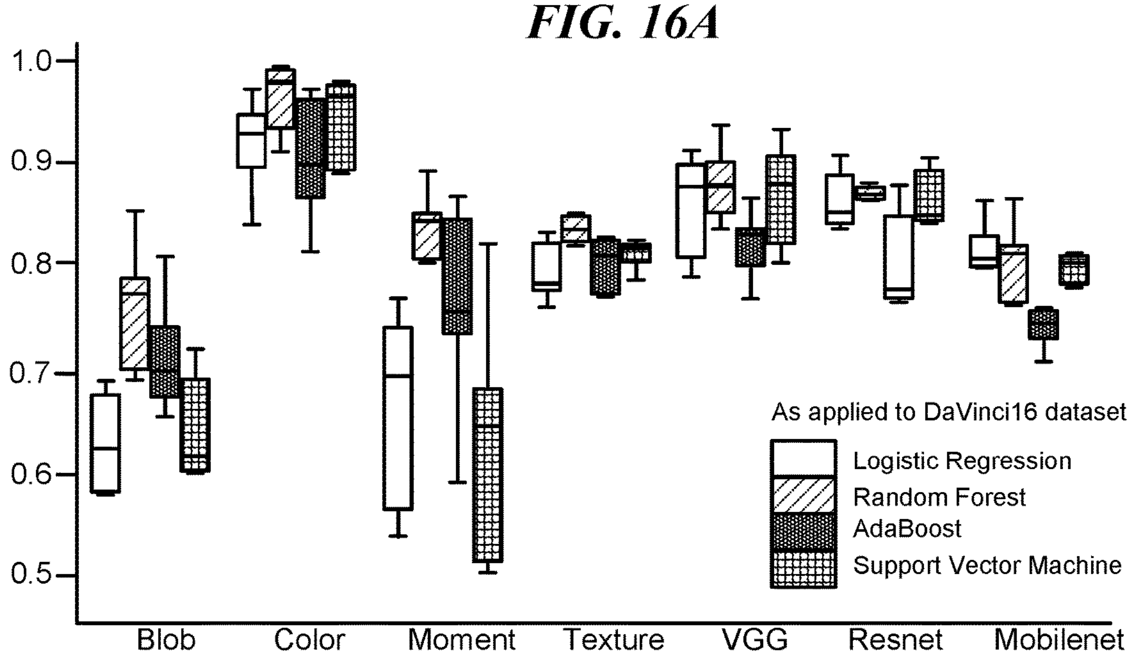
*FIG. 16B*
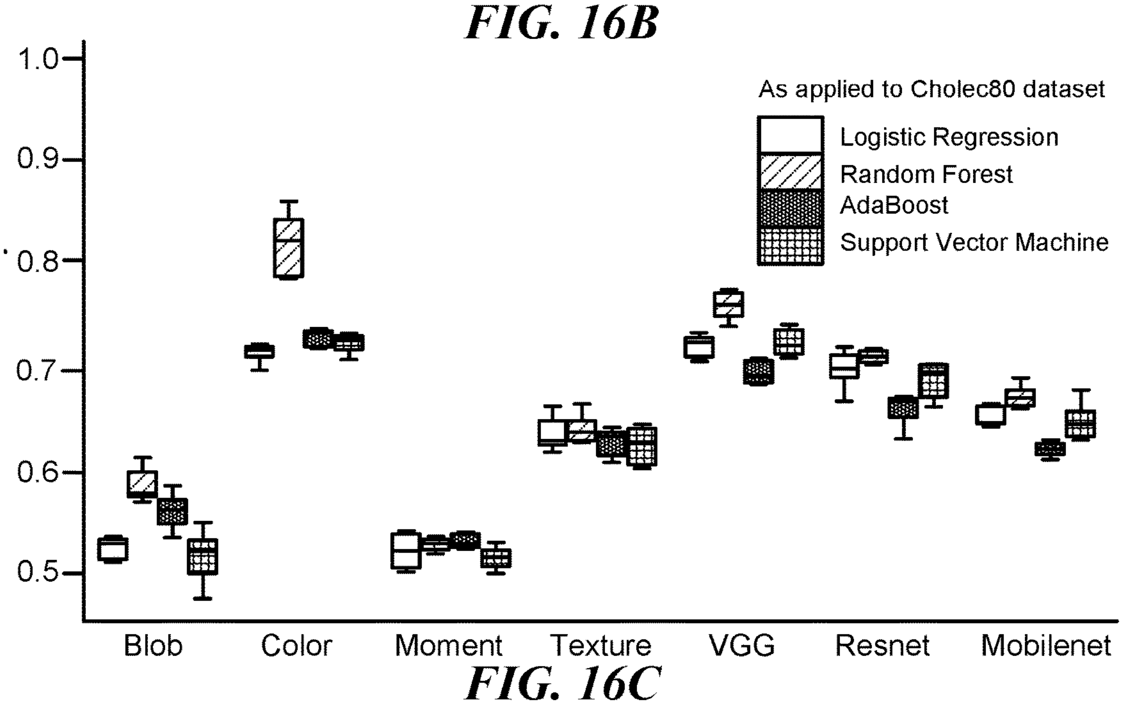
*FIG. 16C*

| Surgery | Feature | Frame Level | | | Session Level | | |
|---|---|---|---|---|---|---|---|
| | | Precision % | Recall % | f1 | Precision % | Recall % | f1 |
| Robot | Blob | 82.05 | 84.17 | 0.83 | 80.22 | 80.22 | 0.75 |
| | Color | 94.61 | 98.06 | 0.95 | 95.30 | 96.27 | 0.95 |
| | Texture | 89.05 | 88.29 | 0.88 | 81.94 | 88.00 | 0.83 |
| | Moment | 84.02 | 87.07 | 0.85 | 85.41 | 79.58 | 0.85 |
| | VGG16 | 94.10 | 89.46 | 0.91 | 88.75 | 88.02 | 0.86 |
| | RestNet50 | 92.02 | 88.93 | 0.90 | 87.22 | 87.67 | 0.87 |
| | MobileNet | 90.52 | 84.00 | 0.86 | 82.32 | 79.90 | 0.80 |
| Laparo. | Blob | 55.88 | 85.66 | 0.57 | 57.61 | 83.68 | 0.58 |
| | Color | 73.94 | 94.77 | 0.81 | 77.7 | 92.71 | 0.81 |
| | Texture | 58.66 | 89.38 | 0.62 | 88.61 | 63.53 | 0.64 |
| | Moment | 62.61 | 56.58 | 0.52 | 64.69 | 55.95 | 0.52 |
| | VGG16 | 70.86 | 90.49 | 0.77 | 66.22 | 90.98 | 0.71 |
| | RestNet50 | 66.07 | 86.61 | 0.72 | 66.83 | 83.99 | 0.71 |
| | MobileNet | 62.83 | 78.17 | 0.67 | 63.99 | 77.08 | 0.67 |

| Feature | Robot -> Laparoscopic | | | Laparoscopic -> Robot | | |
|---|---|---|---|---|---|---|
| | Precision % | Recall % | f1 | Precision % | Recall % | f1 |
| Blob | 59.25 | 74.81 | 0.61 | 65.41 | 68.09 | 0.64 |
| Color | 81.56 | 72.15 | 0.73 | 92.34 | 96.01 | 0.93 |
| Texture | 65.69 | 70.10 | 0.62 | 76.21 | 86.49 | 0.78 |
| Moment | 69.08 | 64.10 | 0.62 | 84.04 | 64.10 | 0.64 |
| VGG16 | 80.54 | 75.53 | 0.75 | 79.12 | 91.30 | 0.82 |
| RestNet50 | 69.01 | 74.67 | 0.70 | 81.55 | 88.78 | 0.82 |
| MobileNet | 67.88 | 70.05 | 0.66 | 80.74 | 66.80 | 0.67 |

SYSTEMS AND METHODS FOR SURGICAL DATA CENSORSHIP

CROSS-REFERENCE TO RELATED APPLICATIONS

This application is a United States national stage application under 35 U.S.C. § 371 of International Application PCT/US2021/059952, filed upon Nov. 18, 2021 and entitled "SYSTEMS AND METHODS FOR SURGICAL DATA CENSORSHIP", which claims the benefit of, and priority to, U.S. Provisional Application No. 63/116,906, filed upon Nov. 22, 2020, entitled "SYSTEMS AND METHODS FOR SURGICAL DATA CENSORSHIP", each of which is incorporated by reference herein in its entirety for all purposes.

TECHNICAL FIELD

Various of the disclosed embodiments relate to systems and methods for excising non-surgical information from surgical data.

BACKGROUND

Recent advances in data processing technologies, such as new deep learning systems, have enabled many new applications and improvements in a variety of disciplines, such as finance, advertising, product management, etc. These technologies often depend for their success upon the availability of large amounts of data, e.g., for use in training and optimizing machine learning systems. As surgical theaters increasingly incorporate data gathering sensors, such as those in assistive surgical robotic systems, laparoscopic tools, etc., one may optimistically anticipate corresponding advances in surgical systems, methods, and outcomes.

Unfortunately, unlike stock market or warehouse inventory data, surgical data is often encumbered with considerable regulatory, business, and cultural restrictions. For example, requirements in the Health Insurance Portability and Accountability Act (HIPPA) restrict when, where, and how patient data may be distributed and used. Hospitals and doctors may also be reluctant to share data which may implicate personal liability or privacy issues. In addition to these already considerable challenges, disparities in sensor availability and data gathering abilities between different surgical theaters may also complicate the uniform acquisition of surgical data. Such uniform acquisition may be especially important if one wishes to avoid undesirable overfitting or bias in the data's subsequent processing. Where the data is to be gathered, analyzed, and acted upon in real-time during a surgical operation, such challenges may be even more acute and disruptive. Unacceptable delays in the processing pipeline may compromise downstream analysis and, indeed, may even prevent certain downstream operations entirely.

Accordingly, there exists a need for improved surgical data gathering systems and methods, able to acquire useful data despite these many challenges.

BRIEF DESCRIPTION OF THE DRAWINGS

Various of the embodiments introduced herein may be better understood by referring to the following Detailed Description in conjunction with the accompanying drawings, in which like reference numerals indicate identical or functionally similar elements:

FIG. 5A is a schematic illustration of surgical data as may be received at a processing system in some embodiments;

FIG. 5B is a table of example tasks as may be used in conjunction with various disclosed embodiments;

FIG. 12A is a flow diagram illustrating various operations in a process as may be implemented in some embodiments for training one or more intermediate machine learning models, e.g., as appear in FIG. 11A;

FIG. 12B is a flow diagram illustrating various operations in an intermediate machine learning model training process, e.g., as may be applied at block 1205*f* of FIG. 12A in some embodiments;

FIG. 12C is an example training dataset breakdown as may be applied when training in accordance with the process of FIG. 12B in some embodiments;

FIG. 14A is a table of abstract example classification results as may be considered in the uncertainty calculations of FIGS. 14B and 14C;

FIG. 14B is a flow diagram illustrating various operations in a process for calculating uncertainty with class counts as may be implemented in some embodiments;

FIG. 14C is a flow diagram illustrating various operations in a process for calculating uncertainty with entropy as may be implemented in some embodiments;

FIG. 14D is a schematic depiction of uncertainty results using a generative machine learning model as may be employed in some embodiments;

FIG. 16A is table depicting properties of two example datasets used in evaluating various example implementations of various embodiments;

FIG. 16B is a plot comparing F1 scores for results using different intermediate models upon specific features generated from the DaVinci16 dataset;

FIG. 16C is a plot comparing F1 scores for results using different intermediate models upon specific features generated from the Cholec80 dataset;

Figure 1A:
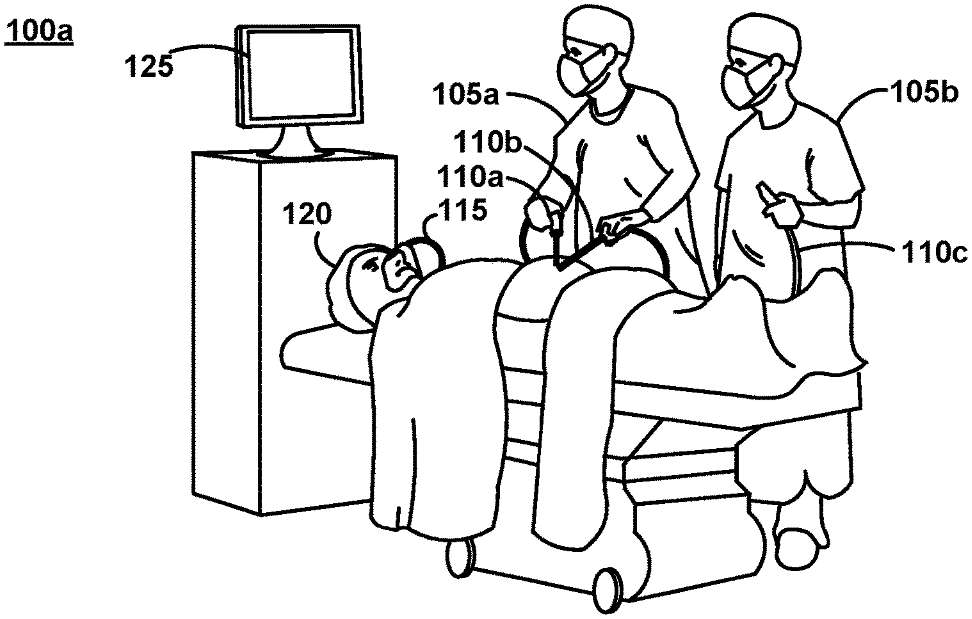
FIG. 1A is a schematic view of various elements appearing in a surgical theater during a surgical operation as may occur in relation to some embodiments.

The specific examples depicted in the drawings have been selected to facilitate understanding. Consequently, the disclosed embodiments should not be restricted to the specific details in the drawings or the corresponding disclosure. For example, the drawings may not be drawn to scale, the dimensions of some elements in the figures may have been adjusted to facilitate understanding, and the operations of the embodiments associated with the flow diagrams may encompass additional, alternative, or fewer operations than those depicted here. Thus, some components and/or operations may be separated into different blocks or combined into a single block in a manner other than as depicted. The embodiments are intended to cover all modifications, equivalents, and alternatives falling within the scope of the disclosed examples, rather than limit the embodiments to the particular examples described or depicted.

DETAILED DESCRIPTION

Example Surgical Theaters Overview

FIG. 1A is a schematic view of various elements appearing in a surgical theater 100*a* during a surgical operation as may occur in relation to some embodiments. Particularly, FIG. 1A depicts a non-robotic surgical theater 100*a*, wherein a patient-side surgeon 105*a* performs an operation upon a patient 120 with the assistance of one or more assisting members 105*b*, who may themselves be surgeons, physician's assistants, nurses, technicians, etc. The surgeon 105*a* may perform the operation using a variety of tools, e.g., a visualization tool 110*b* such as a laparoscopic ultrasound or endoscope, and a mechanical end effector 110*a* such as scissors, retractors, a dissector, etc.

The visualization tool 110*b* provides the surgeon 105*a* with an interior view of the patient 120, e.g., by displaying visualization output from a camera mechanically and electrically coupled with the visualization tool 110*b*. The surgeon may view the visualization output, e.g., through an eyepiece coupled with visualization tool 110*b* or upon a display 125 configured to receive the visualization output. For example, where the visualization tool 110*b* is an endoscope, the visualization output may be a color or grayscale image. Display 125 may allow assisting member 105*b* to monitor surgeon 105*a*'s progress during the surgery. The visualization output from visualization tool 110*b* may be recorded and stored for future review, e.g., using hardware or software on the visualization tool 110*b* itself, capturing the visualization output in parallel as it is provided to display 125, or capturing the output from display 125 once it appears on-screen, etc. While two-dimensional video capture with visualization tool 110*b* may be discussed extensively herein, as when visualization tool 110*b* is an endoscope, one will appreciate that, in some embodiments, visualization tool 110*b* may capture depth data instead of, or in addition to, two-dimensional image data (e.g., with a laser rangefinder, stereoscopy, etc.). Accordingly, one will appreciate that it may be possible to apply the two-dimensional operations discussed herein, mutatis mutandis, to such three-dimensional depth data when such data is available. For example, machine learning model inputs may be expanded or modified to accept features derived from such depth data.

A single surgery may include the performance of several groups of actions, each group of actions forming a discrete unit referred to herein as a task. For example, locating a tumor may constitute a first task, excising the tumor a second task, and closing the surgery site a third task. Each task may include multiple actions, e.g., a tumor excision task may require several cutting actions and several cauterization actions. While some surgeries require that tasks assume a specific order (e.g., excision occurs before closure), the order and presence of some tasks in some surgeries may be allowed to vary (e.g., the elimination of a precautionary task or a reordering of excision tasks where the order has no effect). Transitioning between tasks may require the surgeon 105*a* to remove tools from the patient, replace tools with different tools, or introduce new tools. Some tasks may require that the visualization tool 110*b* be removed and repositioned relative to its position in a previous task. While some assisting members 105*b* may assist with surgery-related tasks, such as administering anesthesia 115 to the patient 120, assisting members 105*b* may also assist with these task transitions, e.g., anticipating the need for a new tool 110*c*.

Figure 1B:
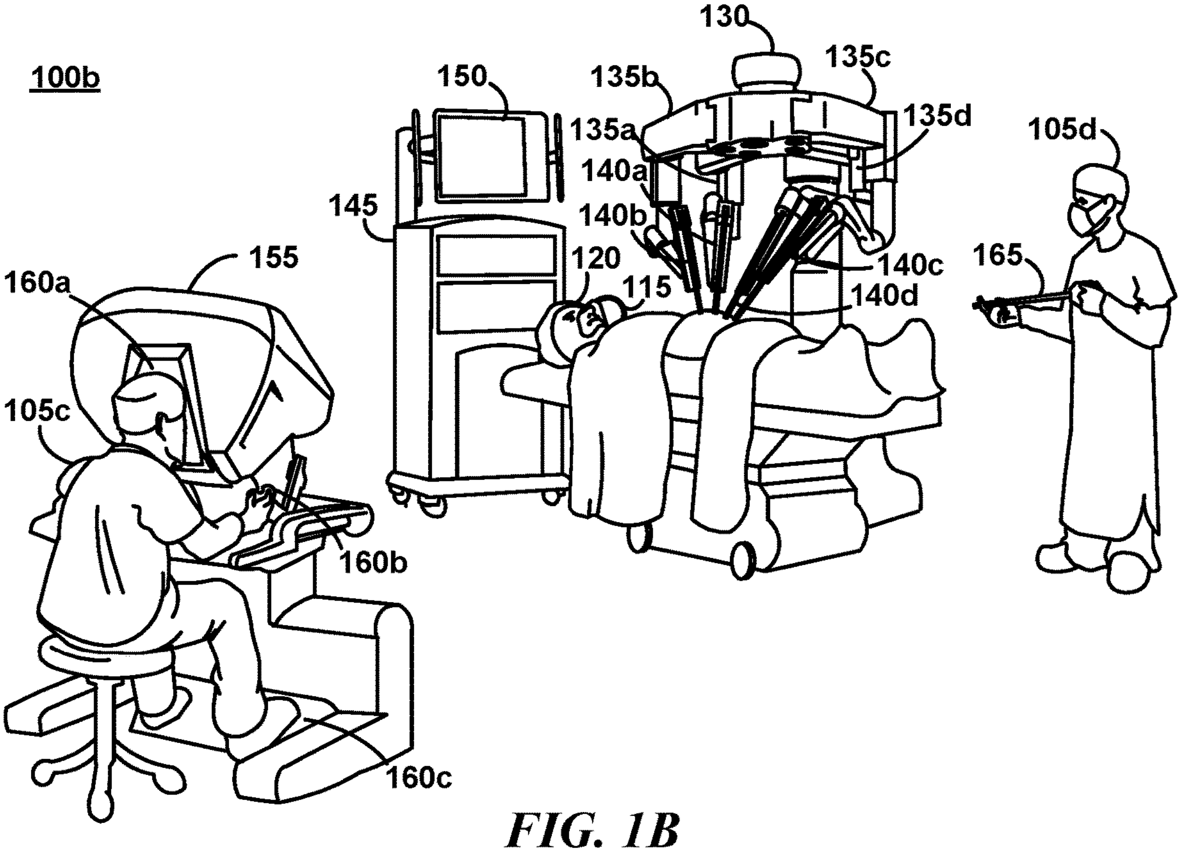
FIG. 1B is a schematic view of various elements appearing in a surgical theater during a surgical operation employing a surgical robot as may occur in relation to some embodiments.

Advances in technology have enabled procedures such as that depicted in FIG. 1A to also be performed with robotic systems, as well as the performance of procedures unable to be performed in non-robotic surgical theater 100*a*. Specifically, FIG. 1B is a schematic view of various elements appearing in a surgical theater 100*b* during a surgical operation employing a surgical robot, such as a da Vinci™ surgical system, as may occur in relation to some embodiments. Here, patient side cart 130 having tools 140*a*, 140*b*, 140*c*, and 140*d* attached to each of a plurality of arms 135*a*, 135*b*, 135*c*, and 135*d*, respectively, may take the position of patient-side surgeon 105*a*. As before, the tools 140*a*, 140*b*, 140*c*, and 140*d* may include a visualization tool 140*d*, such as an endoscope, laparoscopic ultrasound, etc. An operator 105*c*, who may be a surgeon, may view the output of visualization tool 140*d* through a display 160*a* upon a surgeon console 155. By manipulating a hand-held input mechanism 160*b* and pedals 160*c*, the operator 105*c* may remotely communicate with tools 140*a-d* on patient side cart 130 so as to perform the surgical procedure on patient 120. Indeed, the operator 105*c* may or may not be in the same physical location as patient side cart 130 and patient 120 since the communication between surgeon console 155 and patient side cart 130 may occur across a telecommunication network in some embodiments. An electronics/control console 145 may also include a display 150 depicting patient vitals and/or the output of visualization tool 140*d*.

Similar to the task transitions of non-robotic surgical theater 100*a*, the surgical operation of theater 100*b* may require that tools 140*a-d*, including the visualization tool 140*d*, be removed or replaced for various tasks as well as new tools, e.g., new tool 165, introduced. As before, one or more assisting members 105*d* may now anticipate such changes, working with operator 105*c* to make any necessary adjustments as the surgery progresses.

Also similar to the non-robotic surgical theater 100*a*, the output form the visualization tool 140*d* may here be recorded, e.g., at patient side cart 130, surgeon console 155, from display 150, etc. While some tools 110*a*, 110*b*, 110*c* in non-robotic surgical theater 100*a* may record additional data, such as temperature, motion, conductivity, energy levels, etc. the presence of surgeon console 155 and patient side cart 130 in theater 100*b* may facilitate the recordation of considerably more data than is only output from the visualization tool 140*d*. For example, operator 105*c*'s manipulation of hand-held input mechanism 160*b*, activation of pedals 160*c*, eye movement within display 160*a*, etc. may all be recorded. Similarly, patient side cart 130 may record tool activations (e.g., the application of radiative energy, closing of scissors, etc.), movement of end effectors, etc. throughout the surgery.

Machine Learning Foundational Concepts—Overview

This section provides a foundational description of machine learning model architectures and methods as may be relevant to various of the disclosed embodiments. Machine learning comprises a vast, heterogeneous landscape and has experienced many sudden and overlapping developments. Given this complexity, practitioners have not always used terms consistently or with rigorous clarity. Accordingly, this section seeks to provide a common ground to better ensure the reader's comprehension of the disclosed embodiments' substance. One will appreciate that exhaustively addressing all known machine learning models, as well as all known possible variants of the architectures, tasks, methods, and methodologies thereof herein is not feasible. Instead, one will appreciate that the examples discussed herein are merely representative and that various of the disclosed embodiments may employ many other architectures and methods than those which are explicitly discussed.

Figure 2A:
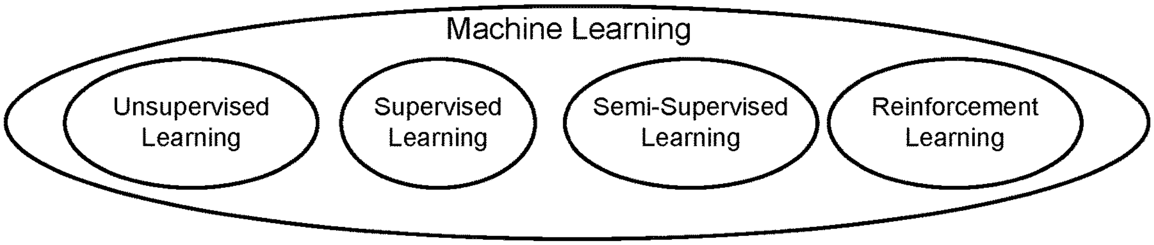
FIG. 2A is a schematic Euler diagram depicting conventional groupings of machine learning models and methodologies.

To orient the reader relative to the existing literature, FIG. 2A depicts conventionally recognized groupings of machine learning models and methodologies, also referred to as techniques, in the form of a schematic Euler diagram. The groupings of FIG. 2A will be described with reference to FIGS. 2B-E in their conventional manner so as to orient the reader, before a more comprehensive description of the machine learning field is provided with respect to FIG. 2F.

Figure 2B:
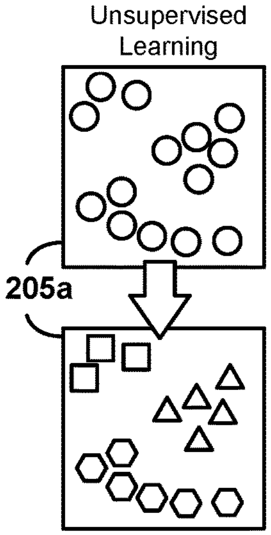
FIG. 2B is a schematic diagram depicting various operations of an example unsupervised learning method in accordance with the conventional groupings of FIG. 2A.

The conventional groupings of FIG. 2A typically distinguish between machine learning models and their methodologies based upon the nature of the input the model is expected to receive or that the methodology is expected to operate upon. Unsupervised learning methodologies draw inferences from input datasets which lack output metadata (also referred to as a "unlabeled data") or by ignoring such metadata if it is present. For example, as shown in FIG. 2B, an unsupervised K-Nearest-Neighbor (KNN) model architecture may receive a plurality of unlabeled inputs, represented by circles in a feature space 205*a*. A feature space is a mathematical space of inputs which a given model architecture is configured to operate upon. For example, if a 128×128 grayscale pixel image were provided as input to the KNN, it may be treated as a linear array of 16,384 "features" (i.e., the raw pixel values). The feature space would then be a 16,384 dimensional space (a space of only two dimensions is show in FIG. 2B to facilitate understanding). If instead, e.g., a Fourier transform were applied to the pixel data, then the resulting frequency magnitudes and phases may serve as the "features" to be input into the model architecture. Though input values in a feature space may sometimes be referred to as feature "vectors," one will appreciate that not all model architectures expect to receive feature inputs in a linear form (e.g., some deep learning networks expect input features as matrices or tensors). Accordingly, mention of a vector of features, matrix of features, etc. should be seen as exemplary of possible forms that may be input to a model architecture absent context indicating otherwise. Similarly, reference to an "input" will be understood to include any possible feature type or form acceptable to the architecture. Continuing with the example of FIG. 2B, the KNN classifier may output associations between the input vectors and various groupings determined by the KNN classifier as represented by the indicated squares, triangles, and hexagons in the figure. Thus, unsupervised methodologies may include, e.g., determining clusters in data as in this example, reducing or changing the feature dimensions used to represent data inputs, etc.

Figure 2C:
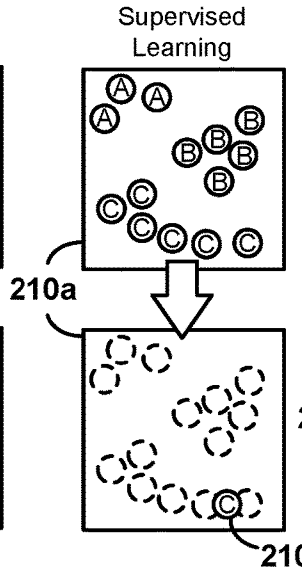
FIG. 2C is a schematic diagram depicting various operations of an example supervised learning method in accordance with the conventional groupings of FIG. 2A.

Supervised learning models receive input datasets accompanied with output metadata (referred to as "labeled data") and modify the model architecture's parameters (such as the biases and weights of a neural network, or the support vectors of an SVM) based upon this input data and metadata so as to better map subsequently received inputs to the desired output. For example, an SVM supervised classifier may operate as shown in FIG. 2C, receiving as training input a plurality of input feature vectors, represented by circles, in a feature space 210*a*, where the feature vectors are accompanied by output labels A, B, or C, e.g., as provided by the practitioner. In accordance with a supervised learning methodology, the SVM uses these label inputs to modify its parameters, such that when the SVM receives a new, previously unseen input 210*c* in the feature vector form of the feature space 210*a*, the SVM may output the desired classification "C" in its output. Thus, supervised learning methodologies may include, e.g., performing classification as in this example, performing a regression, etc.

Figure 2D:
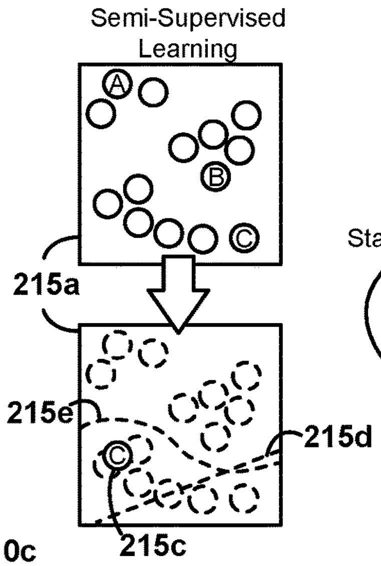
FIG. 2D is a schematic diagram depicting various operations of an example semi-supervised learning method in accordance with the conventional groupings of FIG. 2A.
Figure 2E:
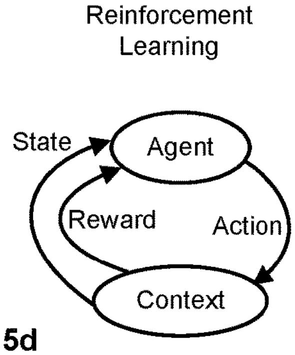
FIG. 2E is a schematic diagram depicting various operations of an example reinforcement learning method in accordance with the conventional division of FIG. 2A.

Semi-supervised learning methodologies inform their model's architecture's parameter adjustment based upon both labeled and unlabeled data. For example, a supervised neural network classifier may operate as shown in FIG. 2D, receiving some training input feature vectors in the feature space 215*a* labeled with a classification A, B, or C and some training input feature vectors without such labels (as depicted with circles lacking letters). Absent consideration of the unlabeled inputs, a naïve supervised classifier may distinguish between inputs in the B and C classes based upon a simple planar separation 215*d* in the feature space between the available labeled inputs. However, a semi-supervised classifier, by considering the unlabeled as well as the labeled input feature vectors, may employ a more nuanced separation 215*e*. Unlike the simple separation 215*d* the nuanced separation 215*e* may correctly classify a new input 215*c* as being in the C class. Thus, semi-supervised learning methods and architectures may include applications in both supervised and unsupervised learning wherein at least some of the available data is labeled.

Finally, the conventional groupings of FIG. 2A distinguish reinforcement learning methodologies as those wherein an agent, e.g., a robot or digital assistant, takes some action (e.g., moving a manipulator, making a suggestion to a user, etc.) which affects the agent's environmental context (e.g., object locations in the environment, the disposition of the user, etc.), precipitating a new environment state and some associated environment-based reward (e.g., a positive reward if environment objects are now closer to a goal state, a negative reward if the user is displeased, etc.). Thus, reinforcement learning may include, e.g., updating a digital assistant based upon a user's behavior and expressed preferences, an autonomous robot maneuvering through a factory, a computer playing chess, etc.

As mentioned, while many practitioners will recognize the conventional taxonomy of FIG. 2A, the groupings of FIG. 2A obscure machine learning's rich diversity, and may inadequately characterize machine learning architectures and techniques which fall in multiple of its groups or which fall entirely outside of those groups (e.g., random forests and neural networks may be used for supervised or for unsupervised learning tasks; similarly, some generative adversarial networks, while employing supervised classifiers, would not themselves easily fall within any one of the groupings of FIG. 2A). Accordingly, though reference may be made herein to various terms from FIG. 2A to facilitate the reader's understanding, this description should not be limited to the procrustean conventions of FIG. 2A. For example, FIG. 2F offers a more flexible machine learning taxonomy.

In particular, FIG. 1F approaches machine learning as comprising models 220*a*, model architectures 220*b*, methodologies 220*e*, methods 220*d*, and implementations 220*c*. At a high level, model architectures 220*b* may be seen as species of their respective genus models 220*a* (model A having possible architectures A1, A2, etc.; model B having possible architectures B1, B2, etc.). Models 220*a* refer to descriptions of mathematical structures amenable to implementation as machine learning architectures. For example, KNN, neural networks, SVMs, Bayesian Classifiers, Principal Component Analysis (PCA), etc., represented by the boxes "A", "B", "C", etc. are examples of models (ellipses in the figures indicate the existence of additional items). While models may specify general computational relations, e.g., that an SVM include a hyperplane, that a neural network have layers or neurons, etc., models may not specify an architecture's particular structure, such as the architecture's choice of hyperparameters and dataflow, for performing a specific task, e.g., that the SVM employ a Radial Basis Function (RBF) kernel, that a neural network be configured to receive inputs of dimension 256×256×3, etc. These structural features may, e.g., be chosen by the practitioner or result from a training or configuration process. Note that the universe of models 220*a* also includes combinations of its members as, for example, when creating an ensemble model (discussed below in relation to FIG. 3G) or when using a pipeline of models (discussed below in relation to FIG. 3H).

For clarity, one will appreciate that many architectures comprise both parameters and hyperparameters. An architecture's parameters refer to configuration values of the architecture, which may be adjusted based directly upon the receipt of input data (such as the adjustment of weights and biases of a neural network during training). Different architectures may have different choices of parameters and relations therebetween, but changes in the parameter's value, e.g., during training, would not be considered a change in architecture. In contrast, an architecture's hyperparameters refer to configuration values of the architecture which are not adjusted based directly upon the receipt of input data (e.g., the K number of neighbors in a KNN implementation, the learning rate in a neural network training implementation, the kernel type of an SVM, etc.). Accordingly, changing a hyperparameter would typically change an architecture. One will appreciate that some method operations, e.g., validation, discussed below, may adjust hyperparameters, and consequently the architecture type, during training. Consequently, some implementations may contemplate multiple architectures, though only some of them may be configured for use or used at a given moment.

In a similar manner to models and architectures, at a high level, methods 220*d* may be seen as species of their genus methodologies 220*e* (methodology I having methods I.1, I.2, etc.; methodology II having methods II.1, II.2, etc.). Methodologies 220*e* refer to algorithms amenable to adaptation as methods for performing tasks using one or more specific machine learning architectures, such as training the architecture, testing the architecture, validating the architecture, performing inference with the architecture, using multiple architectures in a Generative Adversarial Network (GAN), etc. For example, gradient descent is a methodology describing methods for training a neural network, ensemble learning is a methodology describing methods for training groups of architectures, etc. While methodologies may specify general algorithmic operations, e.g., that gradient descent take iterative steps along a cost or error surface, that ensemble learning consider the intermediate results of its architectures, etc., methods specify how a specific architecture should perform the methodology's algorithm, e.g., that the gradient descent employ iterative backpropagation on a neural network and stochastic optimization via Adam with specific hyperparameters, that the ensemble system comprise a collection of random forests applying AdaBoost with specific configuration values, that training data be organized into a specific number of folds, etc. One will appreciate that architectures and methods may themselves have sub-architecture and sub-methods, as when one augments an existing architecture or method with additional or modified functionality (e.g., a GAN architecture and GAN training method may be seen as comprising deep learning architectures and deep learning training methods). One will also appreciate that not all possible methodologies will apply to all possible models (e.g., suggesting that one perform gradient descent upon a PCA architecture, without further explanation, would seem nonsensical). One will appreciate that methods may include some actions by a practitioner or may be entirely automated.

As evidenced by the above examples, as one moves from models to architectures and from methodologies to methods, aspects of the architecture may appear in the method and aspects of the method in the architecture as some methods may only apply to certain architectures and certain architectures may only be amenable to certain methods. Appreciating this interplay, an implementation 220*c* is a combination of one or more architectures with one or more methods to form a machine learning system configured to perform one or more specified tasks, such as training, inference, generating new data with a GAN, etc. For clarity, an implementation's architecture need not be actively performing its method, but may simply be configured to perform a method (e.g., as when accompanying training control software is configured to pass an input through the architecture). Applying the method will result in performance of the task, such as training or inference. Thus, a hypothetical Implementation A (indicated by "Imp. A") depicted in FIG. 2F comprises a single architecture with a single method. This may correspond, e.g., to an SVM architecture configured to recognize objects in a 128×128 grayscale pixel image by using a hyperplane support vector separation method employing an RBF kernel in a space of 16,384 dimensions. The usage of an RBF kernel and the choice of feature vector input structure reflect both aspects of the choice of architecture and the choice of training and inference methods. Accordingly, one will appreciate that some descriptions of architecture structure may imply aspects of a corresponding method and vice versa. Hypothetical Implementation B (indicated by "Imp. B") may correspond, e.g., to a training method II.1 which may switch between architectures B1 and C1 based upon validation results, before an inference method III.3 is applied.

The close relationship between architectures and methods within implementations precipitates much of the ambiguity in FIG. 2A as the groups do not easily capture the close relation between methods and architectures in a given implementation. For example, very minor changes in a method or architecture may move a model implementation between the groups of FIG. 2A as when a practitioner trains a random forest with a first method incorporating labels (supervised) and then applies a second method with the trained architecture to detect clusters in unlabeled data (unsupervised) rather than perform inference on the data. Similarly, the groups of FIG. 2A may make it difficult to classify aggregate methods and architectures, e.g., as discussed below in relation to FIGS. 3F and 3G, which may apply techniques found in some, none, or all of the groups of FIG. 2A. Thus, the next sections discuss relations between various example model architectures and example methods with reference to FIGS. 3A-G and FIGS. 4A-J to facilitate clarity and reader recognition of the relations between architectures, methods, and implementations. One will appreciate that the discussed tasks are exemplary and reference therefore, e.g., to classification operations so as to facilitate understanding, should not be construed as suggesting that the implementation must be exclusively used for that purpose.

Figure 2F:
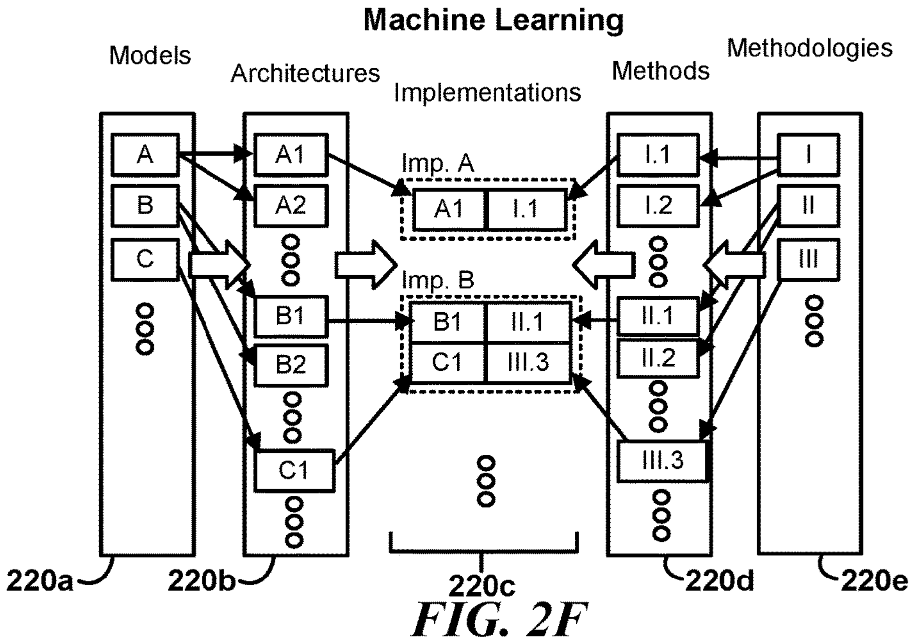
FIG. 2F is a schematic block diagram depicting relations between machine learning models, machine learning model architectures, machine learning methodologies, machine learning methods, and machine learning implementations.

For clarity, one will appreciate that the above explanation with respect to FIG. 2F is provided merely to facilitate reader comprehension and should accordingly not be construed in a limiting manner absent explicit language indicating as much. For example, naturally, one will appreciate that "methods" 220*d* are computer-implemented methods, but not all computer-implemented methods are methods in the sense of "methods" 220*d*. Computer-implemented methods may be logic without any machine learning functionality. Similarly, the term "methodologies" is not always used in the sense of "methodologies" 220*e*, but may refer to approaches without machine learning functionality. Similarly, while the terms "model" and "architecture" and "implementation" have been used above at 220*a*, 220*b* and 220*c*, the terms are not restricted to their distinctions here in FIG. 2F, absent language to that effect, and may be used to refer to the topology of machine learning components generally.

Machine Learning Foundational Concepts—Example Implementations

Figure 3A:
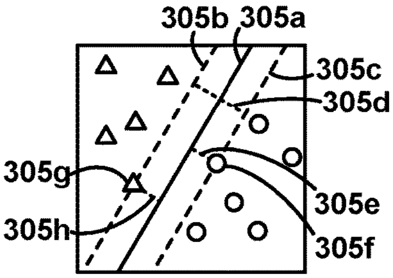
FIG. 3A is a schematic depiction of the operation of various aspects of an example Support Vector Machine (SVM) machine learning model architecture.

FIG. 3A is a schematic depiction of the operation of an example SVM machine learning model architecture. At a high level, given data from two classes (e.g. images of dogs and images of cats) as input features, represented by circles and triangles in the schematic of FIG. 3A, SVMs seek to determine a hyperplane separator 305*a* which maximizes the minimum distance from members of each class to the separator 305*a*. Here, the training feature vector 305*f* has the minimum distance 305*e* of all its peers to the separator 305*a*. Conversely, training feature vector 305*g* has the minimum distance 305*h* among all its peers to the separator 305*a*. The margin 305*d* formed between these two training feature vectors is thus the combination of distances 305*h* and 305*e* (reference lines 305*b* and 305*c* are provided for clarity) and, being the maximum minimum separation, identifies training feature vectors 305*f* and 305*g* as support vectors. While this example depicts a linear hyperplane separation, different SVM architectures accommodate different kernels (e.g., an RBF kernel), which may facilitate nonlinear hyperplane separation. The separator may be found during training and subsequent inference may be achieved by considering where a new input in the feature space falls relative to the separator. Similarly, while this example depicts feature vectors of two dimensions for clarity (in the two-dimensional plane of the paper), one will appreciate that may architectures will accept many more dimensions of features (e.g., a 128×128 pixel image may be input as 16,384 dimensions). While the hyperplane in this example only separates two classes, multi-class separation may be achieved in a variety of manners, e.g., using an ensemble architecture of SVM hyperplane separations in one-against-one, one-against-all, etc. configurations. Practitioners often use the LIBSVM™ and Scikit-learn™ libraries when implementing SVMs. One will appreciate that many different machine learning models, e.g., logistic regression classifiers, seek to identify separating hyperplanes.

Figure 3B:
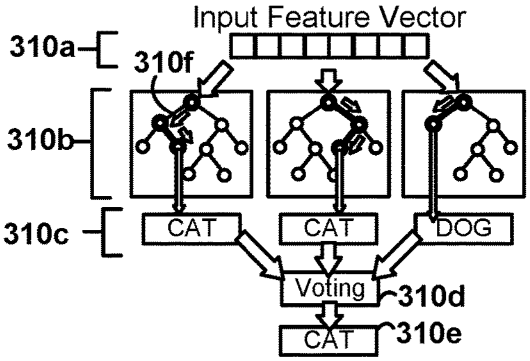
FIG. 3B is a schematic depiction of various aspects of the operation of an example random forest machine learning model architecture.

In the above example SVM implementation, the practitioner determined the feature format as part of the architecture and method of the implementation. For some tasks, architectures and methods which process inputs to determine new or different feature forms themselves may be desirable. Some random forests implementations may, in effect, adjust the feature space representation in this manner. For example, FIG. 3B depicts at a high level, an example random forest model architecture comprising a plurality of decision trees 310*b*, each of which may receive all, or a portion, of input feature vector 310*a* at their root node. Though three trees are shown in this example architecture with maximum depths of three levels, one will appreciate that forest architectures with fewer or more trees and different levels (even between trees of the same forest) are possible. As each tree considers its portion of the input, it refers all or a portion of the input to a subsequent node, e.g., path 310*f* based upon whether the input portion does or does not satisfy the conditions associated with various nodes. For example, when considering an image, a single node in a tree may query whether a pixel value at position in the feature vector is above or below a certain threshold value. In addition to the threshold parameter some trees may include additional parameters and their leaves may include probabilities of correct classification. Each leaf of the tree may be associated with a tentative output value 310*c* for consideration by a voting mechanism 310*d* to produce a final output 310*e*, e.g., by taking a majority vote among the trees or by the probability weighted average of each tree's predictions. This architecture may lend itself to a variety of training methods, e.g., as different data subsets are trained on different trees.

Tree depth in a random forest, as well as different trees, may facilitate the random forest model's consideration of feature relations beyond direct comparisons of those in the initial input. For example, if the original features were pixel values, the trees may recognize relationships between groups of pixel values relevant to the task, such as relations between "nose" and "ear" pixels for cat/dog classification. Binary decision tree relations, however, may impose limits upon the ability to discern these "higher order" features.

Figure 3C:
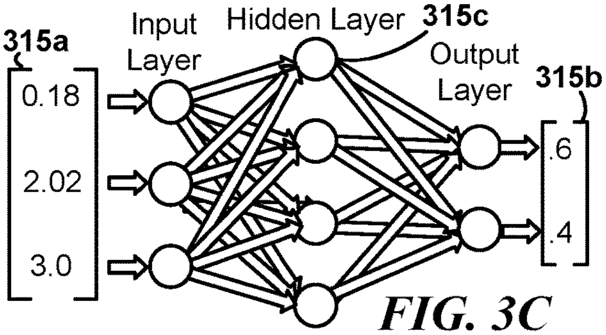
FIG. 3C is a schematic depiction of various aspects of the operation of an example neural network machine learning model architecture.

Neural networks, as in the example architecture of FIG. 3C may also be able to infer higher order features and relations between the initial input vector. However, each node in the network may be associated with a variety of parameters and connections to other nodes, facilitating more complex decisions and intermediate feature generations than the conventional random forest tree's binary relations. As shown in FIG. 3C, a neural network architecture may comprise an input layer, at least one hidden layer, and an output layer. Each layer comprises a collection of neurons which may receive a number of inputs and provide an output value, also referred to as an activation value, the output values 315*b* of the final output layer serving as the network's final result. Similarly, the inputs 315*a* for the input layer may be received form the input data, rather than a previous neuron layer.

Figure 3G:
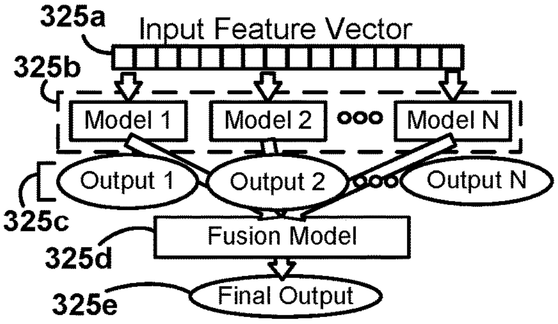
FIG. 3G is a schematic depiction of various aspects of the operation of an example ensemble architecture.
Figure 3D:
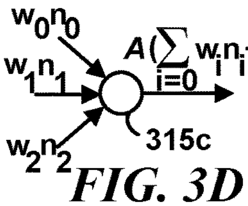
FIG. 3D is a schematic depiction of a possible relation between inputs and outputs in a node of the example neural network architecture of FIG. 3C.

FIG. 3D depicts the input and output relations at the node 315*c* of FIG. 3C. Specifically, the output $n_{out}$ of node 315*c* may relate to its three (zero-base indexed) inputs as follows:

$$n_{out} = A\left(\sum_{i=0}^{2} w_i n_i + b\right) \quad (1)$$

where vin is the weight parameter on the output of $i^{th}$ node in the input layer, $\eta_i$ is the output value from the activation function of the $i^{th}$ node in the input layer, b is a bias value associated with node 315_c_, and A is the activation function associated with node 315_c_. Note that in this example the sum is over each of the three input layer node outputs and weight pairs and only a single bias value b is added. The activation function A may determine the node's output based upon the values of the weights, biases, and previous layer's nodes' values. During training, each of the weight and bias parameters may be adjusted depending upon the training method used. For example, many neural networks employ a methodology known as backward propagation, wherein, in some method forms, the weight and bias parameters are randomly initialized, a training input vector is passed through the network, and the difference between the network's output values and the desirable output values for that vector's metadata determined. The difference can then be used as the metric by which the network's parameters are adjusted, "propagating" the error as a correction throughout the network so that the network is more likely to produce the proper output for the input vector in a future encounter. While three nodes are shown in the input layer of the implementation of FIG. 3C for clarity, one will appreciate that there may be more or less nodes in different architectures (e.g., there may be 16,384 such nodes to receive pixel values in the above 128×128 grayscale image examples). Similarly, while each of the layers in this example architecture are shown as being fully connected with the next layer, one will appreciate that other architectures may not connect each of the nodes between layers in this manner. Neither will all the neural network architectures process data exclusively from left to right or consider only a single feature vector at a time. For example, Recurrent Neural Networks (RNNs) include classes of neural network methods and architectures which consider previous input instances when considering a current instance. Architectures may be further distinguished based upon the activation functions used at the various nodes, e.g.: logistic functions, rectified linear unit functions (ReLU), softplus functions, etc. Accordingly, there is considerable diversity between architectures.

One will recognize that many of the example machine learning implementations so far discussed in this overview are "discriminative" machine learning models and methodologies (SVMs, logistic regression classifiers, neural networks with nodes as in FIG. 3D, etc.). Generally, discriminative approaches assume a form which seeks to find the following probability of Equation 2:

$$P(\text{output}|\text{input}) \quad (2)$$

That is, these models and methodologies seek structures distinguishing classes (e.g., the SVM hyperplane) and estimate parameters associated with that structure (e.g., the support vectors determining the separating hyperplane) based upon the training data. One will appreciate, however, that not all models and methodologies discussed herein may assume this discriminative form, but may instead be one of multiple "generative" machine learning models and corresponding methodologies (e.g., a Naïve Bayes Classifier, a Hidden Markov Model, a Bayesian Network, etc.). These generative models instead assume a form which seeks to find the following probabilities of Equation 3:

$$P(\text{output}), P(\text{input}|\text{output}) \quad (3)$$

That is, these models and methodologies seek structures (e.g., a Bayesian Neural Network, with its initial parameters and prior) reflecting characteristic relations between inputs and outputs, estimate these parameters from the training data and then use Bayes rule to calculate the value of Equation 2. One will appreciate that performing these calculations directly is not always feasible, and so methods of numerical approximation may be employed in some of these generative models and methodologies.

Figure 3E:
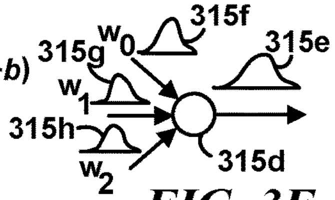
FIG. 3E is a schematic depiction of an example input-output relation variation as may occur in a Bayesian neural network.

One will appreciate that such generative approaches may be used mutatis mutandis herein to achieve results presented with discriminative implementations and vice versa. For example, FIG. 3E illustrates an example node 315_d_ as may appear in a Bayesian Neural Network. Unlike the node 315_c_, which receives numerical values simply, one will appreciate that a node in a Bayesian Neural network, such as node 315_d_, may receive weighted probability distributions 315_f_, 315_g_, 315_h_ (e.g., the parameters of such distributions) and may itself output a distribution 315_e_. Thus, one will recognize that while one may, e.g., determine a classification uncertainty in a discriminative model via various post-processing techniques (e.g., comparing outputs with iterative applications of dropout to a discriminative neural network), one may achieve similar uncertainty measures by employing a generative model outputting a probability distribution, e.g., by considering the variance of distribution 315_e_. Thus, just as reference to one specific machine learning implementation herein is not intended to exclude substitution with any similarly functioning implementation, neither is reference to a discriminative implementation herein to be construed as excluding substitution with a generative counterpart where applicable, or vice versa.

Returning to a general discussion of machine learning approaches, while FIG. 3C depicts an example neural network architecture with a single hidden layer, many neural network architectures may have more than one hidden layer. Some networks with many hidden layers have produced surprisingly effective results and the term "deep" learning has been applied to these models to reflect the large number of hidden layers. Herein, deep learning refers to architectures and methods employing at least one neural network architecture having more than one hidden layer.

Figure 3F:
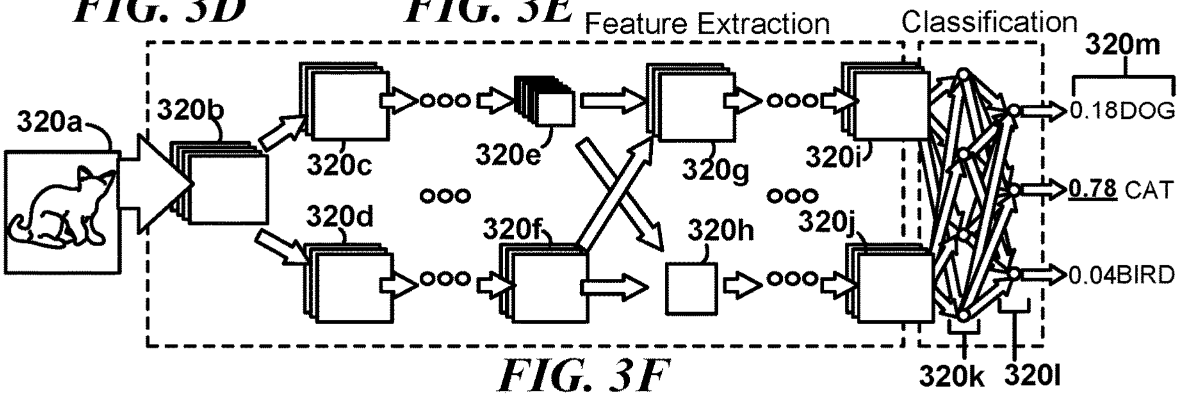
FIG. 3F is a schematic depiction of various aspects of the operation of an example deep learning architecture.

FIG. 3F is a schematic depiction of the operation of an example deep learning model architecture. In this example, the architecture is configured to receive a two-dimensional input 320_a_, such as a grayscale image of a cat. When used for classification, as in this example, the architecture may generally be broken into two portions: a feature extraction portion comprising a succession of layer operations and a classification portion, which determines output values based upon relations between the extracted features.

Many different feature extraction layers are possible, e.g., convolutional layers, max-pooling layers, dropout layers, cropping layers, etc. and many of these layers are themselves susceptible to variation, e.g., two-dimensional convolutional layers, three-dimensional convolutional layers, convolutional layers with different activation functions, etc. as well as different methods and methodologies for the network's training, inference, etc. As illustrated, these layers may produce multiple intermediate values 320_b-j_ of differing dimensions and these intermediate values may be processed along multiple pathways. For example, the original grayscale image 320_a_ may be represented as a feature input tensor of dimensions 128×128×1 (e.g., a grayscale image of 128 pixel width and 128 pixel height) or as a feature input tensor of dimensions 128×128×3 (e.g., an RGB image of 128 pixel width and 128 pixel height). Multiple convolutions with different kernel functions at a first layer may precipitate multiple intermediate values 320_b_ from this input. These intermediate values 320_b_ may themselves be considered by two different layers to form two new intermediate values 320*c* and 320*d* along separate paths (though two paths are shown in this example, one will appreciate that many more paths, or a single path, are possible in different architectures). Additionally, data may be provided in multiple "channels" as when an image has red, green, and blue values for each pixel as, for example, with the "×3" dimension in the 128×128×3 feature tensor (for clarity, this input has three "tensor" dimensions, but 49,152 individual "feature" dimensions). Various architectures may operate on the channels individually or collectively in various layers. The ellipses in the figure indicate the presence of additional layers (e.g., some networks have hundreds of layers). As shown, the intermediate values may change in size and dimensions, e.g., following pooling, as in values 320*e*. In some networks, intermediate values may be considered at layers between paths as shown between intermediate values 320*e*, 320*f*, 320*g*, 320*h*. Eventually, a final set of feature values appear at intermediate collection 320*i* and 320*j* and are fed to a collection of one or more classification layers 320*k* and 320*l*, e.g., via flattened layers, a SoftMax layer, fully connected layers, etc. to produce output values 320*m* at output nodes of layer 320*l*. For example, if N classes are to be recognized, there may be N output nodes to reflect the probability of each class being the correct class (e.g., here the network is identifying one of three classes and indicates the class "cat" as being the most likely for the given input), though some architectures many have fewer or have many more outputs. Similarly, some architectures may accept additional inputs (e.g., some flood fill architectures utilize an evolving mask structure, which may be both received as an input in addition to the input feature data and produced in modified form as an output in addition to the classification output values; similarly, some recurrent neural networks may store values from one iteration to be inputted into a subsequent iteration alongside the other inputs), may include feedback loops, etc.

TensorFlow™, Caffe™, and Torch™, are examples of common software library frameworks for implementing deep neural networks, though many architectures may be created "from scratch" simply representing layers as operations upon matrices or tensors of values and data as values within such matrices or tensors. Examples of deep learning network architectures include VGG-19, ResNet, Inception, DenseNet, etc.

While example paradigmatic machine learning architectures have been discussed with respect to FIGS. 3A through 3F, there are many machine learning models and corresponding architectures formed by combining, modifying, or appending operations and structures to other architectures and techniques. For example, FIG. 3G is a schematic depiction of an ensemble machine learning architecture. Ensemble models include a wide variety of architectures, including, e.g., "meta-algorithm" models, which use a plurality of weak learning models to collectively form a stronger model, as in, e.g., AdaBoost. The random forest of FIG. 3A may be seen as another example of such an ensemble model, though a random forest may itself be an intermediate classifier in an ensemble model.

In the example of FIG. 3G, an initial input feature vector 325*a* may be input, in whole or in part, to a variety of model implementations 325*b*, which may be from the same or different models (e.g., SVMs, neural networks, random forests, etc.). The outputs from these models 325*c* may then be received by a "fusion" model architecture 325*d* to generate a final output 325*e*. The fusion model implementation 325*d* may itself be the same or different model type as one of implementations 325*b*. For example, in some systems fusion model implementation 325*d* may be a logistic regression classifier and models 325*b* may be neural networks.

Figure 3H:
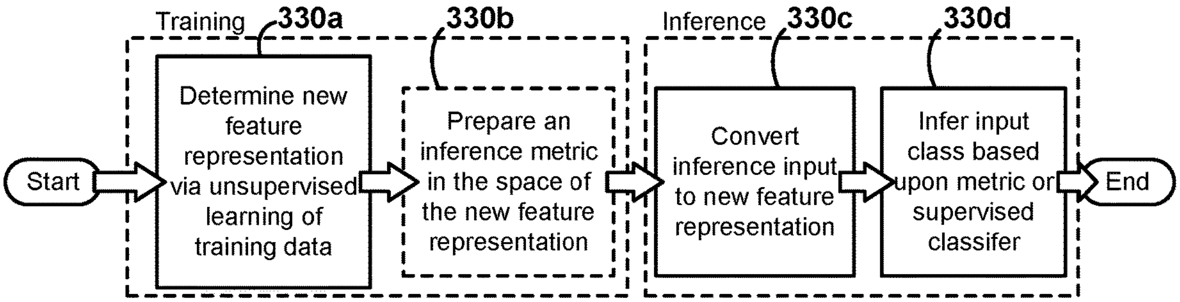
FIG. 3H is a schematic block diagram depicting various operations of an example pipeline architecture.

Just as one will appreciate that ensemble model architectures may facilitate greater flexibility over the paradigmatic architectures of FIGS. 3A through 3F, one should appreciate that modifications, sometimes relatively slight, to an architecture or its method may facilitate novel behavior not readily lending itself to the conventional grouping of FIG. 2A. For example, PCA is generally described as an unsupervised learning method and corresponding architecture, as it discerns dimensionality-reduced feature representations of input data which lack labels. However, PCA has often been used with labeled inputs to facilitate classification in a supervised manner, as in the EigenFaces application described in M. Turk and A. Pentland, "Eigenfaces for Recognition", J. Cognitive Neuroscience, vol. 3, no. 1, 1991. FIG. 3H depicts an machine learning pipeline topology exemplary of such modifications. As in EigenFaces, one may determine a feature presentation using an unsupervised method at block 330*a* (e.g., determining the principal components using PCA for each group of facial images associated with one of several individuals). As an unsupervised method, the conventional grouping of FIG. 2A may not typically construe this PCA operation as "training." However, by converting the input data (e.g., facial images) to the new representation (the principal component feature space) at block 330*b* one may create a data structure suitable for the application of subsequent inference methods.

For example, at block 330*c* a new incoming feature vector (a new facial image) may be converted to the unsupervised form (e.g., the principal component feature space) and then a metric (e.g., the distance between each individual's facial image group principal components and the new vector's principal component representation) or other subsequent classifier (e.g., an SVM, etc.) applied at block 330*d* to classify the new input. Thus, a model architecture (e.g., PCA) not amenable to the methods of certain methodologies (e.g., metric based training and inference) may be made so amenable via method or architecture modifications, such as pipelining. Again, one will appreciate that this pipeline is but one example—the KNN unsupervised architecture and method of FIG. 2B may similarly be used for supervised classification by assigning a new inference input to the class of the group with the closest first moment in the feature space to the inference input. Thus, these pipelining approaches may be considered machine learning models herein, though they may not be conventionally referred to as such.

Figure 4A:
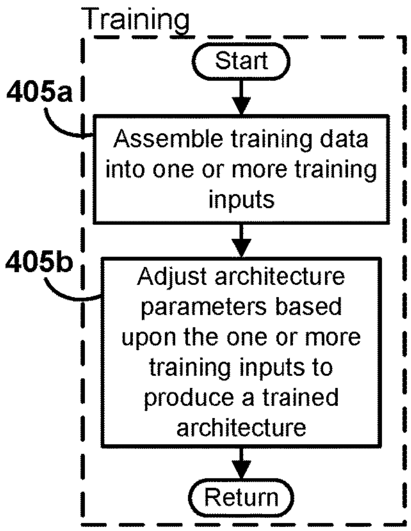
FIG. 4A is a schematic flow diagram depicting various operations common to a variety of machine learning model training methods.

Some architectures may be used with training methods and some of these trained architectures may then be used with inference methods. However, one will appreciate that not all inference methods perform classification and not all trained models may be used for inference. Similarly, one will appreciate that not all inference methods require that a training method be previously applied to the architecture to process a new input for a given task (e.g., as when KNN produces classes from direct consideration of the input data). With regard to training methods, FIG. 4A is a schematic flow diagram depicting common operations in various training methods. Specifically, at block 405*a*, either the practitioner directly or the architecture may assemble the training data into one or more training input feature vectors. For example, the user may collect images of dogs and cats with metadata labels for a supervised learning method or unlabeled stock prices over time for unsupervised clustering. As discussed, the raw data may be converted to a feature vector via preprocessing or may be taken directly as features in its raw form.

At block 405*b*, the training method may adjust the architecture's parameters based upon the training data. For example, the weights and biases of a neural network may be updated via backpropagation, an SVM may select support vectors based on hyperplane calculations, etc. One will appreciate, as was discussed with respect to pipeline architectures in FIG. 3G, however, that not all model architectures may update parameters within the architecture itself during "training." For example, in Eigenfaces the determination of principal components for facial identity groups may be construed as the creation of a new parameter (a principal component feature space), rather than as the adjustment of an existing parameter (e.g., adjusting the weights and biases of a neural network architecture). Accordingly, herein, the Eigenfaces determination of principal components from the training images would still be construed as a training method.

Figure 4B:
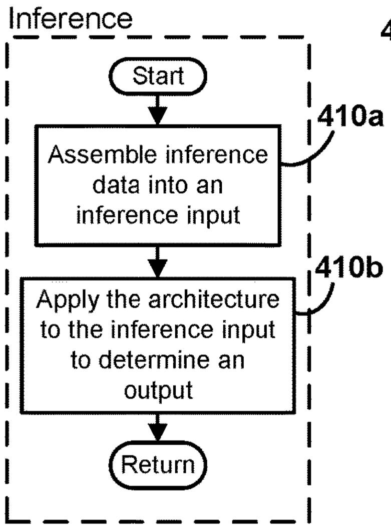
FIG. 4B is a schematic flow diagram depicting various operations common to a variety of machine learning model inference methods.

FIG. 4B is a schematic flow diagram depicting various operations common to a variety of machine learning model inference methods. As mentioned not all architectures nor all methods may include inference functionality. Where an inference method is applicable, at block 410*a* the practitioner or the architecture may assemble the raw inference data, e.g., a new image to be classified, into an inference input feature vector, tensor, etc. (e.g., in the same feature input form as the training data). At block 410*b*, the system may apply the trained architecture to the input inference feature vector to determine an output, e.g., a classification, a regression result, etc.

When "training," some methods and some architectures may consider the input training feature data in whole, in a single pass, or iteratively. For example, decomposition via PCA may be implemented as a non-iterative matrix operation in some implementations. An SVM, depending upon its implementation, may be trained by a single iteration through the inputs. Finally, some neural network implementations may be trained by multiple iterations over the input vectors during gradient descent.

Figure 4C:
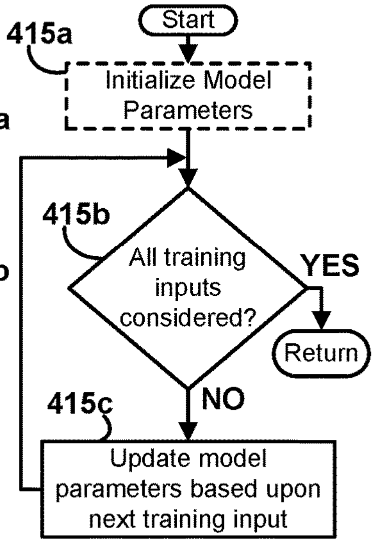
FIG. 4C is a schematic flow diagram depicting various iterative training operations occurring at block 405*b* in some architectures and training methods.

As regards iterative training methods, FIG. 4C is a schematic flow diagram depicting iterative training operations, e.g., as may occur in block 405*b* in some architectures and methods. A single iteration may apply the method in the flow diagram once, whereas an implementation performing multiple iterations may apply the method in the diagram multiple times. At block 415*a*, the architecture's parameters may be initialized to default values. For example, in some neural networks, the weights and biases may be initialized to random values. In some SVM architectures, e.g., in contrast, the operation of block 415*a* may not apply. As each of the training input feature vectors are considered at block 415*b*, the system may update the model's parameters at 415*c*. For example, an SVM training method may or may not select a new hyperplane as new input feature vectors are considered and determined to affect or not to affect support vector selection. Similarly, a neural network method may, e.g., update its weights and biases in accordance with backpropagation and gradient descent. When all the input feature vectors are considered, the model may be considered "trained" if the training method called for only a single iteration to be performed. Methods calling for multiple iterations may apply the operations of FIG. 4C again (naturally, eschewing again initializing at block 415*a* in favor of the parameter values determined in the previous iteration) and complete training when a condition has been met, e.g., an error rate between predicted labels and metadata labels is reduced below a threshold.

Figure 4D:
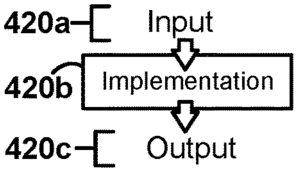
FIG. 4D is a schematic block diagram depicting various machine learning method operations lacking rigid distinctions between training and inference methods.
Figure 4E:
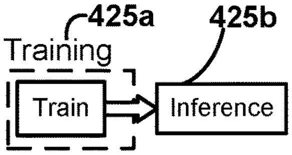
FIG. 4E is a schematic block diagram depicting an example relationship between architecture training methods and inference methods.

As mentioned, the wide variety of machine learning architectures and methods include those with explicit training and inference steps, as shown in FIG. 4E, and those without, as generalized in FIG. 4D. FIG. 4E depicts, e.g., a method training 425*a* a neural network architecture to recognize a newly received image at inference 425*b*, while FIG. 4D depicts, e.g., an implementation reducing data dimensions via PCA or performing KNN clustering, wherein the implementation 420*b* receives an input 420*a* and produces an output 420*c*. For clarity, one will appreciate that while some implementations may receive a data input and produce an output (e.g., an SVM architecture with an inference method), some implementations may only receive a data input (e.g., an SVM architecture with a training method), and some implementations may only produce an output without receiving a data input (e.g., a trained GAN architecture with a random generator method for producing new data instances).

Figure 4F:
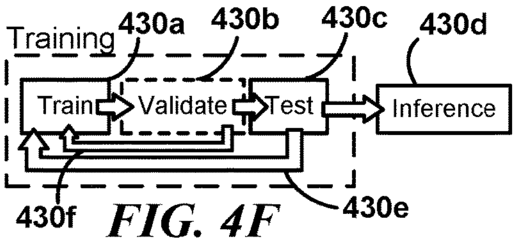
FIG. 4F is a schematic block diagram depicting an example relationship between machine learning model training methods and inference methods, wherein the training methods comprise various data subset operations.
Figure 4G:
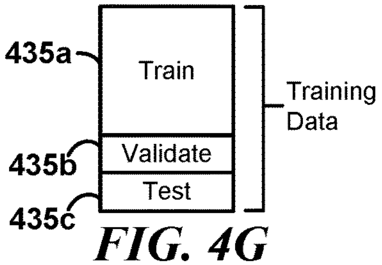
FIG. 4G is a schematic block diagram depicting an example decomposition of training data into a training subset, a validation subset, and a testing subset.
Figure 4H:
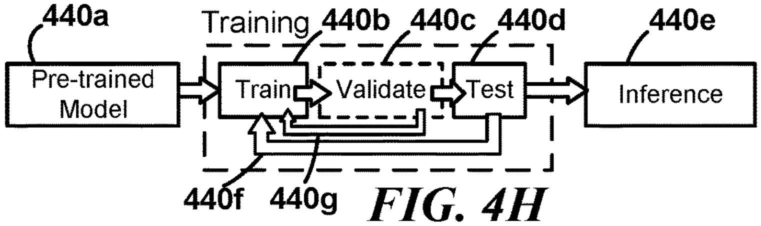
FIG. 4H is a schematic block diagram depicting various operations in a training method incorporating transfer learning.
Figure 4I:
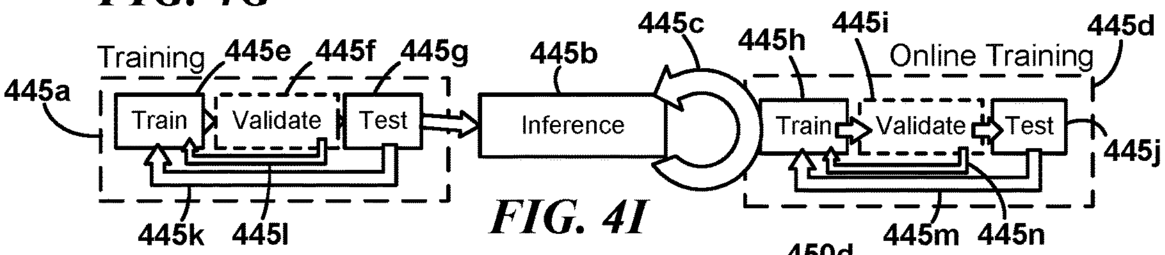
FIG. 4I is a schematic block diagram depicting various operations in a training method incorporating online learning.

The operations of FIGS. 4D and 4E may be further expanded in some methods. For example, some methods expand training as depicted in the schematic diagram of FIG. 4F, wherein the training method further comprises various data subset operations. As shown in FIG. 4G, some training methods may divide the training data into a training data subset, 435*a*, a validation data subset 435*b*, and a test data subset 435*c*. When training the network at block 430*a* as shown in FIG. 4F, the training method may first iteratively adjust the network's parameters using, e.g., backpropagation based upon all or a portion of the training data subset 435*a*. However, at block 430*b*, the subset portion of the data reserved for validation 435*b*, may be used to assess the effectiveness of the training. Not all training methods and architectures are guaranteed to find optimal architecture parameter or configurations for a given task, e.g., they may become stuck in local minima, may employ inefficient learning step size hyperparameter, etc. Methods may validate a current hyperparameter configuration at block 430*b* with training data 435*b* different from the training data subset 435*a* anticipating such defects and adjust the architecture hyperparameters or parameters accordingly. In some methods, the method may iterate between training and validation as shown by the arrow 430*f*, using the validation feedback to continue training on the remainder of training data subset 435*a*, restarting training on all or portion of training data subset 435*a*, adjusting the architecture's hyperparameters or the architecture's topology (as when additional hidden layers may be added to a neural network in meta-learning), etc. Once the architecture has been trained, the method may assess the architecture's effectiveness by applying the architecture to all or a portion of the test data subsets 435*c*. The use of different data subsets for validation and testing may also help avoid overfitting, wherein the training method tailors the architecture's parameters too closely to the training data, mitigating more optimal generalization once the architecture encounters new inference inputs. If the test results are undesirable, the method may start training again with a different parameter configuration, an architecture with a different hyperparameter configuration, etc., as indicated by arrow 430*e*. Testing at block 430*c* may be used to confirm the effectiveness of the trained architecture. Once the model is trained, inference 430*d* may be performed on a newly received inference input. One will appreciate the existence of variations to this validation method, as when, e.g., a method performs a grid search of a space of possible hyperparameters to determine a most suitable architecture for a task.

Many architectures and methods may be modified to integrate with other architectures and methods. For example, some architectures successfully trained for one task may be more effectively trained for a similar task rather than beginning with, e.g., randomly initialized parameters. Methods and architecture employing parameters from a first architecture in a second architecture (in some instances, the architectures may be the same) are referred to as "transfer learning" methods and architectures. Given a pre-trained architecture 440*a* (e.g., a deep learning architecture trained to recognize birds in images), transfer learning methods may perform additional training with data from a new task domain (e.g., providing labeled data of images of cars to recognize cars in images) so that inference 440*e* may be performed in this new task domain. The transfer learning training method may or may not distinguish training 440*b*, validation 440*c*, and test 440*d* sub-methods and data subsets as described above, as well as the iterative operations 440*f* and 440*g*. One will appreciate that the pre-trained model 440*a* may be received as an entire trained architecture, or, e.g., as a list of the trained parameter values to be applied to a parallel instance of the same or similar architecture. In some transfer learning applications, some parameters of the pre-trained architecture may be "frozen" to prevent their adjustment during training, while other parameters are allowed to vary during training with data from the new domain. This approach may retain the general benefits of the architecture's original training, while tailoring the architecture to the new domain.

Combinations of architectures and methods may also be extended in time. For example, "online learning" methods anticipate application of an initial training method 445*a* to an architecture, the subsequent application of an inference method with that trained architecture 445*b*, as well as periodic updates 445*c* by applying another training method 445*d*, possibly the same method as method 445*a*, but typically to new training data inputs. Online learning methods may be useful, e.g., where a robot is deployed to a remote environment following the initial training method 445*a* where it may encounter additional data that may improve application of the inference method at 445*b*. For example, where several robots are deployed in this manner, as one robot encounters "true positive" recognition (e.g., new core samples with classifications validated by a geologist; new patient characteristics during a surgery validated by the operating surgeon), the robot may transmit that data and result as new training data inputs to its peer robots for use with the method 445*d*. A neural network may perform a backpropagation adjustment using the true positive data at training method 445*d*. Similarly, an SVM may consider whether the new data affects its support vector selection, precipitating adjustment of its hyperplane, at training method 445*d*. While online learning is frequently part of reinforcement learning, online learning may also appear in other methods, such as classification, regression, clustering, etc. Initial training methods may or may not include training 445*e*, validation 445*f*, and testing 445*g* sub-methods, and iterative adjustments 445*k*, 445*l* at training method 445*a*. Similarly, online training may or may not include training 445*h*, validation 445*i*, and testing sub-methods, 445*j* and iterative adjustments 445*m* and 445*n*, and if included, may be different from the sub-methods 445*e*, 445*f*, 445*g* and iterative adjustments 445*k*, 445*l*. Indeed, the subsets and ratios of the training data allocated for validation and testing may be different at each training method 445*a* and 445*d*.

Figure 4J:
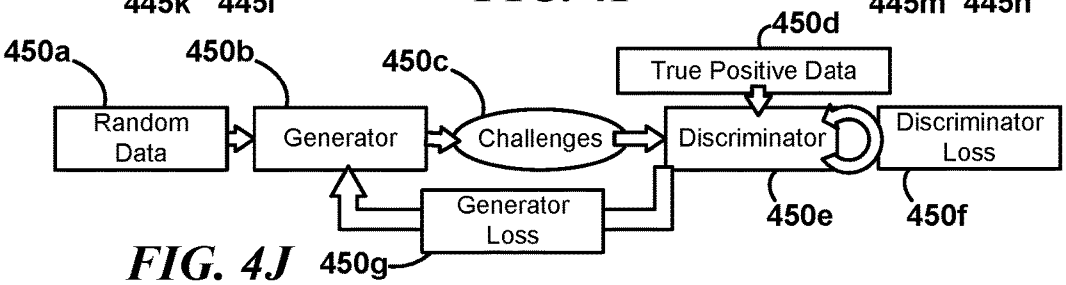
FIG. 4J is a schematic block diagram depicting various components in an example generative adversarial network method.

As discussed above, many machine learning architectures and methods need not be used exclusively for any one task, such as training, clustering, inference, etc. FIG. 4J depicts one such example GAN architecture and method. In GAN architectures, a generator sub-architecture 450*b* may interact competitively with a discriminator sub-architecture 450*e*. For example, the generator sub-architecture 450*b* may be trained to produce, synthetic "fake" challenges 450*c*, such as synthetic portraits of non-existent individuals, in parallel with a discriminator sub-architecture 450*e* being trained to distinguish the "fake" challenge from real, true positive data 450*d*, e.g., genuine portraits of real people. Such methods can be used to generate, e.g., synthetic assets resembling real-world data, for use, e.g., as additional training data. Initially, the generator sub-architecture 450*b* may be initialized with random data 450*a* and parameter values, precipitating very unconvincing challenges 450*c*. The discriminator sub-architecture 450*e* may be initially trained with true positive data 450*d* and so may initially easily distinguish fake challenges 450*c*. With each training cycle, however, the generator's loss 450*g* may be used to improve the generator sub-architecture's 450*b* training and the discriminator's loss 450*f* may be used to improve the discriminator sub-architecture's 450*e* training. Such competitive training may ultimately produce synthetic challenges 450*c* very difficult to distinguish from true positive data 450*d*. For clarity, one will appreciate that an "adversarial" network in the context of a GAN refers to the competition of generators and discriminators described above, whereas an "adversarial" input instead refers an input specifically designed to effect a particular output in an implementation, possibly an output unintended by the implementation's designer.

Data Overview

FIG. 5A is a schematic illustration of surgical data as may be received at a processing system in some embodiments. Specifically, a processing system may receive raw data 510, such as video from a visualization tool 110*b* or 140*d* comprising a succession of individual frames over time 505. In some embodiments, the raw data 510 may include video and system data from multiple surgical operations 510*a*, 510*b*, 510*c*, or only a single surgical operation.

As mentioned, each surgical operation may include groups of actions, each group forming a discrete unit referred to herein as a task. For example, surgical operation 510*b* may include tasks 515*a*, 515*b*, 515*c*, and 515*e* (ellipses 515*d* indicating that there may be more intervening tasks). Note that some tasks may be repeated in an operation or their order may change. For example, task 515*a* may involve locating a segment of fascia, task 515*b* involves dissecting a first portion of the fascia, task 515*c* involves dissecting a second portion of the fascia, and task 515*e* involves cleaning and cauterizing regions of the fascia prior to closure.

Each of the tasks 515 may be associated with a corresponding set of frames 520*a*, 520*b*, 520*c*, and 520*d* and device datasets including operator kinematics data 525*a*, 525*b*, 525*c*, 525*d*, patient-side device data 530*a*, 530*b*, 530*c*, 530*d*, and system events data 535*a*, 535*b*, 535*c*, 535*d*. For example, for video acquired from visualization tool 140*d* in theater 100*b*, operator-side kinematics data 525 may include translation and rotation values for one or more hand-held input mechanisms 160*b* at surgeon console 155. Similarly, patient-side kinematics data 530 may include data from patient side cart 130, from sensors located on one or more tools 140*a-d*, 110*a*, rotation and translation data from arms 135*a*, 135*b*, 135*c*, and 135*d*, etc. System events data 535 may include data for parameters taking on discrete values, such as activation of one or more of pedals 160*c*, activation of a tool, activation of a system alarm, energy applications, button presses, camera movement, etc. In some situations, task data may include one or more of frame sets 520, operator-side kinematics 525, patient-side kinematics 530, and system events 535, rather than all four.

One will appreciate that while, for clarity and to facilitate comprehension, kinematics data is shown herein as a waveform and system data as successive state vectors, one will appreciate that some kinematics data may assume discrete values over time (e.g., an encoder measuring a continuous component position may be sampled at fixed intervals) and, conversely, some system values may assume continuous values over time (e.g., values may be interpolated, as when a parametric function may be fitted to individually sampled values of a temperature sensor).

In addition, while surgeries 510*a*, 510*b*, 510*c* and tasks 515*a*, 515*b*, 515*c* are shown here as being immediately adjacent so as to facilitate understanding, one will appreciate that there may be gaps between surgeries and tasks in real-world surgical video. Accordingly, some video and data may be unaffiliated with a task. In some embodiments, these non-task regions may themselves be denoted as tasks, e.g., "gap" tasks, wherein no "genuine" task occurs.

The discrete set of frames associated with a task may be determined by the tasks' start point and end point. Each start point and each endpoint may be itself determined by either a tool action or a tool-effected change of state in the body. Thus, data acquired between these two events may be associated with the task. For example, start and end point actions for task 515*b* may occur at timestamps associated with locations 550*a* and 550*b* respectively.

FIG. 5B is a table depicting example tasks with their corresponding start point and end points as may be used in conjunction with various disclosed embodiments. Specifically, data associated with the task "Mobilize Colon" is the data acquired between the time when a tool first interacts with the colon or surrounding tissue and the time when a tool last interacts with the colon or surrounding tissue. Thus any of frame sets 520, operator-side kinematics 525, patient-side kinematics 530, and system events 535 with timestamps between this start and end point are data associated with the task "Mobilize Colon". Similarly, data associated the task "Endopelvic Fascia Dissection" is the data acquired between the time when a tool first interacts with the endopelvic fascia (EPF) and the timestamp of the last interaction with the EPF after the prostate is defatted and separated. Data associated with the task "Apical Dissection" corresponds to the data acquired between the time when a tool first interacts with tissue at the prostate and ends when the prostate has been freed from all attachments to the patient's body. One will appreciate that task start and end times may be chosen to allow temporal overlap between tasks, or may be chosen to avoid such temporal overlaps. For example, in some embodiments, tasks may be "paused" as when a surgeon engaged in a first task transitions to a second task before completing the first task, completes the second task, then returns to and completes the first task. Accordingly, while start and end points may define task boundaries, one will appreciate that data may be annotated to reflect timestamps affiliated with more than one task.

Additional examples of tasks include a "2-Hand Suture", which involves completing 4 horizontal interrupted sutures using a two-handed technique (i.e., the start time is when the suturing needle first pierces tissue and the stop time is when the suturing needle exits tissue with only two-hand, e.g., no one-hand suturing actions, occurring in-between). A "Uterine Horn" task includes dissecting a broad ligament from the left and right uterine horns, as well as amputation of the uterine body (one will appreciate that some tasks have more than one condition or event determining their start or end time, as here, when the task starts when the dissection tool contacts either the uterine horns or uterine body and ends when both the uterine horns and body are disconnected from the patient). A "1-Hand Suture" task includes completing four vertical interrupted sutures using a one-handed technique (i.e., the start time is when the suturing needle first pierces tissue and the stop time is when the suturing needle exits tissue with only one-hand, e.g., no two-hand suturing actions occurring in-between). The task "Suspensory Ligaments" includes dissecting lateral leaflets of each suspensory ligament so as to expose ureter (i.e., the start time is when dissection of the first leaflet begins and the stop time is when dissection of the last leaflet completes). The task "Running Suture" includes executing a running suture with four bites (i.e., the start time is when the suturing needle first pierces tissue and the stop time is when the needle exits tissue after completing all four bites). As a final example, the task "Rectal Artery/Vein" includes dissecting and ligating a superior rectal artery and vein (i.e. the start time is when dissection begins upon either the artery or the vein and the stop time is when the surgeon ceases contact with the ligature following ligation).

Example Fields of View in Surgical Data

When one or more of data 520, 525, 530, and 535 are available, they may be useful for data analysis, such as monitoring surgeon performance, as well as training machine learning classifiers for a wide variety of applications. Unfortunately, in its initially acquired form, the visualization tool output in frames 520 may include not only fields of view inside the patient, but external fields of view capturing sensitive or personal information appearing in the surgical theater, such as the faces of team members, identifying features of the patient, etc. Such changes in the visual field may also indicate that data 525, 530, and 535 may no longer bear upon a task in the surgical procedure. Such external field capture may be undesirable as it may present a privacy or security issue, thereby, e.g., limiting accessibility to the output for data analysis purposes. Similarly, the data may be extraneous to downstream processing and its presence therefore represents an undesirable imposition on memory storage and downstream filtering.

Figure 6:
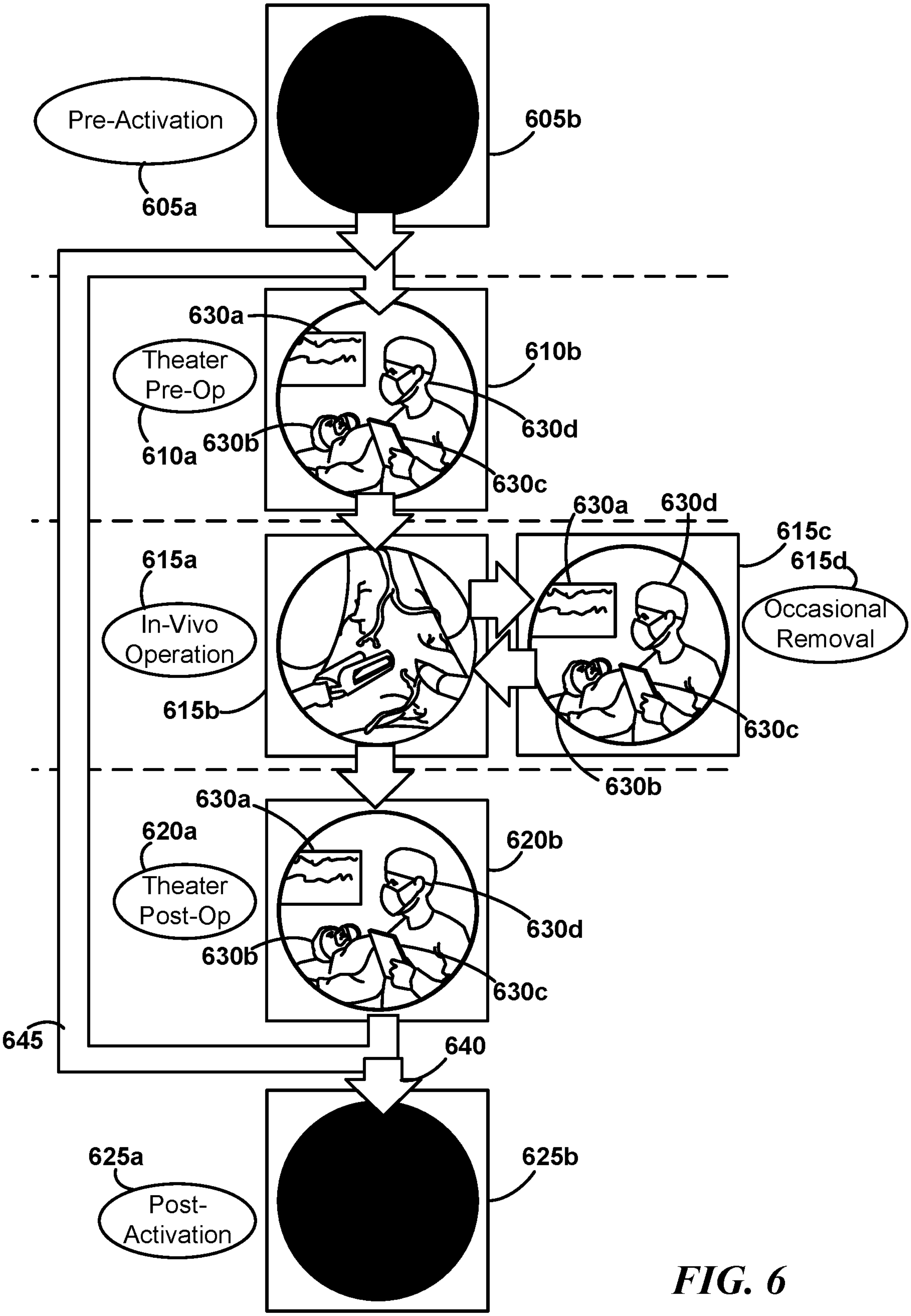
FIG. 6 is a schematic diagram illustrating example stages of visualization tool operation in the surgical theaters of FIGS. 1A and 1B as may occur in some embodiments.

FIG. 6 is a schematic diagram illustrating example stages of output from a visualization tool (e.g., visualization tool 110*b* or visualization tool 140*d*, such as a laparoscopic ultrasound or endoscope) in the surgical theaters of FIGS. 1A and 1B as may occur in some embodiments. As the surgical theater begins operation, a team member may begin recording with visualization tool 110*b* or visualization tool 140*d*, thereby producing an output visualization captured in video regardless of whether the tool is yet inside the patient. Thus, before the surgical theater begins its first operation, the tool may be in a "pre-activation" state 605*a* as when the tool is turned off or turned on, but covered with a protective cap. In this state, the tool's field of view 605*b* and consequently any resulting video output, is unlikely to include any sensitive information. Still, it may be desirable to remove these video frames as they do not depict fields of view relevant to a surgical procedure. Similarly, one may wish to remove data 525, 530, and 535 corresponding to these frames, as it does not yet bear upon a surgical procedure.

During a subsequent "theater pre-op" state 610*a* a team member (e.g., team members 105*b* or 105*d*) may activate the tool, e.g., by removing the tool's cover or supplying power to the tool, prior to the tool's insertion into the patient. Similarly, the tool may have been previously activated, but video recording only began at this time. During this time, the field of view 610*b* may include sensitive information, such as the faces 630*d* or other identifying features of team members, patient-identifying charts 630*c*, patient faces 630*b* or other identifying features, surgery room whiteboards 630*a* with patient information and a surgery schedule, etc. Distributing this information outside the facility in which the surgery was performed may violate contractual or regulatory requirements, e.g., various HIPPA protections. Similar to state 605*a*, one may also wish to ignore data 525, 530, and 535 captured during this period.

Once the surgical operation begins, the tool may enter an "in-vivo operation" state 615*a* wherein its field of view 615*b* depicts generally non-identifying features of the patient's internal anatomy. As mentioned, throughout a surgical operation, various tasks may require removal and/or repositioning of the visualization tools 110*b* or 140*d*. Such adjustments may transition the tool to an "occasional removal" state 615*d*, wherein its field of view 615*c* may again include sensitive information before the tool again returns to an "in-vivo operation" state 615*a*. There are various reasons for removing the tool, e.g., to change the arm the visualization tool is on to get a different view of anatomy, to clean the tip of the scope from a smudge/liquid from surgery, etc. Thus, sometimes tool removals and reinsertions may be expected as part of task operations or transitions, while other times they may be ad hoc, unanticipated events.

When the surgical operation eventually concludes, the visualization tool may be removed in a "theater post-op" state 620*a*, which may again present sensitive information within its field of view 620*b*. If multiple surgeries are performed throughout the course of a video recording (e.g., where the recording was simply taken over the course of a surgical theater's day of operations), the tool may traverse 645 the states 610*a*, 615*a*, 615*d*, 620*a* multiple times before finally being deactivated and entering 640 a "post-activation" state 625*a* once surgeries have completed for the theater (e.g., when a surgical theater concludes its surgeries for the day), which may again depict a blank field of view 625*b*. While video recorded from the output of visualization tool 110*b* or visualization tool 140*d* may generally follow the stages of FIG. 6, one will appreciate that some videos may deviate from this example pattern, e.g., where video terminates prematurely due to a lack of storage during "in-vivo operation" state 615*a*, where administrations edit the video before release, etc.

Naturally, if insertion and removal of a visualization tool is evident from data 525, 530, and 535 recognizing the states of FIG. 6 and making corresponding excisions in the data may be relatively straightforward. Motion of the visualization tool captured in kinematics data or salinity levels captured in events or sensor data may be used to identify which data is associated with "in-vivo operation" state 615*a*. However, many theaters are of the form of theater 100*a* rather than 100*b*, and while both theaters may capture video data, capturing data 525, 530, and 535 in theater 100*a* may be less common. Ideally, therefore, it would be possible to process only video data from both theaters 100*a* and 100*b* to remove non-surgical frames, so that more data may be made available for downstream processing (e.g., some deep learning algorithms benefit from having access to more data). Additionally, by basing censorship upon video only, one may corroborate data 525, 530, and 535 when it is available.

Example Video Content Processing Methodology

Figure 7A:
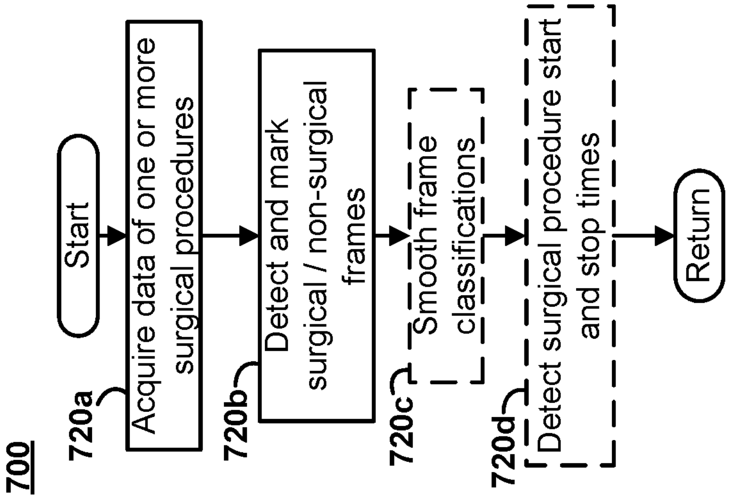
FIG. 7A is a flow diagram illustrating various operations in an surgical video processing method as may be implemented in some embodiments.
Figure 7B:
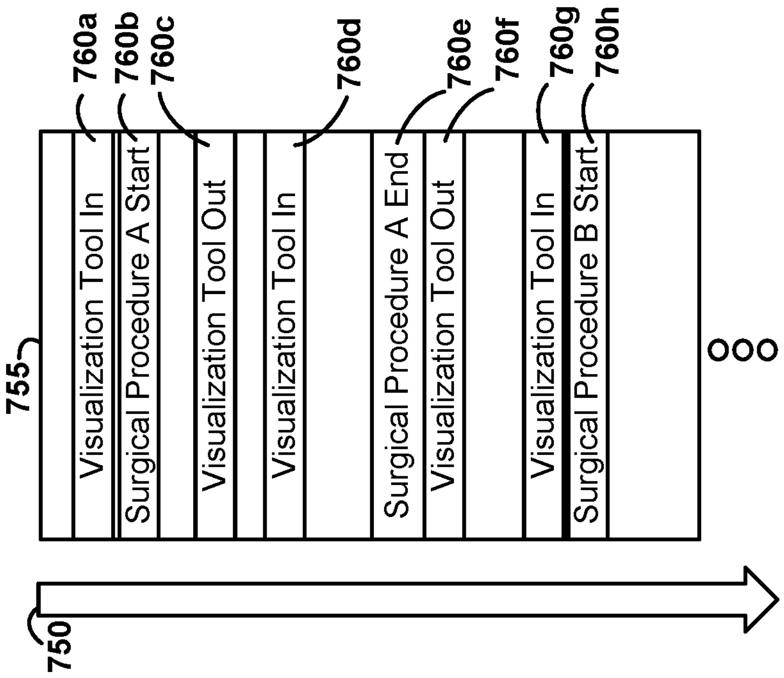
FIG. 7B is a schematic data time series marked with visualization tool state transition events as may occur in some embodiments.

FIG. 7A is a flow diagram illustrating example operations in an surgical video processing method 700 as may be implemented in some embodiments. One will appreciate that not all blocks of the method 700 may be performed by the same processing system or at the same location, though in some embodiments that may be the case. At block 720*a* a processing system may acquire surgical data of one or more surgical procedures from one or more visualization tools. For example, with reference to the schematic data time series of FIG. 7B, as time 750 progresses, corresponding data values may be recorded in dataset 755 (e.g., video frames) during the surgery (one will appreciate that in some instances the video may be compressed and frames will need to be extracted or operated upon mutatis mutandis as described herein). Thus, each datapoint (e.g., video frame) may be associated with a unique timestamp.

At block 720*b*, the system may recognize surgical from non-surgical data, e.g., video frames acquired when the visualization tool was potentially capturing sensitive or irrelevant information in one of states 605*a*, 610*a*, 615*d*, 620*a*, or 625*a* using the systems and methods described herein. For clarity, such recognition may designate the frames before time 760*a*, between times time 760*c* and 760*d*, between times 760*f* and 760*g*, etc. for removal from the dataset.

At block 720*c*, the system may smooth the frame classifications acquired at block 720*b*. For example, if a machine learning classifier was used at block 720*b* to distinguish surgical from non-surgical data, there may be false positive and false negative classifications in the output. Smoothing may help adjust the classifications to compensate for such false positives and false negatives, e.g., where such classifications result in statistically improbable lengths of surgical or non-surgical data.

At block 720*d*, the processing system may then use the frame classifications and corresponding timestamps to infer when surgical procedures begin and end (e.g., times 760*b* and 760*e*, 760*h*, etc.). One will appreciate that this may not be necessary where only a single surgical procedure was provided at block 720*a* or where the recognition is being performed at real-time as a surgery progresses. One will also appreciate that where a video concludes with a surgery start time lacking a corresponding surgery stop time, the end of the video may be taken as the surgery's stop time in some embodiments. Knowing when surgeries begin and end within the dataset 755 may facilitate segregating the single data capture into multiple component segments, each segment depicting an individual surgical operation. These segments may then be output for subsequent processing, such as human-based annotation or machine learning analysis upon the individual surgical segments.

Example Video Content Processing System Component Topology

Figure 8:
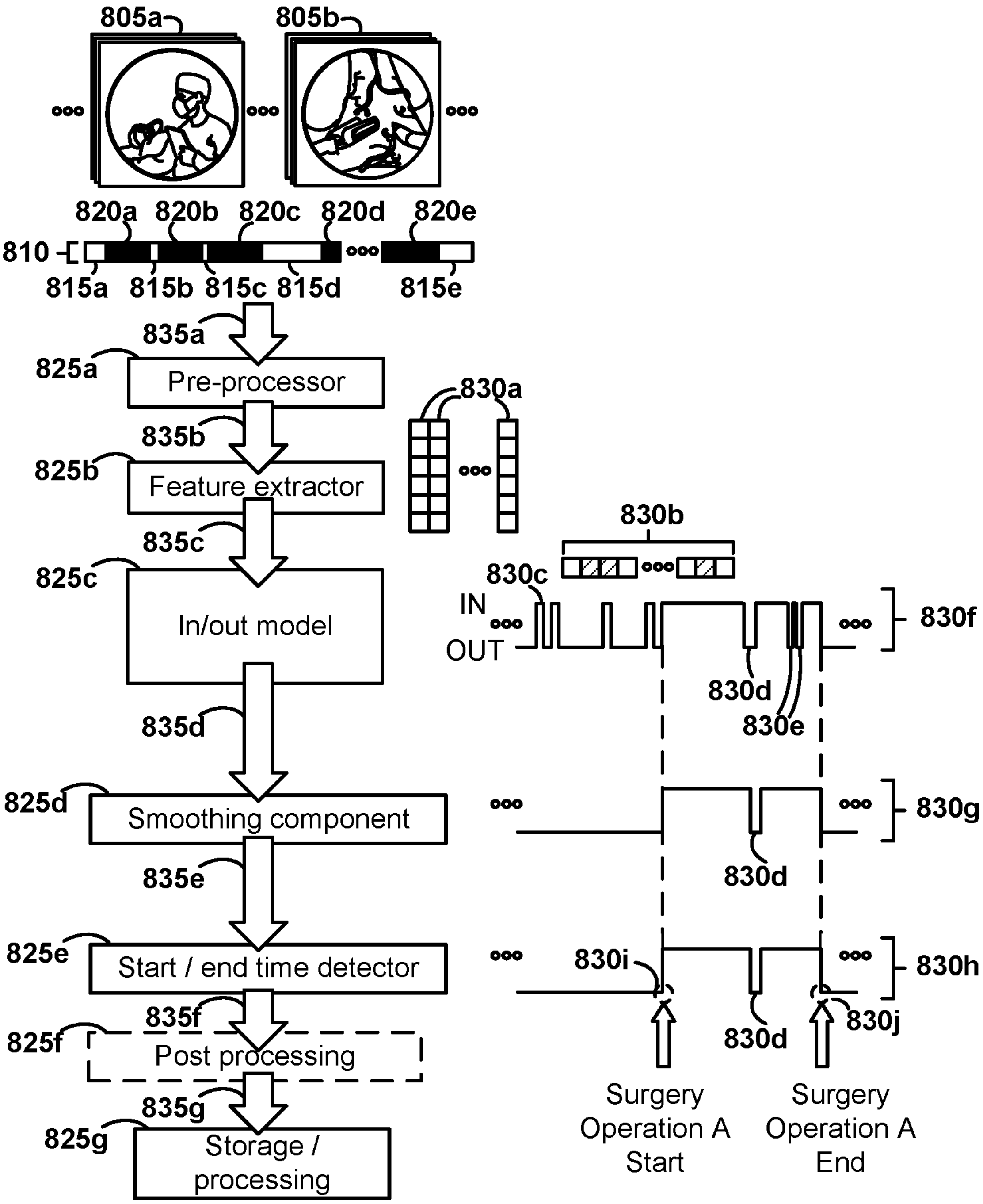
FIG. 8 is a schematic block diagram illustrating components of a surgical procedure video filtering system operating in accordance with the method of FIG. 7A, as may be implemented in some embodiments.

To facilitate comprehension of the method of FIG. 7A in greater detail, FIG. 8 is a schematic diagram illustrating components of a surgical procedure video filtering system operating in accordance with the method of FIG. 7A, as may be implemented in some embodiments. One will appreciate that the surgical video procedure filtering system may include multiple component processing systems, which may themselves be distinct software, hardware, or firmware implementations. As will be discussed, these component systems may not be collocated at the same location and may be directed to distinct functions. Thus, two components may be different lines of software run on a same or different computer systems, different hardware, firmware, etc.

A processing system may receive or operate in real-time upon surgical dataset 810 comprising at least video frames 805*a*, 805*b* having portions 820*a*, 820*b*, 820*c*, 820*d*, 820*e* depicting fields of view inside the patient and portions 815*a*, 815*b*, 815*c*, 815*d*, 815*e* depicting fields of view outside the patient. Initially, a pre-processor component 825*a* may receive the dataset 810 for processing. Pre-processor component 825*a* may down-sample the dataset to facilitate downstream analysis, convert data to a more suitable form (as when video is captured in a compressed form and will be converted to discrete frames by the pre-processor), decrypt the data if it is encrypted, etc. As visualization tools or recording devices may capture video at a much higher framerate than is required for distinguishing portions of the dataset associated with fields of view inside or outside the patient, down-sampling may conserve computational resources. Such conservation may be especially useful where the subsequent components operate in environments with limited memory or processing power, or where the recognition is being performed in real-time during the surgery and being communicated to components in the cloud over a network with nontrivial latency.

In some embodiments, if dataset 810 includes system events or kinematics data clearly indicating surgical or non-surgical portions, pre-processor component 825*a* may classify frames prior to their submission to a more sophisticated video-based algorithm so as to conserve computational resources. Similarly, portions of the dataset may be quickly categorized where the state is easily perceived from the video (e.g., where the video frame depicts "pre-activation" state 605*a* and is entirely black, or where a user interface displayed in a GUI in the frame indicates the visualization tool's location inside or outside the patient) or from meta-data accompanying the video (e.g., manual annotations by members of the surgical team indicating when operations concluded).

Often, though, dataset 810 will include only video data. Pre-processor component 825*a* may provide the down sampled data to a feature extractor component 825*b*, which may generate features 830*a* from the frames. Though features 830*a* are represented here as linear vectors of values, one will appreciate that features may take nonlinear forms. Indeed, the same data may be reformatted into linear or nonlinear forms as when an RGB 64×64 pixel image is represented either as a linear vector of 12,288 values or as a tensor of dimensions 3×64×64. Thus, for example, where the data is video frames only, each feature vector may be pixel values associated with a single frame (though in some embodiments frames may be color shifted, compressed, reduced via PCA, etc.). In some embodiments, where dataset 810 includes event or kinematics data (though, again, this often won't be the case), feature extractor component 825*b* may append discrete values derived from such data to a linear representation of video frame pixel vector (or other suitable representation) to assist downstream machine learning models with recognition (where such models are configured to receive such data).

Feature extractor component 825*b* may pass the generated feature vectors 830*a* to a machine learning model 825*c* for initial classification. For example, the model may receive one or more video frames and output a classification value (e.g., "inside the patient" or "outside the patient/irrelevant data"). Such an output may take the form of an array 830*b*, each value representing a classification result for a corresponding frame. One will appreciate that such an array may be formed in some embodiments by applying successive frames to the model in temporal order and appending the resulting outputs.

Such binary results may also be represented herein by a waveform 830*f* (naturally, while a continuous waveform is shown here to facilitate understanding, one will appreciate that classifications may be applied to discrete video frames in practice) illustrating how, as time passes from left to right, the classification values for the corresponding data in time may take on inside or outside values. As indicated in the example waveform 830*f*, the model may not provide perfect classifications, resulting in either false positive or false negative classifications. For example, the inside interval 830*c* may be too short to be reasonably construed as a genuine datapoint inside the patient (indeed, some such intervals precipitated by model misclassifications may be so short as to be physically impossible). Similarly, the datapoints 830*e* may be too short to be reasonably construed as reflecting removal of the tool from the patient. In contrast some intervals, such as interval 830*d* may be long enough that they might reasonably reflect either a genuine tool removal and reinsertion during a surgery or, typically if longer, an interval occurring between surgeries.

Model component 825*c* may pass the results represented in waveform 830*f* to a smoothing component system 825*d*. In some embodiments, model component 825*c* and smoothing component system 825*d* may be on the same system. However, as mentioned, one will appreciate that a smoothing component system may not be co-located with model component 825*c*. Thus, encryption/decryption may be performed when moving the results at each of arrows 835*a*, 835*b*, 835*c*, 835*d*, 835*e*, 835*f*, and 835*g* as the data may still include sensitive information (while tentative classifications are present, actual excision of data based upon the classification may not occur until later in some embodiments).

Smoothing component 825*d* may "smooth" the classification values, remove the false positives and false negatives reflected by regions 830*c* and 830*e* discussed above. For example, smoothing component 825*d* may apply a temporal window (e.g., a kernel filter) as discussed elsewhere herein to the dataset, removing regions too small to agree with expected in/out durations. This may result in a "clean" dataset, presented by waveform 830*g*. Note that the genuine removal region 830*d* may be retained following smoothing.

Smoothing component 825*d* may provide these cleaned classification results to start/end time detection component 825*e*. In some embodiments, frames classified as being outside the patient may be whitened out (data replaced with zero values) or excised to, e.g., comply with regulatory requirements. Following such an operation, it may be feasible to move the data to another location, e.g., a location where start/end detector component 825*e* may be located. Often, however, smoothing component 825*d* and start/stop detector component 825*e* may be collocated and may, indeed, be distinct blocks of software running on a same computer system (e.g., a same computer system containing all of the previous components discussed in other corresponding software code blocks).

Start/end time detector component 825*e* may assess the intervals involved as discussed elsewhere herein to discern where surgical operations begin and end. For example, start/end time detector component 825*e* may generate start/stop time annotated data 830*h* by determining a time 830*i* as the beginning of a new surgical procedure and a time 830*j* as the end of the surgical procedure based upon the length of the preceding and succeeding "out" intervals. Note that genuine "out" region 830*d* would still remain as an "out" interval within the surgery (and may, accordingly, be excised or whited out). Again, one will appreciate that when filtering is being applied to real-time data during surgery, start/end time detector component 825*e* may be absent or disabled.

In some embodiments, start/end time detector component 825*e* may provide the results to a post-processing component 825*f*. For example, post-processing component 825*f* may white out, blur, or excise the data, or divide the data into distinct segments, etc. (e.g., for both inter-surgery regions of data, as well as genuine "out" region 830*d*) as suitable for downstream processing. Such downstream systems may access the data output where it is stored in a storage processing component 825*g*, such as a cloud-based network server.

One will appreciate that while each of the arrows 835*a*, 835*b*, 835*c*, 835*d*, 835*e*, 835*f*, 835*g*, reflect the movement of results or data from one component to another, since the components may not be collocated, each arrow may also reflect encryption and decryption of the data or results. After the "non-surgical" data has been whited out or excised, however, encryption may no longer be necessary. Conversely, in some embodiments, all the components will reside on one computer system (e.g., each component is a separate block of code run by a same computer system). In this situation, as well, encryption may not be needed to comply with regulatory requirements. Indeed, where excision is successful, no encryption may be needed, as any data leaving a controlled environment will already have its non-surgical data removed.

Example Machine Learning Recognition System

Figure 9A:
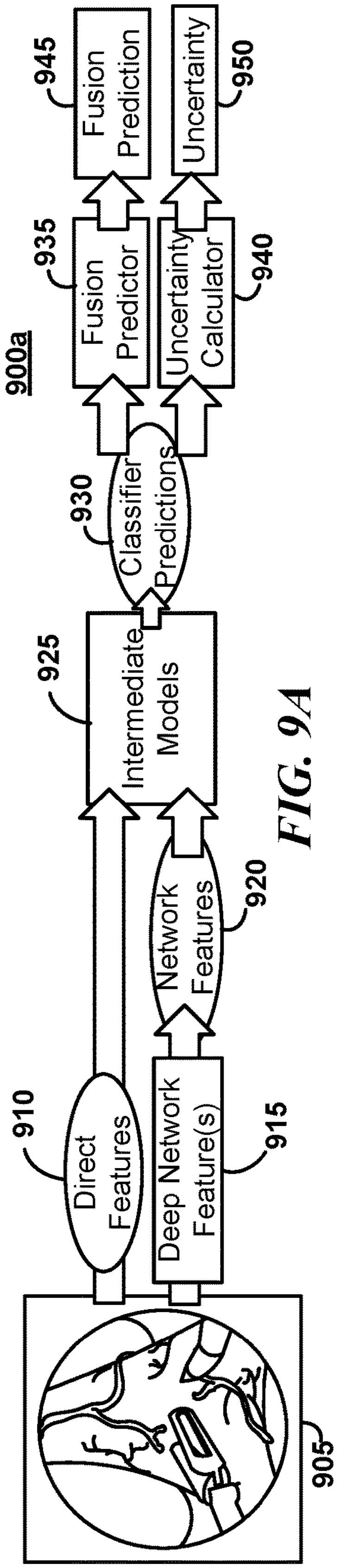
FIG. 9A is a schematic ensemble machine learning model topology diagram depicting a model topology as may be implemented in some embodiments to determine whether a visualization tool video frame depicts a view inside or outside a patient's body.

FIG. 9A is an example schematic ensemble machine learning model topology 900*a* as may be implemented in some embodiments to determine whether a visualization tool video frame depicts a view inside or outside a patient's body. Given a frame of video 905 a processing system may generate "direct features" 910 by applying logical operations (e.g., computer code) to the frame itself and may generate "network features" 920 by providing the video frame to one or more deep learning networks 915. Both the direct features 910 and network features 920 may then be provided to one or more machine learning classifiers 925 to produce one or more predicted classifications 930 whether the frame depicts a field of view inside or outside the patient. One will appreciate that deep learning networks 915 may be used in their pretrained form (even if upon a dataset unrelated to surgery, such as the ImageNet or the Common Objects in Context Dataset). However, in some embodiments, transfer learning may be applied, as when layers other than their final head layers of the network may be frozen (i.e., freeze the "Feature Extraction" layers of FIG. 3F) and the models trained (i.e., the weights in the head layers, the layers in "Classification" of FIG. 3F, allowed to vary) to recognize in and out frames prior to the network's incorporation into the model.

These predicted classifications 930 may then each be considered by a fusion predictor 935 (e.g., a fusion machine learning model or fusion logic, such as majority voting logic) and an uncertainty calculator 940 to produce a fused field of view prediction for the frame 945 and an uncertainty measure 950 of the prediction, respectively. As discussed elsewhere herein, one will appreciate that in lieu of an uncertainty calculator 940 as applied, e.g., to discriminative classifier model 925, a generative model 920 may be substituted and uncertainty determined, e.g., based upon the variance of the probability distribution output by the generative classifier. In some embodiments, separate classifiers may be used, e.g., a discriminative classifier for the prediction fusion value 945 and a separate generative classifier for determining uncertainty 950.

Figure 9B:
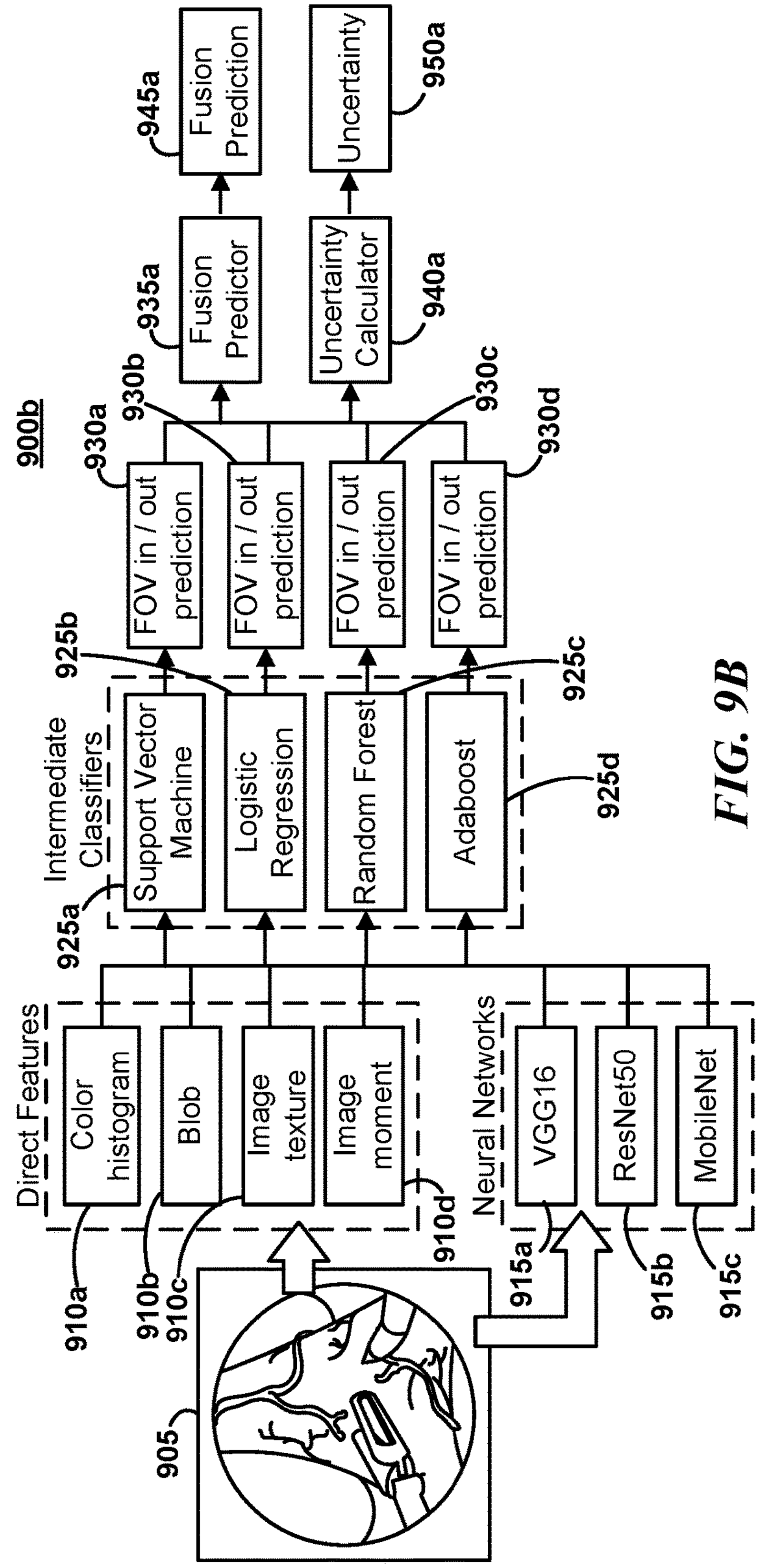
FIG. 9B is schematic topology diagram indicating an example selection of model architectures and features which may be used in the schematic ensemble machine learning model topology of FIG. 9A in some embodiments.

To facilitate the reader's appreciation of topologies that may be implemented in accordance with FIG. 9A, FIG. 9B is an example selection of models which may be used in the schematic ensemble machine learning model topology of FIG. 9A in some embodiments. Particularly, this instantiation may produce a color histogram 910*a* feature, a color blob 910*b* feature, an image texture 910*c* feature, and an image moment feature 910*d* directly from the image 905. Experimentation has demonstrated that choosing one or more of these features may facilitate classifiers generalizable across a wide range of surgical procedures in some embodiments.

Color histogram feature 910*a* may represent colors appearing in an image in a manner invariant to small changes of camera viewpoints. For example, the system may extract an HSV color space histogram with an 8×8 bin size for each HSV color channel. One will appreciate that many libraries, such as OpenCV™, provide such functionality, e.g., one example histogram calculation is evidenced by code line listings C1 and C2:

```
image=cv2.cvtColor (img, cv2.COLOR_RGB2HSV)        (C1)

hist=cv2.calcHist ([image], [0, 1, 2], None, [bins,
    bins, bins], [0, 256,0, 256, 0, 2561)         (C2)
```

where line C1 converts the image to an appropriate form, "img" is the image 905, "[0, 1, 2]" are the channels to be considered, "bins" are ranges of values to be grouped together in the histogram, and "[0, 256,0, 256, 0, 256]" are the ranges used.

Color blob feature 910*b* may reflect brightness or color compared to surrounding pixels. For example, color blob feature 910*b* may be the Determinant of Hessian (DoH) approach for detecting blobs, wherein central points and volume of detected blobs are used as a measure. One may also determine such dark/bright regions in an image by using the Laplacian of Gaussian, difference of Gaussians, difference of Hessians approach, etc. on each color channel of the image. The output for each channel may be a list of x,y positions of blobs of specific sizes. This output may be truncated to include only a threshold (e.g. 100) of the largest blobs in each color channel. For example, one may use the skimage.feature.blob_doh function from the library Scikit-image™ as shown in code line listing C3:

```
blobs_doh=blob_doh(img,max_sigma=30,thresh-
    old=0.01)                                      (C3)
```

Image texture feature 910*c* may reflect the spatial variations of pixel intensities in the image, indicating, e.g., the consistency of repeated patterns on an object's surface. In some embodiments, the texture descriptors may be those proposed by Haralick and Shanmugan, a set of one or more of 13 characteristic parameters calculated based upon the gray-level co-occurrence matrix of the image. Tissue and instrument texture features may be very different from features generated from the "textures" appearing within the visualization tool's field of view when the tool is withdrawn from the patient. One may use, e.g., the Scikit-image™ greycomatrix, greycoprops functions for this purpose, e.g., given a "patch" of the image as shown in code line listing C4:

```
glcm=greycomatrix(patch,distances=[5],angles=[0],
    levels=256,symmetric=True,normed=True)        (C4)
```

Image moment feature 910*d* may be a weighted average of image pixel intensities, thereby capturing information regarding the shape of blobs in the image. Some embodiments employ Hu moment invariants for this purpose, calculating the first seven most significant moments. As Hu moments are invariant to image transformations with respect to translation, scaling, as well as rotation, they may provide a useful generic representation of objects regardless of orientation. One will appreciate that many libraries facilitate the calculation of such moments, e.g., the HuMoments function of the OpenCV™ library as shown in code line listing C5, as applied to the image "img":

```
imu_hu_moment=cv2.HuMoments(cv2.moments
    (img))        (C5)
```

One will appreciate that one may readily create "fused" combinations of the above features 910*a*, 910*b*, 910*c*, 910*d* by concatenating (or otherwise combining) various of their outputs.

The image 905 may also be fed as input to pre-trained implementations of various neural networks, such as the VGG16 network 915*a* (the feature being the output of the network, a 512×1 feature vector), an implementation of the ResNet50 network 915*b* (the feature being the output of the network, a 2048×1 feature vector), and an implementation of the MobileNet network (the feature being the final output of the network, a 1280×1 feature vector) 915*c*. One will appreciate that examples of such pretrained networks are made available in many libraries, e.g., in the Keras™ library (such as tf.keras.applications.VGG16, tf.keras.applications-.MobileNet, tf.keras.applications.ResNet50, etc.), each of which may load with networks pretrained upon a database, e.g., the ImageNet database.

The input shape to each network parameter may be 128×73×3 corresponding to a resized version of the image 905, where the image is RGB color. As regards VGG16, in some embodiments, features from the output of the final convolutional block may be provided to a global average pooling to reduce the spatial dimensions to yield a vector of 512 features for each video frame. Similarly, some embodiments may apply global average pooling on the output of ResNet50 and MobileNet networks, resulting in 2048 and 1280 features, respectively.

The resulting features may then be concatenated and applied to the intermediate classifiers 925*a*, 925*b*, 925*c*, 925*d*. Specifically, in this example implementation, an SVM 925*a*, logistic regression classifier 925*b*, random forest 925*c*, and Adaboost ensemble 925*d*. One will appreciate a variety of methods for implementing these classifiers, e.g., through specific libraries such as LIBSVM™ or more general libraries such as the Scikit-learn™ toolkit.

For example, code line listing C6 provides an example implementation of SVM 925*a* (one will appreciate that the default model used by SGDClassifier in Sckikit-learn™ is an SVM), code line listing C7 provides an example implementation of logistic regression classifier 925*b*, code line listing C8 provides an example implementation of random forest classifier 925*c*, and code line listing C9 provides an example implementation of an Adaboost ensemble 925*d* (using a decision tree as a base classifier). Some embodiments may additionally, or alternatively, employ a gradient boosting classifier as an intermediate model 925, as shown in the call to Scikit-learn™ library call shown in code line listing C10

```
SGDClassifier(loss="hinge",penalty="l2",al-
    pha=0.0001,max_iter=3000,tol=1e-3,n_jobs=-1)        (C6)

LogisticRegression(penalty='l2',tol=0.01,C=1.0,
    solver='saga',max_iter=500,random_state=123,
    n_jobs=-1)        (C7)

RandomForestClassifier(n_estimators=100,max_fea-
    tures=0.25,max_depth=10,min_samples_s-
    plit=20,min_samples_leaf=10,n_jobs=-1)        (C8)

AdaBoostClassifier
    (base_estimator=DecisionTreeClassifier
    (max_depth=1),learning_rate=1,n_estima-
    tors=50,random_state=123)        (C9)

GradientBoostingClassifier(learning_rate=0.1,n_esti-
    mators=10,subsample=0.8,random_state=123)        (C10)
```

In addition, some embodiments may in addition, or alternatively, employ unsupervised models, such as KMeans and GaussianMixture.

The results from each of these models, i.e., predicted frame field of view classifications 930*a*, 930*b*, 930*c*, and 930*d* respectively, may then be provided to fusion predictor 935*a* (which may itself be a machine learning model, such as a logistic regression classifier, SVM, etc., or logic, such as voting logic) and to an uncertainty calculator 940*a*, which may themselves each produce a final predicted value 945*a* and uncertainty 950*a*.

As will be discussed in greater detail herein, the uncertainty calculator 940*a* may determine the entropy of the class probabilities from classifications 930*a*, 930*b*, 930*c*, and 930*d*, e.g., using the scipy·stats entropy function from the SciPy™ library. In some embodiments, the uncertainty may be used to make decisions about which frames should be blacked-out and which should be kept (e.g., removing frames predicted as "in", but with high uncertainty). The uncertainty may also be used to monitor model drift due to changing data sources. That is, if the images 905 fed to the model change dramatically (e.g., if the data applied at inference is mistakenly taken from some source other than the endoscope, perhaps not even related to the surgical operation) the model will still make in/out predictions 945*a*, but uncertainty values 950*a* may fall so far outside the normal distributions that the system or a human operator will recognize that something is amiss.

Example Feature and Intermediate Model Relations

Figure 10A:
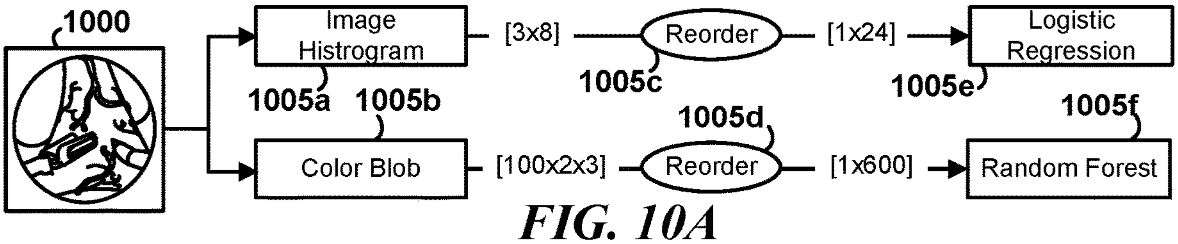
FIG. 10A is a schematic diagram illustrating an example feature generation and application to various intermediate machine learning models as may be implemented in various embodiments.

Again, while FIG. 9B depicts an example selection of features and intermediate classifiers for one class of embodiments, other embodiments may use different feature and classifier selections. For example, in FIG. 10A, rather than concatenating all the direct feature outputs and providing the same result to the intermediate models, in some embodiments the system instead determines only the image histogram 1005*a* and color blob 1005*b* features from an incoming image frame 1000. The image histogram 1005*a* may take the form of a 3×8 data structure (e.g., the cell count in each of the eight possible histogram directions for each of three separate channels) and the color blob 1005*b* may take the form of a 100×2×3 data structure (e.g., as mentioned above, the 100 largest blobs, with their two dimensional location, for each of the three color channels). Each of these features may be reordered 1005*c*, 1005*d* into linear vectors and supplied separately to a logistic regression classifier 1005e and random forest classifier 1005f. The results from each of these classifiers may then be considered by the fusion predictor 935 and uncertainty calculator 940 as discussed elsewhere herein.

Figure 10B:
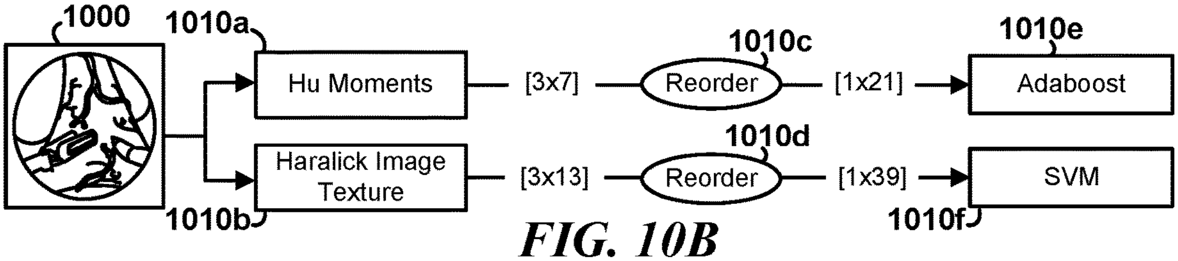
FIG. 10B is a schematic diagram illustrating an example feature generation and application to various intermediate machine learning models as may be implemented in various embodiments.

As another example class of embodiments differing from FIG. 9B, in the class of embodiments represented by FIG. 10B only the Hu moments 1010a and Haralick Image Texture features 1010b may be derived from the incoming image frame 1000. The Haralick Image Texture features 1010b may take the form of a 3×13 data structure (e.g., for each of the three channels, one or more of the 14 statistics identified by Haralick). Of the 14 Haralick statistics, such as angular second moment, contrast, correlation, variance, inverse difference moment, average sum, sum variance, sum entropy, entropy, variance difference, entropy, correlation measure 1 and 2, and maximum correlation coefficient, the last has been omitted in this example given its computational complexity. Hu moments 1010a may take the form of a 3×7 data structure as the seven most significant moments are selected in each channel. Each of these features may be reordered 1010c, 1010d respectively into linear vectors and supplied separately to an Adaboost classifier 1010e, e.g., as described above, and an SVM 1010f, e.g., also as described above. The results from each of these classifiers may then be considered by the fusion predictor 935 and uncertainty calculator 940 as discussed elsewhere herein.

Figure 10C:
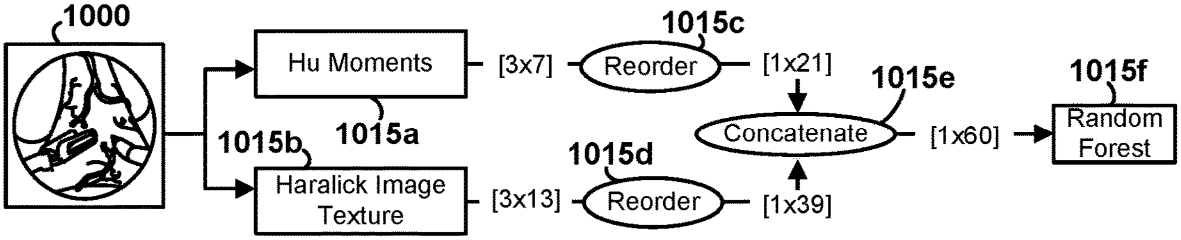
FIG. 10C is a schematic diagram illustrating an example feature generation and application to various intermediate machine learning models as may be implemented in various embodiments.

As mentioned with respect to FIG. 9B, some embodiments may concatenate features before providing them to an intermediate model. FIG. 10C provides another such example. Here, as in FIG. 10B, Hu moment features 1015a and Haralick features 1015b may be derived from an incoming image frame 1000. Again, the features may be reordered 1015c, 1015d into linear 1×21 and 1×39 feature vectors respectively. These may then, however, be instead concatenated 1015e and provided as a single vector of length 60 (21+39=60) to the one or more intermediate classifiers, in this case, a single random forest intermediate model 1015f (again, in some embodiments, where there is only one intermediate model, the model may also serve as fusion predictor 935a).

Figure 10D:
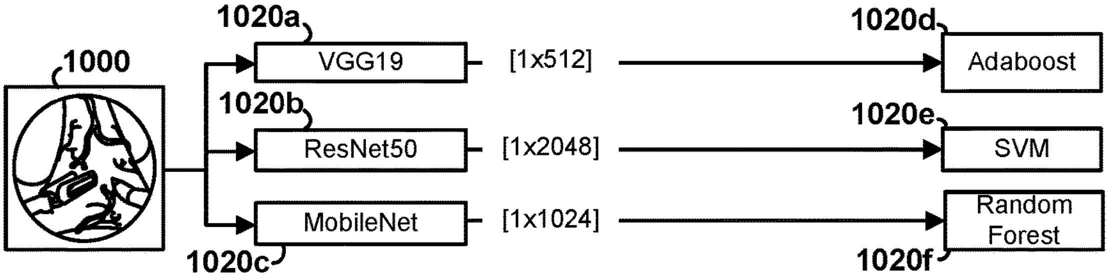
FIG. 10D is a schematic diagram illustrating an example feature generation and application to various intermediate machine learning models as may be implemented in various embodiments.

Similar joinings and separations of feature vectors among the direct features may also be performed with the neural network features. For example, in FIG. 10D a VGG19 network 1020a, ResNet network 1020b, and MobileNet network 1020c may produce 1×512, 1×2048, and 1×1024 dimensional outputs respectively (in accordance with their respective global pooling operations) from incoming image frame 1000. These outputs may be provided separately and directly to each of an Adaboost intermediate model 1020d, SVM intermediate model 1020e, and random forest intermediate model 1020f.

Figure 10E:
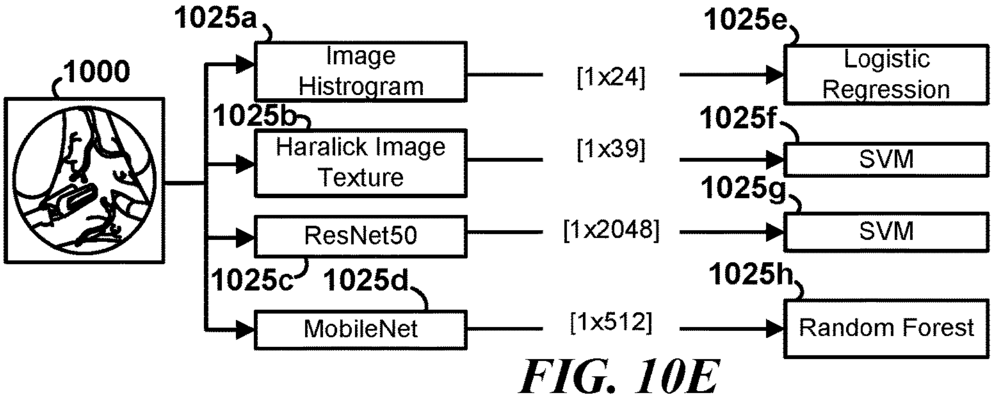
FIG. 10E is a schematic diagram illustrating an example feature generation and application to various intermediate machine learning models as may be implemented in various embodiments.

Again, as yet another example embodiment, one will appreciate as depicted in FIG. 9B, that feature vectors can be merged between the direct features 910 and neural network features 915. In addition, one will appreciate variations in the intermediate classifiers. Accordingly, in another example embodiment a combination of features and models is shown in FIG. 10E, wherein network models such as a MobileNet network 1025d may produce a 1×512 output, and a ResNet50 network 1025c may produce a 1×2048 output. Direct features, here, histogram 1025a and Haralick image feature 1025b may be produced. Each of these feature vectors may be fed to a corresponding classifier. Specifically, histogram output 1025a may be fed to a logistic regression intermediate classifier 1025e, Haralick image texture features 1025b may be fed to an SVM 1025f, ResNet50 output 1025c may be fed to a separate SVM 1025g, distinct from SVM 1025f, and MobileNet output 1025d may be fed to a random forest intermediate classifier 1025h. In a variation class of embodiments, the Haralick image texture output 1025b and ResNet50 output 1025c may be concatenated and fed to a single SVM classifier.

Though other selections and combinations have not been presented above, one will readily recognize additional variations in the features used, when and how the features are concatenated, and the selection of intermediate classifiers applied to the features. Furthermore, one will appreciate that each of the disclosed combinations may represent feature choices more suitable for certain operational contexts than others. For example, while the pair of features of FIG. 10A may impose little computational overhead, and therefore be suitable for real-time applications with limited resources, they may still not be as effective as other of the disclosed combinations for certain surgical operations. Specifically, if the surgeries under consideration involve fluorescent imaging, then some hues in the color blob 1005b associated with the fluorescence may appear similar to hues appearing in some endoscope-out images (e.g., depending upon the lighting of the operating room). In such situations, one may instead use the combination of, e.g., FIG. 10B or 10C since the Haralick image textures 1010b and image shape information captured in the Hu moments 1010a may serve to distinguish frames regardless of similarities in the fluorescent hue. Thus, while fewer features may generally incur lower computational overhead and simplify processing, one may also wish to consider the nature of the environment when selecting various of the proposed combinations.

Example Training Methodology

Figure 11A:
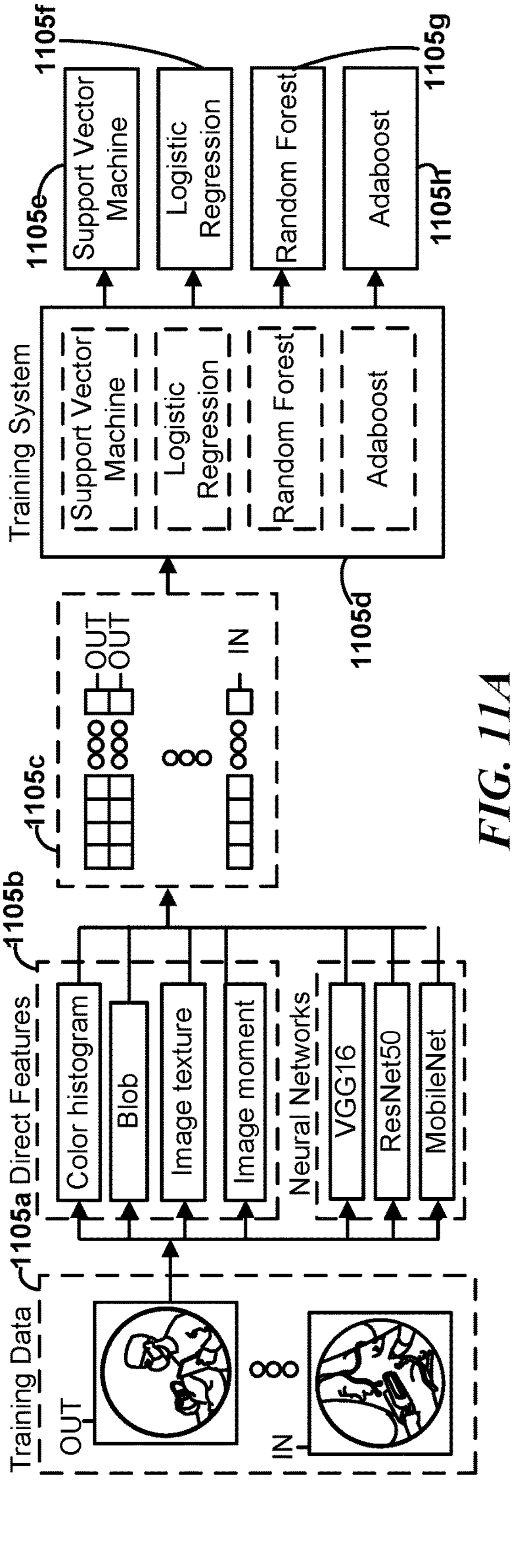
FIG. 11A is a schematic diagram depicting components for training one or more intermediate classifier example machine learning models of the topology of FIG. 9B.
Figure 11B:
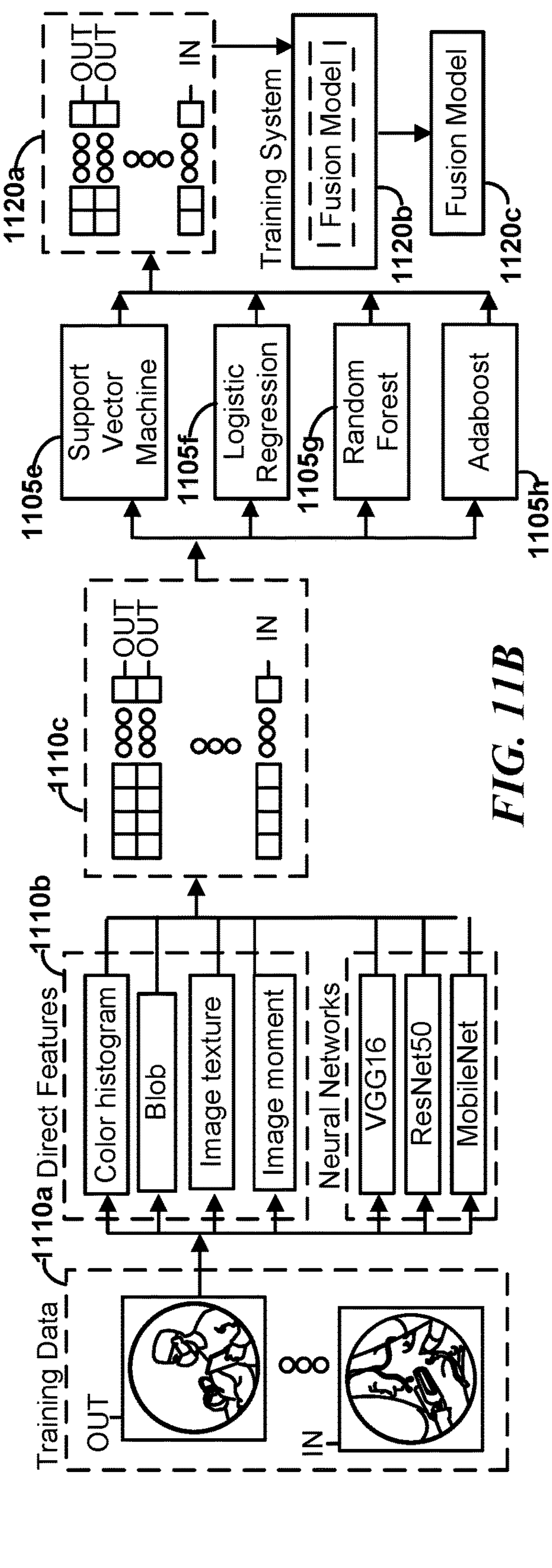
FIG. 11B is a schematic diagram depicting components for training a fusion model of the topology of FIG. 9B.

In some embodiments, the training of model 900b may proceed in stages. For example, FIG. 11A is a schematic diagram depicting components for training one or more intermediate classifiers in the topology of FIG. 9B. Where the fusion predictor 935 is a component performing logical operations, rather than a machine learning model, performing training in accordance with FIG. 11A may suffice to train architecture 900b (though, as mentioned, where networks 915 employ transfer learning, their head layers may be separately trained). However, where fused predictor 935 has parameters to calibrate, or is itself a machine learning model (e.g., an SVM, logistic regression classifier, etc.), then a second stage of training may be performed as shown in FIG. 11B.

Specifically, while architecture 900b is configured to receive an individual frame 905, training may be performed by providing a plurality of frames 1105a annotated with their status as IN or OUT frames (i.e., depicting fields of view inside the patient or outside). Each of these frames may be used to generate direct features 1105b (e.g., using feature extractor component 825b and the example library calls presented herein) and to be organized into sets 1105c suitable for training intermediate machine learning classifiers 925. One will appreciate that while sets 1105c are shown here as linear arrays with a corresponding annotation (as corresponding to an IN or OUT frame), one will appreciate that in some embodiments the features may not be linear and a single "feature set" may include differently formatted feature vectors or tensors for each of their respective intermediate machine learning classifiers 925. A training system 1105d, e.g., a computer system performing the training operation discussed herein, may train each of the intermediate machine learning models using the sets 1105c to produce trained classifiers 1105e, 1105f, 1105g, 1105h.

Trained classifiers 1105e, 1105f, 1105g, 1105h may then be used in the training of the fusion classifier model 1120c (or to configure parameters where the fusion classifier is logic rather than a machine learning model). Specifically, annotated frame data 1110a may again be converted to features 1110b and organized into sets 1110c (while data 1110a may be different than data 1105a in some embodiments, one will appreciate that where they are the same, sets 1105c may be reused to produce training set 1120a as discussed below). As applied to the now trained classifiers 1105e, 1105f, 1105g, 1105h corresponding classified outputs may now form a training set 1120a, which may be used by a training system 1120b to create trained fusion classier model 1120c.

Again, as discussed elsewhere herein, the fusion predictor 1120c may be logic (e.g., voting logic) rather than a trained classifier, combining the predictions of each classifier to generate a final prediction. For example, the fusion predictor may be code determining the argmax of each classifier and then performing a majority vote among the results. In some embodiments, voting may instead involve averaging the probabilities for each class from each predictor to produce a new class probability vector, then normalizing this vector to confirm that the average probability across classes still sums to 1, before then taking the argmax of this average probability vector. Here, in FIG. 11B, however, fusion model 1120c may be, e.g., a logistic regression model that learns how to weight the class probabilities of each classifier to overcome the biases of each method.

One will also appreciate that in some embodiments annotated feature vector training sets 1105c and 1110c may be the same set or different sets (i.e., sets generated from different annotated input images). Reusing the sets 1105c as sets 1110c may be desirable where acquiring new data or regenerating features is not desirable or feasible. In some embodiments, the available data may be divided between the two training operations of FIGS. 11A and 11B to better ensure robust machine learning models.

FIG. 12A is a flow diagram illustrating various operations in a process for training one or more intermediate machine learning models 925 as may be implemented in some embodiments. Generally, the practitioner may wish to determine which selection of models is best suited for the type of data under consideration, as well as which selection or combination of feature types is best suited for each model. While a human reviewer may manually inspect the training results to select feature vectors and models, one will appreciate that the training process may be automated or used in conjunction with a meta-learning machine learning method.

Specifically, at block 1205a the training system may receive annotated (as being inside or outside the patient) video of surgical procedures. In some embodiments, the video may have been annotated by human reviewers. However, in some embodiments the video may be "annotated" based upon system or kinematics data accompanying the video or within the video. For example, as discussed, kinematics data 530 (e.g., indicating the position and orientation of tools over time) or events data 535 captured contemporaneously with the video may already indicate when the video's field of view is inside or outside a patient. Similarly, some systems may include user interfaces in the video capture indicating whether the field of view is inside or outside the patient (e.g., template matching to recognize an icon in this interface indicating in/out positioning may be used for "annotation").

At block 1205b, the system may preprocess the video. Such preprocessing may involve down sampling, resizing the video frames to a consistent form, converting compressed video to individual frames, etc. At block 1205c, the training system may convert the annotated video frames to annotated features vectors in accordance with the selection or omission of direct and neural network features described herein. For example, the practitioner or training system may elect to select some of "direct features" 910 and "network features" 920, all of the possible features, various concatenations of two or more of the selections, etc.

The system may then iterate through the intermediate model types 925 chosen for consideration at blocks 1205d and 1205e. Similar to feature selection, the practitioner or meta-learning training system may select only one model (e.g., a Random Forest) or multiple model types for consideration (e.g., a Logistic Regression Classifier model, an SVM, and a Random Forest). For each of the model types, at block 1205f the practitioner or training system may train the model upon each of the selected feature types on various selections of the available data, e.g., as will be described in greater detail with reference to FIG. 12B. Such training may produce a plurality of "candidate" trained models which may be stored at block 1205g for consideration at block 1205h. For example, at block 1205h each of the stored trained models and their validation results may be considered to select the trained models best suited for use in conjunction with a fusion classifier (e.g., selecting the models with the top 5 performing validation results with the expectation that the fusion classifier will take a majority vote). Once the selection has been made, the feature generation process can be streamlined for inference (e.g., generating only the feature types used by the selected models for incoming video data).

FIG. 12B is a flow diagram illustrating various operations in an intermediate machine learning model training process, e.g., as may be applied at block 1205f of FIG. 12A in some embodiments. At blocks 1210a and 1210b, the system may iterate over the contemplated feature types, e.g., those types selected at block 1205c.

In some embodiments, at block 1210b, features from frames from all available training videos may be collected and the frames split into training and testing sets (training here including validation and the testing sets used to assess final performance). In some embodiments, the system may instead first splits videos into training and testing groups of videos, and then collect frames from each group of videos for training and testing (again, training here including validation while the testing sets are used to assess final performance). The latter approach may facilitate testing the video-wise model generalizability, i.e., whether a model can perform well on new video, while the former method may emphasize robustness as to frame-wise modeling.

At block 1210c, the system may select the fold allocations for the training data in the selected feature format. One will appreciate that "K-folds" training cross validation is a technique to avoid overfitting upon the data. For example, with reference to the example training data 1215a of FIG. 12C, the training data 1215a may be in the format of the selected features and annotated as discussed elsewhere herein. At block 1210c this data may be divided into a training portion 1215b, for training at validation, and a test portion 1215c to assess the final results (in some embodiments, test portion 1215c may be omitted and all available training data used as training portion 1215b). Training portion 1215b may itself be used to determine the model's hyperparameters, while the test portion 1215c may be withheld to provide a final assessment of the generated models. To this end training portion 1215b may itself be divided into "folds" of roughly equal groupings of data (here three such folds are shown). At each training iteration, a version of the model's hyperparameters may be determined by using all the folds for training the model (e.g., in the first model, Fold 2 and Fold 3 may be used for training, Fold 1 for validation; in the second model, Fold 1 and Fold 3 may be used for training, Fold 2 for validation, etc.).

As discussed herein, many datasets will have many more "in" frames than "out" frames, and such asymmetric representation may also be present in individual folds of data 1215a. Thus, in some embodiments, at block 12101 the system may consider if the training data within the presently considered fold is balanced. If not, elements of the under-represented data (typically, "out" data) may be up sampled, e.g., using the Synthetic Minority Over-sampling Technique (SMOTE) algorithm, at block 1210e. In this manner, up sampling at each fold iteration may help ensure consistency between the training and validation folds.

At block 1210f, the system may determine the hyperparameters for the current fold selection by training the model in accordance with the model's training methodology. Using the remaining fold of data, the system may then perform validation, evaluating the trained model at block 1210g and saving the model and results at block 1210h and 1210i respectively. In some embodiments, evaluation at block 1210g may involve validating individual frames or validating entire videos of data. The former may provide robustness between video captures, while the latter may provide robustness within single videos. In the latter, in some embodiments, the predicted values may be temporally smoothed using the same or similar operations as performed by smoothing component 825d, where such smoothing will likewise be applied during future inference. In some embodiments, each of these variations may be pursued at each iteration of the K-folds to provide an even wider selection of possible models for use.

After the folds of training have been performed at block 1210d, the system may review the results saved at block 1210i and select the best performing of the models at block 1210k. However, in some embodiments, this assessment may be deferred until all the models of all the model types have been trained, and then the comparison made at block 1205h (e.g., some meta-learning algorithms may wish to make available all possible trained model combinations for competitive comparison).

Example Smoothing Methodologies

Figure 13A:
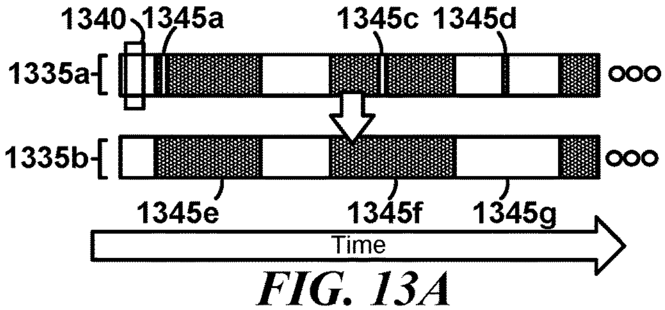
FIG. 13A is a schematic diagram depicting the application of a smoothing window to a set of data classification values as may occur in some embodiments.

After applying the classifications operations described herein, post-processing operations, such as smoothing, may be applied (e.g., via smoothing component 825d) to help reduce false negative and false positive classifications. FIG. 13A is a schematic depiction of the application of a smoothing window 1340 to a set of data classification values as may occur in some embodiments. Generally, the window 1340 may be slid in the temporal direction (e.g., from left to right as depicted here, where the frames are arranged in temporal order from left to right) considering classifications for frames before and after the frame under consideration. For example, some embodiments employ a window 1340 size of 3 seconds, considering frames 1.5 seconds in the past and 1.5 seconds in the future relative to the frame currently under consideration. One will appreciate that buffer values may be prepended and appended to the frame sequence (e.g., the first frame's classification value may be prepended within the window for the initial considerations and the final values' classifications appended within the window for the final frames' consideration), though some embodiments may instead simply forego smoothing for frames at each end. Similarly, the window may not be constant over the course of the sliding operations, expanding and shrinking over regions anticipated to possess more or less noisy values, respectively. In this manner, false positive/negative regions 1345a, 1345c, 1345d may be removed from the original per-frame, per-second, etc. classification results 1335a, producing smoothed output 1335b having smoothed regions 1345e, 1345f and 1345g.

Figure 13B:
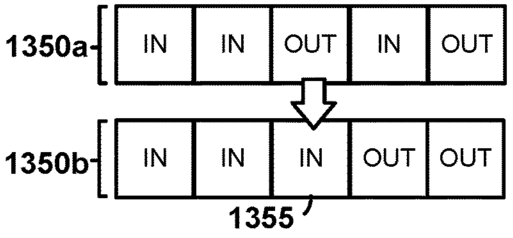
FIG. 13B is a schematic diagram depicting classification reordering via a median filter as may be used in the window of FIG. 13A in some embodiments.

The filtering operation within the window 1340 may vary between embodiments. One effective window used in some embodiments takes a majority vote among the predictions in the window. One will appreciate that such a vote can be implemented in a variety of ways, e.g., via majority vote logic or a median filter. For clarity, FIG. 13B illustrates an example of such a median filter's operation for a five frame window. A median filter may arrange the classifications 1350a for each frame as they occur in the original temporal frame sequence into a new "ascending" order 1350b and then take the value in the median position 1355 as the value of the central frame under consideration (as there are only two classification values, one will appreciate that selecting the median/middle in this manner for an odd number of frames is equivalent to a majority vote). As another alternative, one could instead apply a gaussian filter, e.g. "gaussian_filter1d(input_seq, sigma=0.7)" as made available in the SciPy™ library, to accomplish the window smoothing.

Smoothing may also be accomplished with Hidden Markov Model (HMM) filtering. In these embodiments, the HMM model parameters may be estimated from ground truth labeled data using Expectation-Maximization with the Baum-Welch algorithm. One will appreciate multiple methods for implementing such functionality, e.g., using the popular Hmmlearn™ Python library which facilitates unsupervised learning. Parameters can also be "guessed" by estimating reasonable start probabilities and transition matrices after inspecting ground truth frame annotations. An example Hmmlearn™ Python library based implementation may proceed as shown in code line listings C11-C14:

```
hmm_decoder=MultinomialHMM(n_components=2)    (C11)

hmm_decoder.transmat_=np.array([[0.95,0.05],[0.05,
    0.95]])    (C12)

hmm_decoder.emissionprob_=np.array([[0.98,0.02],
    [0.12,0.88]])    (C13)

smoothed=hmm_decoder.decode(sequence.reshape(−
    1,1))    (C14)
```

where line C12 refers to the transition matrix (e.g., the probability given an OUT state in a first frame, of the next frame being an OUT or IN frame—as indicated there's a 95% probability in this example that OUT frames will follow OUT frames and IN frames will follow IN frames). Similarly, line C13 indicates that, given a frame classified as IN by the models, there's a 98% chance it genuinely is IN and a 2% chance it's actually OUT. Similarly, C13 indicates that given a frame classified as OUT by the models, there's a 88% chance it genuinely is OUT and a 12% chance it's actually IN. One will appreciate that the probabilities in lines C12 and C13 may be determined in a variety of manners, including visual inspection of the training data. For example, the probabilities in line C13 may be determined by computing the results confusion matrix from the model classifications, and then normalizing the confusion matrix rows. Similarly, the probabilities in lines C12 may be determined by counting all the true positive transitions (i.e., from IN to OUT in successive video frames or OUT to IN in successive frames) in the dataset and dividing by the total count of such transitions.

Using the HMM, the system may iterate along the initial predictions and adjust the output to the most probable classifications based upon the HMM where the HMM disagrees with the original prediction. For example, one will appreciate that the HMM may be used with the forward-backward algorithm to smooth initial predictions.

Naturally, one will also appreciate that in some embodiments any revised frame classifications following smoothing may not be applied until after smoothing is complete (i.e., the smoothing results may be stored in a temporary buffer as they are produced and outputted only when the smoothing processing is complete). Otherwise, as in the example of FIG. 13B, once the window encountered 4 classifications of the same value, such value would predominate and be assigned to all subsequent frames.

Example Surgical Operation Start/End Time Detector

Figure 13C:
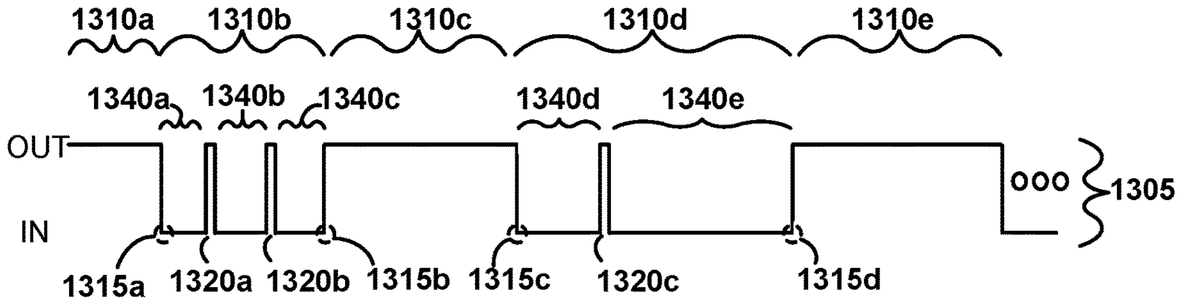
FIG. 13C is a schematic depiction of an example in/out classification signal waveform as may be operated upon by the process of FIG. 13D in some embodiments.
Figure 13D:
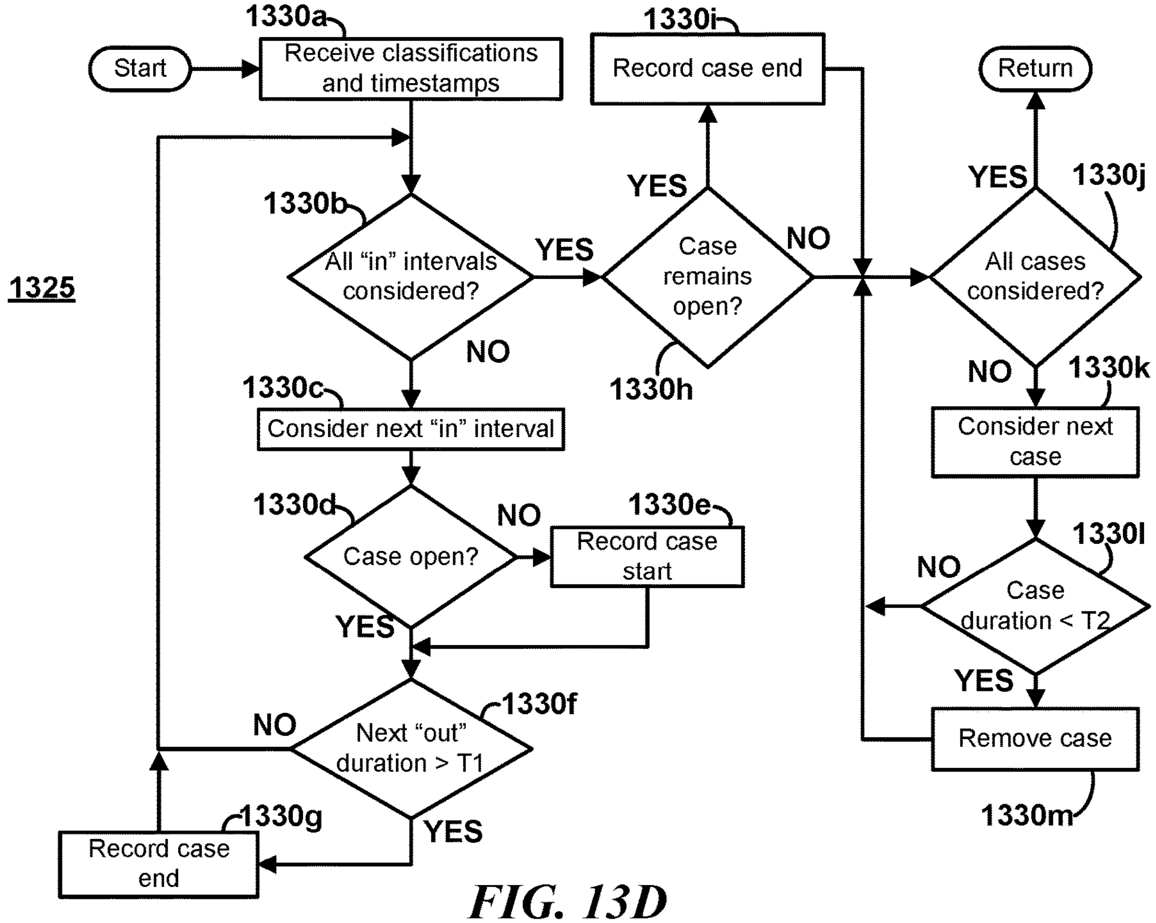
FIG. 13D is a flow diagram illustrating various operations in a surgical operation segmentation process as may be implemented in some embodiments.

Following classification, and in some embodiments smoothing, the classification results may be provided to the start/end time detector 825*e*, which may perform various of the operations shown in the process 1325 of FIG. 13D. The accompanying FIG. 13C depicts an example in/out classification signal waveform (e.g., following smoothing) as may be operated upon by the process of FIG. 13D in some embodiments. In the example waveform 1305, regions of outside-classified frames 1310*a*, 1310*c*, and 1310*e* may reflect genuine inter-surgery periods, while regions of outside-classified frames 1320*a*, 1320*b*, and 1320*c* may instead reflect brief removals and reinsertions of the visualization tool. Accordingly, start/end time detector 825*e* seeks to recognize each of the intervals 1310*b* and 1310*d* as intervals comprising distinct surgical cases.

At block 1330*a*, start/end time detector 825*e* may receive frame classifications and corresponding timestamps, e.g., as represented by waveform 1305. At blocks 1330*b* and 1330*c*, the detector may then determine whether all the intervals of frames classified as outside the patient have been considered, i.e., the intervals 1340*a*, 1340*b*, 1340*c*, 1340*d* and 1340*e*. The detector may recognize an "interval" as any group of consecutive classifications. If the system has not yet noted the beginning frame of a surgical case, or if the system has just noted the final frame of surgical case and not yet begun a new entry, as evidenced by block 1330*d*, then at block 1330*e* the system may begin a new surgical case entry, marking the beginning of the current "in" interval as the surgical case's start time.

At block 1330*f*, the system may consider whether the next "out" interval exceeds a threshold T1 in duration. In some embodiments, T1 may be approximately 29 minutes, as inspection of ground truth videos for the considered surgeries indicated that few visualization tool removals exceeded this amount of time, while inter-surgery periods regularly would exceed such a period. One will appreciate, however, that the interval may be adjusted depending upon the context (e.g., military emergency surgical theaters in a war zone may experience much quicker turn-around times between trauma surgeries as compared to domestic surgical theaters performing elective surgeries). Where there is no next "out" interval or the next "out" interval's duration exceeds the T1 threshold, the process may transition back to block 1330*b*. Conversely, if the next "out" interval exceeds the threshold T1, the end time for the currently considered "in" interval may be recorded as the end time for the current surgery at block 1330*g*.

One will appreciate that where the final interval considered was an "in" interval or where the last considered "out" interval was less in duration than the T1 threshold, then the currently considered surgery may be without an end time in the video (as may occur, e.g., when recorded surgeries exhaust one recording medium and continue on a separate recording medium). If this is the case at block 1330*h*, then the end of the video (i.e., the timestamp of the final frame in the entire video) may be marked as the end of the currently considered surgical case at block 1330*i*.

At this point some embodiments may conclude the start/end time detection process. In some embodiments, however, the system may verify the plausibility of the identified surgery start and stop times (e.g., to remove spurious surgical cases). In these embodiments, the process may continue to block 1330*j* to consider each of the surgical case start/stop times recorded via the previous iterations. For each of the surgical cases as considered at block 1330*k*, the system may verify that the surgical case's duration is less than a second threshold T2 at block 1330*l*, and if so, remove the surgical case from the group of created entries at block 1330*m*. In some embodiments, T2 may be approximately four minutes, as inspection of results from ground truth video indicated that personnel actions (e.g., visualization tool cleaning) between surgeries may result in false surgical cases being created between genuine surgical cases. One will appreciate that selection of the threshold T2 may be affected by the selection of the window for smoothing and by the surgical context (e.g., some training "surgeries" in a virtual environment may comprise only a few minutes). Following consideration of all the surgical cases at block 1330*j* post processing may conclude and may, e.g., provide the results to processing component 825*f* (e.g., for the non-surgical frames to be removed, the data to be encrypted, etc.) or store the results in storage processing component 825*g*. Though it may be self-evident from the identified cases (e.g., where represented as an array of timestamps), in some embodiments, post-processing may also include explicit identification of the start 1315*a*, 1315*c* and end 1315*b*, 1315*d* times of the respective surgeries.

Example Uncertainty Algorithms

One will appreciate a variety of processes for determining uncertainty at calculator 940. For example, each of FIGS. 14B and 14C depict example processes for measuring uncertainty with reference to a hypothetical set of results in the table of FIG. 14A. In the example process 1400*a* of FIG. 14B, a computer system may initialize a holder variable "max" at block 1405*a* for the maximum count among all the classification classes (i.e., "IN" or "OUT" classifications). The system may then iterate, as indicated by block 1405*b*, through each of the classes. As each class is considered at block 1405*c*, the class's maximum count "max_cnt" may be determined at block 1405*d* and compared with the current value of the holder "max" at block 1405*e*. If max_cnt is larger, then max may be reassigned to the value of max_cnt at block 1405*f*.

For example, with reference to the hypothetical values in table of FIG. 14A, for classes "Inside" and "Outside" and given five intermediate classifier results, as indicated, calculator 940 may produce predictions as indicated in the table. Specifically, intermediate model 1 produced a 50% probability of the frame belonging to Class "Inside" and a 50% probability of the frame belonging to Class "Outside". During the first iteration through block 1405*c*, the system may consider Class "Inside's" value for each frame. Here, Class "Inside" was a most-predicted class (ties being each counted as most-predicted results) for classifiers 1, 2, 3 and 5. As it was the most predicted class for these four sets, "max_cnt" is 4 for the Inside class. Since 4 is greater than 0, the system would assign the "max" to 4 at block 1405*f*. A similar procedure for subsequent iterations may determine a max_cnt value of 2 for Class "Outside". As this subsequent "max_cnt" determination was less than 4, "max" will remain as 4 when the process transitions to block 1405*g* after considering each of the classes. At this block, the uncertainty may be output as shown in Equation 4:

$$1 - \frac{\text{max}}{\text{model\_cnt}} \tag{4}$$

where "model_cnt" is the number of intermediate classifiers. Continuing the example with respect to the table of FIG. 14A, there are five classifier results and so the uncertainty is 1−4/5, or 0.2.

FIG. 14C depicts another example process 1400*b* for calculating uncertainty. Here, at block 1410*a*, the system may set an "Entropy" holder variable to 0. At blocks 1410*b* and 1410*c* the system may again consider each of the classes, determining the mean for the class at block 1410*d* and appending the log value of the mean to the Entropy variable at block 1410*e*, where the log is taken to the base of the number of classes. For example, with reference to the table of FIG. 14A, one will appreciate that the mean value for Class "Inside" is $$\frac{0.5 + 0.8 + 0.6 + 0.2 + 1}{5} = 0.62 \tag{5}$$

With corresponding mean calculation shown for the Class "Outside." Once all the classes have been considered, the final uncertainty may be output as the negative of the entropy value divided by the number of classes at block 1410*f*. Thus, for the example means of the table in FIG. 14A may result in a final uncertainty value of approximately 0.12.

One will recognize the process of FIG. 14C as calculating the Shannon entropy of the results. Specifically where $y_{c,n}$ represents the SoftMax prediction output for the $c^{th}$ class of the $n^{th}$ frame set $$\hat{y}_c = \frac{1}{N}\left(\sum_{n=1}^{N} y_{c,n}\right) \tag{6}$$

Which as indicated above, may then be consolidated into a calculation of the Shannon entropy H $$H = -\frac{1}{\text{Class\_Cnt}}\left(\sum_{c=1}^{class\_Cnt} \hat{y}_c \log(\hat{y}_c)\right) \tag{7}$$

where Class_Cnt is the total number of classes (e.g., in the table of FIG. 14A, Class_Cnt is 2). One will appreciate that, by convention, that "0 $\log_{Class\_cnt}$ 0" is 0 in these calculations.

One will appreciate that the approaches of FIGS. 14B and 14C are in some respects complementary and so both may be used and their results averaged in some embodiments.

For completeness, as discussed, where the fusion model is a generative model, uncertainty may be measured from the predictions rather than by considering multiple model outputs as described above. For example, in FIG. 14D, the fusion predictor 935*a* is a generative model 1425*b* configured to receive the concatenated feature results 1425*a* and output predictions 1425*c* and 1425*d* (i.e., "in" or "out" classifications). For example, a Bayesian neural network may output a distribution, selecting the highest probability distribution as the prediction (here, prediction 1425*d*). Uncertainty logic may here assess uncertainty from the variance of the prediction distribution 1425*d*.

One will appreciate additional methods for assessing uncertainty. For example, where the fusion predictor 935*a* is a neural network, iterative application during inference with dropout of various nodes in the neural network may likewise produce a distribution analogous to prediction distribution 1425*d* from whose variance an uncertainty may be calculated by uncertainty logic.

Example Deployment Topologies

Figure 15A:
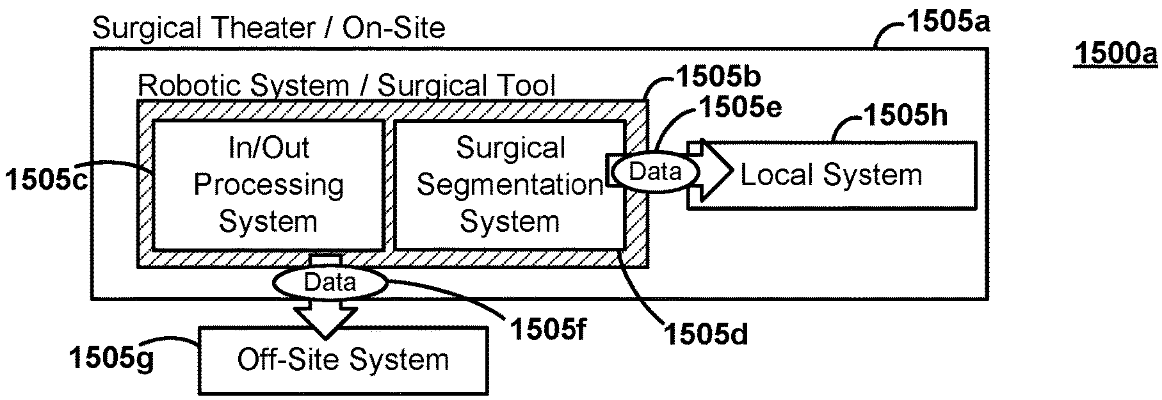
FIG. 15A is a schematic diagram illustrating an example component deployment topology as may be implemented in some embodiments.

As discussed above, one will appreciate that the components 825*a*, 825*b*, 825*c*, 825*d*, 825*e*, 825*f*, 825*g* may reside at many different locations, including all appearing at the same location. For example, FIG. 15A is a schematic diagram illustrating an example component deployment topology 1500*a* as may be implemented in some embodiments. Here, the components 825*a*, 825*b*, 825*c*, 825*d* have been generally consolidated into a single "in/out processing system" 1505*c*, while components 825*e*, 825*f*, 825*g* have been consolidated into a surgical segmentation system 1505*d*. In this topology, each of system 1505*c* and 1505*d* reside on a same robotic system or surgical tool (e.g., an on-device computer system, such as a system operating in conjunction with a Vega-6301™ 4K HEVC Encoder Appliance produced by Advantech™) 1505*b* appearing in theater 1505*a*. For example, the systems may each be software code running on an on-system processor of patient side cart 130 or electronics/control console 145, or firmware software on a tool 110*b*. Locating systems 1505*c* and 1505*d* within the surgical theater 1505*a* in this manner may allow for secure processing of the data, facilitating transmission of the processed data 1505*e* to another local computer system 1505*h* or sending the processed data 1505*f* outside the surgical theater to a remote system 1505*g*, free from regulatory or other hurdles discussed herein. That is, since the sensitive portions of the video and corresponding kinematics and system data have been excised, data 1505*e* and 1505*f* may be subject to less stringent regulatory requirements, e.g., encryption, than absent such censorship.

Thus, local computer system 1505*h* may be, e.g., an in-hospital network server providing access to outside service providers or other internal data processing teams. Similarly, offsite computer system 1505*g* may be a cloud storage system, a storage of a third party service provider or regulatory agency, etc. One will appreciate that in some topologies, segmentation system 1505*g* may be relocated to local system 1505*h* or to off-site system 1505*g*.

Figure 15B:
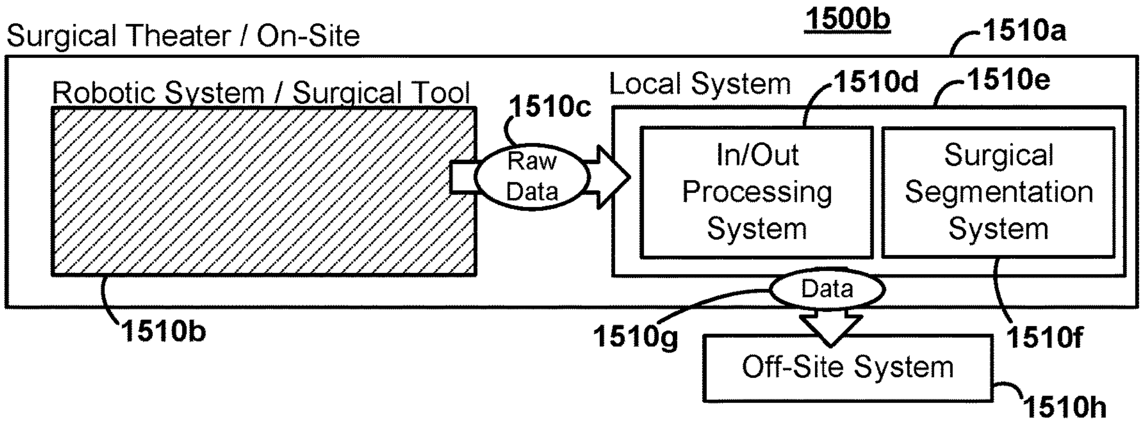
FIG. 15B is a schematic diagram illustrating an example component deployment topology as may be implemented in some embodiments.

However, some embodiments contemplate topologies such as topology 1500*b* of FIG. 15B wherein one or both (as shown here) of the processing systems 1510*d* and 1500*e* are relocated to a local system 1510*e* not collocated on the robotic system or tool 1510*b*, but still within the control of the surgical theater or operating institution 1510*a*. This topology may be useful where the processing is anticipated to be resource intensive and a dedicated processing system, such as local system 1510*e*, may be specifically tailored to efficiently perform such processing (as compared to the possibly more limited resources of the robotic system or surgical tool 1510*b*). Robotic system or surgical tool 1510*b* may now provide the initial raw data 1510*c* (possibly encrypted) to the local system 1510*e* for processing.

Once processed and the sensitive data is removed, the system may provide the data 1510*g* (possibly now unencrypted) to offsite system 1510*h*, such as a cloud server, as, again, the regulatory burden or risk exposure may now be greatly reduced following censorship processing. Again, one will appreciate that systems 1510*d* and 1510*f* need not necessarily travel together as shown. For example, segmentation system 1510*f* may reside on off-site system 1510*h*. Such an arrangement may be suitable when one is confident system 1510*d* will excise any sensitive information and offsite system 1510*h* has greater computational or network resources for additional processing, such as recognizing distinct surgeries with system 1510*f*.

Figure 15C:
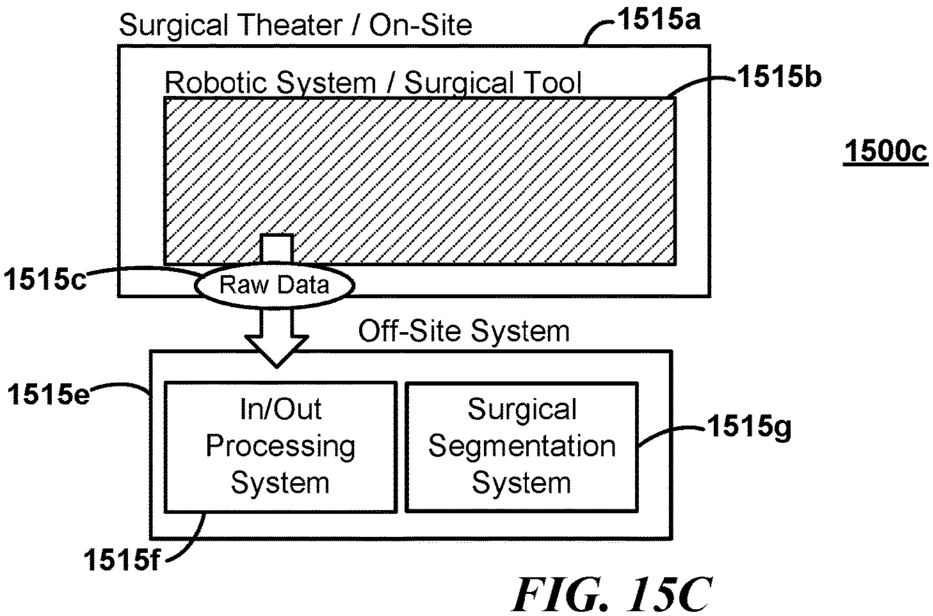
FIG. 15C is a schematic diagram illustrating an example component deployment topology as may be implemented in some embodiments.

In some embodiments, processing may be entirely performed on an offsite system 1515*e*, such as a cloud server system, with considerable and flexible data processing capabilities. As shown in FIG. 15C, moving processing systems 1515*f* and 1515*g* to the cloud system may result in raw data 1515*c*, including sensitive information, from the robotic system or surgical tool 1515*b* leaving the control of the surgical theater 1515*a*. This may be suitable where, e.g., the data is encrypted and/or travels over controlled network channels (or is hand-delivered) to the off-site system 1515*e*. The topology 1500*c* of FIG. 15C may be suitable where the processed data is to be received by a variety of downstream systems likewise located in the cloud or an off-site network.

Example Results

Example implementations of various embodiments were reduced to practice to evaluate the efficacy of the approaches disclosed herein. FIG. 16A is table depicting properties of two example datasets, the DaVinci16 dataset, which included robotic-assisted procedures as in theater 100*b*, and the Cholec80 dataset, which included endoscopic video recordings from theaters such as theater 100*a*, used in evaluating various example implementations of various embodiments. Both datasets included in and out-of-body frames. The DaVinci16 dataset consisted of 16 video sessions where each video contains surgical procedures performed on either the da Vinci X™ or Xi™ surgical system. Each video was sampled at 30 fps and the durations range from 20 to 150 minutes approximately. The Cholec80 dataset is a public dataset containing laparoscopic cholecystectomy surgeries. It consists of 80 video sessions in total sampled at 25 fps where the durations of videos range from approximately 7 to 100 minutes. Each video session in the Cholec80 dataset included a single surgical procedure, while a given video session in the DaVinci16 dataset might contain one or more surgical procedures. All videos from both datasets were down-sampled to 1 FPS and each video frame was resized to minimize processing time to a resolution of 128×72 pixels. Since no prior ground-truth knowledge existed in the Cholec80 dataset, labels of all endoscopic frames were generated by observation and manual annotation. Four annotators with an understanding of the procedures depicted in the videos were recruited to view the videos and label each video frame with a binary label indicating "inside-body" or "outside-body". Overall, the DaVinci16 dataset contains 84,622 frames in total with 16,271 endoscope out-of-body frames and the Cholec80 dataset contains 176, 192 total frames with 3,444 endoscope out-of-body frames.

FIGS. 16B and 16C show schematic plots of example F1 score results using different features and classifiers upon the two datasets. That is, each figure shows the quantitative results of frame recognition using varying features as input derived from robotic assisted surgery data (the DaVinci16 dataset), FIG. 16B, and laparoscopic surgery data (the Cholec80 dataset), FIG. 16C. For each dataset, different features were generated (Blob, Color, etc.), a portion of which were used for training individual intermediate models (Logistic Regression, Random Forest, etc., e.g. discussed in code line listings C6-C10) and the remaining portion used to validate their performance and produce F1 scores as depicted in these figures.

As indicated, the color histogram provided the best classification performance over the two datasets, with the highest recall of 98% and 96% at the level of frame and video session, respectively. These results also show that the network features were able to achieve similar accuracies for the endoscopic frame recognition. Network features had an average 78%-89% recall at the frame-level recognition and 77%-91% recall at the session-level recognition. Specifically, VGG features consistently outperformed the ResNet features, followed by MobileNet features in both datasets. This suggests that, despite being learned initially from unrelated image data, deep features can still do well for classifying out-of-body frames in endoscopic videos. While these results of this example implementation indicate that some models and features performed better than others, one will appreciate that such results are unique to the context and embodiments selected for experimentation and that other choices of features and models may be more suitable, and produce different results, in other situations.

Figure 17:
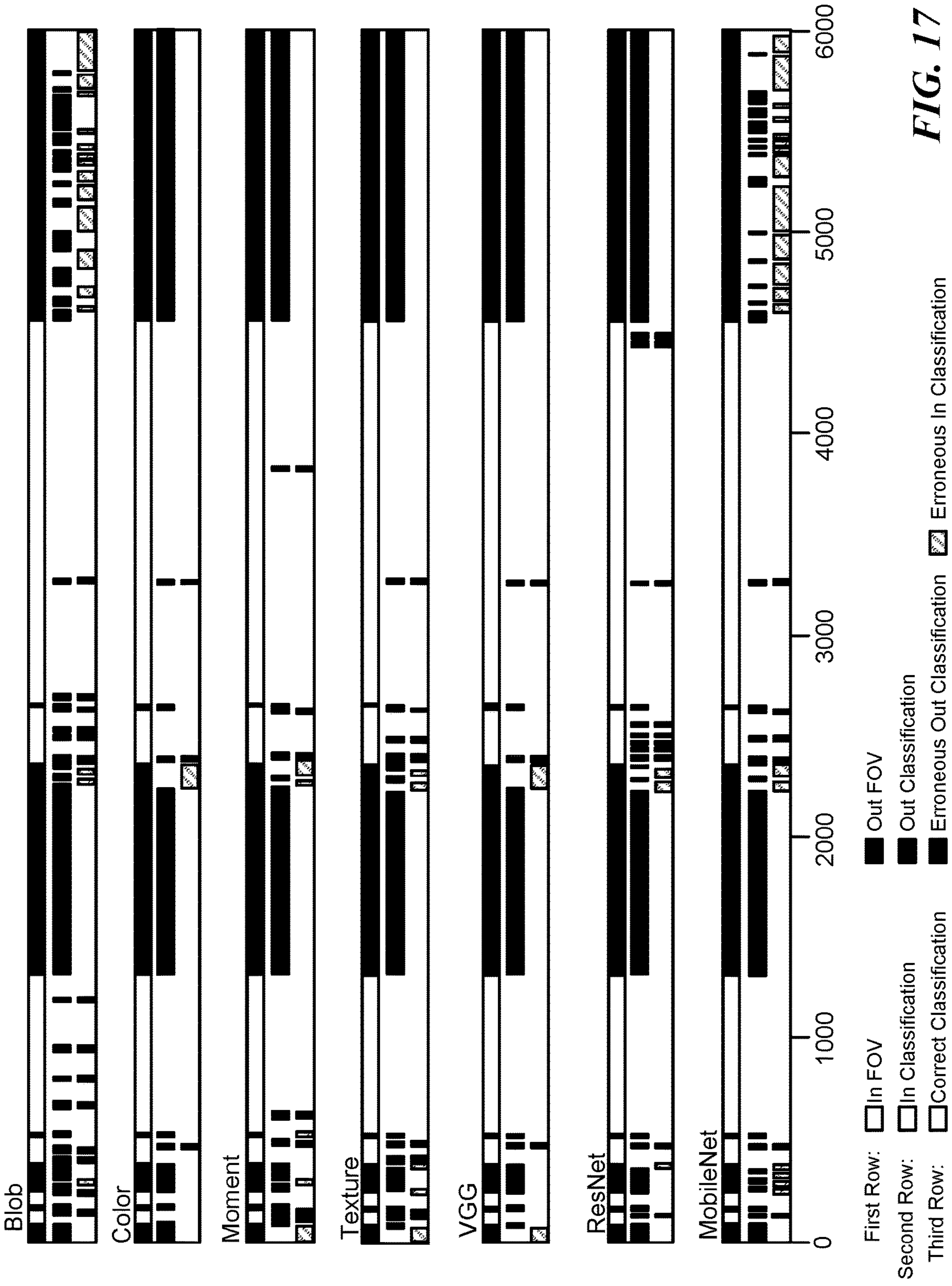
FIG. 17 is a schematic collection of time series data resulting from an example implementation's consideration of various feature types exclusively.

FIG. 17 illustrates schematic plots of example segmentation bars for endoscopic out-of-body frame recognition in a session of robotic-assisted surgery upon the combined DaVinci16 and Cholec80 datasets for a specific feature. As a random forest model in isolation performed well in FIGS. 16B and 16C, a random forest model (serving as both intermediate model 925 and fusion model 935) was used here, but evaluated with different input features. Each feature block contains three rows depicting the data ground truth (top row), predictions using the feature type (middle row), and the corresponding discrepancy compared to the ground truth (bottom row) frame labels. Similarly, one will appreciate that these results are unique to the context of the example implementation and that implementations of the same or different embodiments may not produce identical results.

Two sets of validation experiments were conducted during training. First, performance was evaluated using a three-fold cross-validation upon the entire DaVinci16 dataset. This setting randomly split all sessions into two sets wherein, in each fold, 80% of the sessions were used for training/validation and the remaining 20% sessions were held-out for testing. To handle imbalanced samples and achieve a robust modeling, the minority class observations from the training data in each fold were oversampled. New samples in the "out" class which was under-represented (i.e., endoscopic out-of-body frame) were generated using SMOTE oversampling method (SMOTE(random_state=12, ratio=1.0) where the "SMOTE" function was as made available through the Imblearn™ library function imblearn.over-_sampling.SMOTE). One will appreciate that such oversampling may be suitable in many such embodiments described herein where such dataset asymmetry is present. This approach may improve the modeling performance when trained upon imbalanced data and may not leak any testing data information into training. In these examples, all evaluation metrics were computed on the testing sets in each fold and averaged over the folds to reduce any evaluation bias. The same validation strategy was pursued for the Cholec80 dataset with over-sampling training data in each fold.

As shown in FIG. 16A, only a relatively small fraction of observations in the datasets were labeled as endoscope out-of-body frame. Therefore, the above-mentioned metrics were calculated with respect to each class and the average then considered over all classes as an unbiased evaluation of the imbalanced data. In addition to the frame-level evaluation that does not incorporate the temporal continuity, session-level reports that evaluate the performance at a higher level across video sessions were also produced. This was done by first calculating the performance metrics in each video and then averaging metrics across all testing video sessions. The session-level evaluation may be construed as describing how the model generalizes to out of sample data, i.e. unseen video sessions.

Again, as a random forest model in isolation performed well in FIGS. 16B and 16C, an additional cross-surgery experiment was performed, wherein the random forest model (again serving as both intermediate model 925 and fusion model 935) was trained on the robotic-assisted surgery data (DaVinci16) and applied to the laparoscopic surgery data (Cholec80) without any model adaptation, and vice versa. This experiment was aimed at verifying the model generalizability across the two types of surgeries. The results are presented in the tables of FIG. 18A and FIG. 18B.

Figures 18A, 18B, 18C:
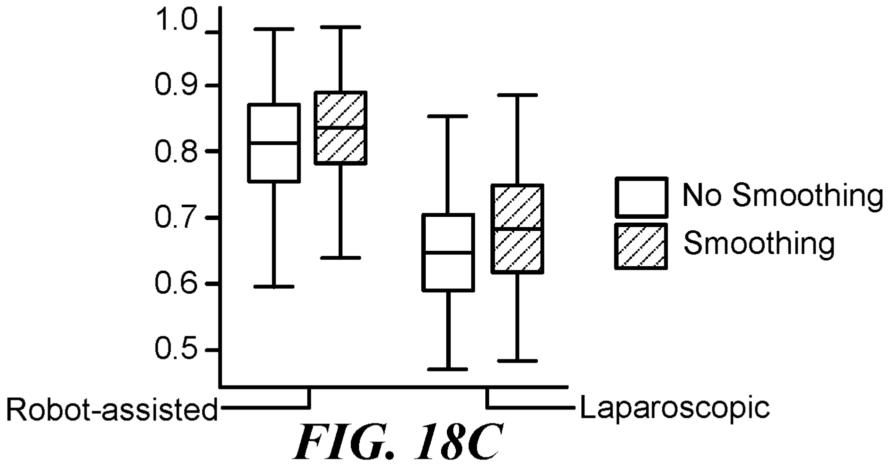
FIG. 18A is table depicting classification performance results for an example implementation trained upon robotic/non-robotic data and applied for inference upon non-robotic/robotic data.
FIG. 18B is table depicting cross-surgery classification performance using an example implementation trained upon data acquired from a robotic surgical theater and applied for inference to data acquired from a non-robotic surgical theater, and vice versa.
FIG. 18C is a plot comparing classification performance F1 scores with and without applying an implementation of smoothing as described herein.

Specifically, FIG. 18A is a table of the averaged cross-validated results comparing different features for frame-level and session-level recognition over the DaVinci16 (the "Robot" rows) and Cholec80 videos (the "Laparo." rows). The table of FIG. 18A's cross-surgery results (i.e., models trained on DaVinci16 and applied to Cholec80 or vice versa) suggest that knowledge of endoscopic image features (e.g., color) may also be sufficiently robust to generalize to different surgical types. Accordingly, models of various embodiments may translate to various surgical environments given their scalability and performance. Thus, once trained, the models may be used generally by clinical and technical communities to scrub endoscopic videos from minimally invasive surgery. As shown in FIG. 18A, the example implementation with only the random forest model was able to detect and remove endoscopic out-of-body frames with the highest recall of 96.27% in robotic-assisted surgeries and 92.71% in laparoscopic surgeries.

To further demonstrate cross-domain compatibility, FIG. 18B is table depicting cross-surgery classification performance using the example implementation. To evaluate the performance of models for recognizing each endoscopic frame, the average precision, average recall, and average F1 score of the endoscopic frame classes were considered. Here, precision is calculated as the ratio between the true positives and the number of total positive predictions, recall is the ratio between the true positives and the number of actual positives, and the F1-score is calculated as a weighted average of the precision and recall as an overall measure of accuracy.

As indicated, in this particular context, VGG16 features achieved the best performance with an average F1 score of 0.75 and an average recall of 75:53% when transferring models trained on upon robotic-assisted surgery to laparoscopic surgery. Conversely, when transferring laparoscopic surgery to robotic-assisted surgery, the color features provides the highest F1 score of 0.93 and recall of 96:01%. This implies that VGG16 and color visual features may be useful for knowledge transfer under varying types of surgery. De-tuning deep learning models upon the clinical data under consideration before extracting features may improve the deep learning models' performance. Similarly, more data collection may potentially lead to more robust models.

From such results, one may decide to select embodiments employing optimal selections of features and intermediate models. For example, where the data is similar to that considered here, one may implement a system having only a random forest intermediate model and SVM, each receiving a concatenated feature vector of Color and VGG feature vectors. One will appreciate that given other datasets, different features and models may be selected. For example, models may receive only feature vectors for which they performed well and feature vectors may only be generated which, when consumed by the appropriate corresponding models, produce desirable classification rates.

FIG. 18C is a plot illustrating a quantitative comparisons of classification performance with the random forest of FIGS. 18A and 18B measured with the F1 score with and without smoothing. For simplicity of discussion, the presented results are averaged across all features in each surgical dataset. Compared to the predictions without post-processing, temporal post-processing led to a better performance, improving F1 scores by 2.66% on average over the DaVinci16 data, and 5.07% on average over the Cholec80 data.

Computer System

Figure 19:
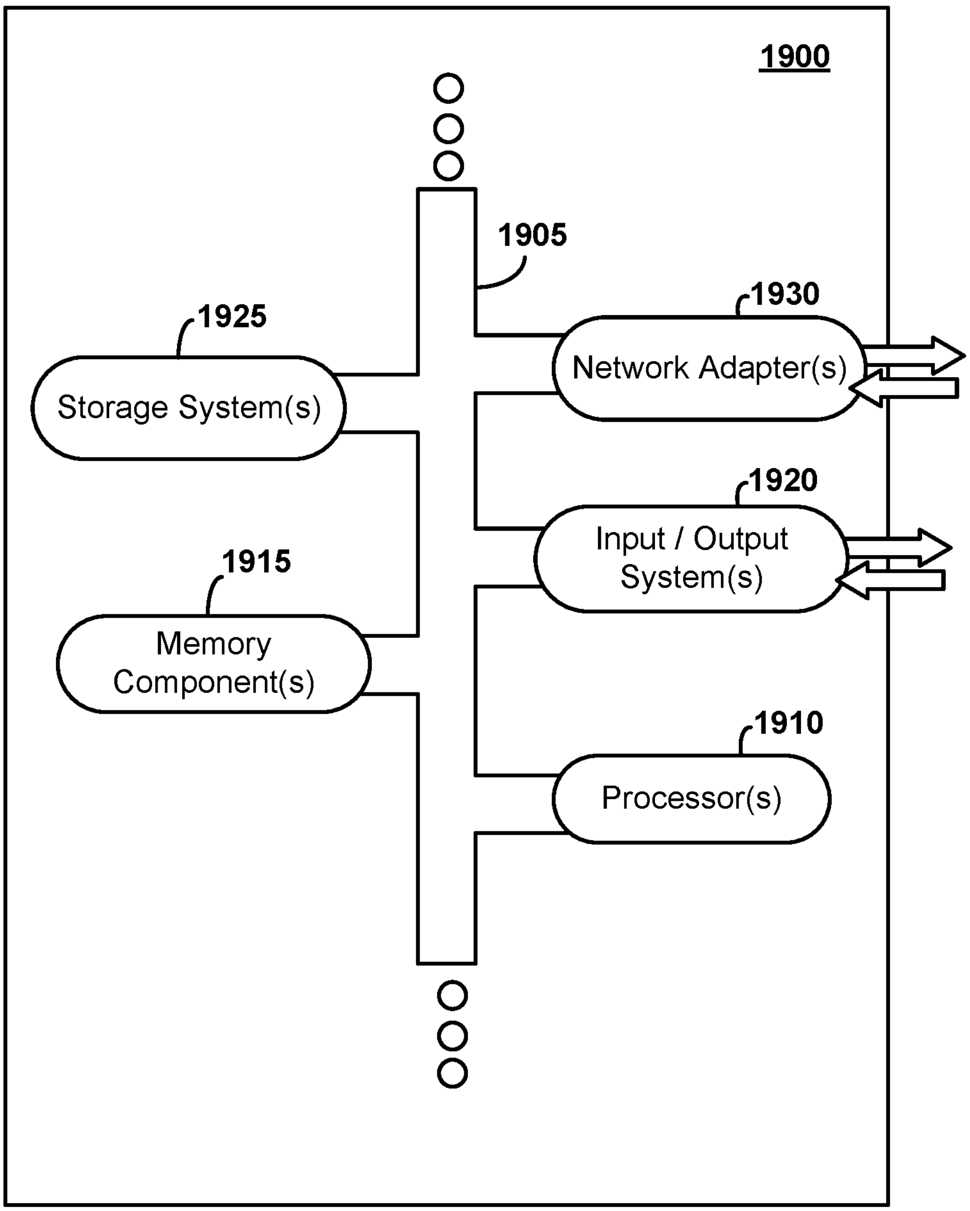
FIG. 19 is a block diagram of an example computer system as may be used in conjunction with some of the embodiments.

FIG. 19 is a block diagram of an example computer system as may be used in conjunction with some of the embodiments. The computing system 1900 may include an interconnect 1905, connecting several components, such as, e.g., one or more processors 1910, one or more memory components 1915, one or more input/output systems 1920, one or more storage systems 1925, one or more network adaptors 1930, etc. The interconnect 1905 may be, e.g., one or more bridges, traces, busses (e.g., an ISA, SCSI, PCI, I2C, Firewire bus, etc.), wires, adapters, or controllers.

The one or more processors 1910 may include, e.g., an Intel™ processor chip, a math coprocessor, a graphics processor, etc. The one or more memory components 1915 may include, e.g., a volatile memory (RAM, SRAM, DRAM, etc.), a non-volatile memory (EPROM, ROM, Flash memory, etc.), or similar devices. The one or more input/output devices 1920 may include, e.g., display devices, keyboards, pointing devices, touchscreen devices, etc. The one or more storage devices 1925 may include, e.g., cloud-based storages, removable USB storage, disk drives, etc. In some systems memory components 1915 and storage devices 1925 may be the same components. Network adapters 1930 may include, e.g., wired network interfaces, wireless interfaces, Bluetooth™ adapters, line-of-sight interfaces, etc.

One will recognize that only some of the components, alternative components, or additional components than those depicted in FIG. 19 may be present in some embodiments.

Similarly, the components may be combined or serve dual-purposes in some systems. The components may be implemented using special-purpose hardwired circuitry such as, for example, one or more ASICs, PLDs, FPGAs, etc. Thus, some embodiments may be implemented in, for example, programmable circuitry (e.g., one or more microprocessors) programmed with software and/or firmware, or entirely in special-purpose hardwired (non-programmable) circuitry, or in a combination of such forms.

In some embodiments, data structures and message structures may be stored or transmitted via a data transmission medium, e.g., a signal on a communications link, via the network adapters 1930. Transmission may occur across a variety of mediums, e.g., the Internet, a local area network, a wide area network, or a point-to-point dial-up connection, etc. Thus, "computer readable media" can include computer-readable storage media (e.g., "non-transitory" computer-readable media) and computer-readable transmission media.

The one or more memory components 1915 and one or more storage devices 1925 may be computer-readable storage media. In some embodiments, the one or more memory components 1915 or one or more storage devices 1925 may store instructions, which may perform or cause to be performed various of the operations discussed herein. In some embodiments, the instructions stored in memory 1915 can be implemented as software and/or firmware. These instructions may be used to perform operations on the one or more processors 1910 to carry out processes described herein. In some embodiments, such instructions may be provided to the one or more processors 1910 by downloading the instructions from another system, e.g., via network adapter 1930.

Remarks

The drawings and description herein are illustrative. Consequently, neither the description nor the drawings should be construed so as to limit the disclosure. For example, titles or subtitles have been provided simply for the reader's convenience and to facilitate understanding. Thus, the titles or subtitles should not be construed so as to limit the scope of the disclosure, e.g., by grouping features which were presented in a particular order or together simply to facilitate understanding. Unless otherwise defined herein, all technical and scientific terms used herein have the same meaning as commonly understood by one of ordinary skill in the art to which this disclosure pertains. In the case of conflict, this document, including any definitions provided herein, will control. A recital of one or more synonyms herein does not exclude the use of other synonyms. The use of examples anywhere in this specification including examples of any term discussed herein is illustrative only, and is not intended to further limit the scope and meaning of the disclosure or of any exemplified term.

Similarly, despite the particular presentation in the figures herein, one skilled in the art will appreciate that actual data structures used to store information may differ from what is shown. For example, the data structures may be organized in a different manner, may contain more or less information than shown, may be compressed and/or encrypted, etc. The drawings and disclosure may omit common or well-known details in order to avoid confusion. Similarly, the figures may depict a particular series of operations to facilitate understanding, which are simply exemplary of a wider class of such collection of operations. Accordingly, one will readily recognize that additional, alternative, or fewer operations may often be used to achieve the same purpose or effect depicted in some of the flow diagrams. For example, data may be encrypted, though not presented as such in the figures, items may be considered in different looping patterns ("for" loop, "while" loop, etc.), or sorted in a different manner, to achieve the same or similar effect, etc.

Reference herein to "an embodiment" or "one embodiment" means that at least one embodiment of the disclosure includes a particular feature, structure, or characteristic described in connection with the embodiment. Thus, the phrase "in one embodiment" in various places herein is not necessarily referring to the same embodiment in each of those various places. Separate or alternative embodiments may not be mutually exclusive of other embodiments. One will recognize that various modifications may be made without deviating from the scope of the embodiments.

We claim:

1. A computer-implemented method for classifying a plurality of video frames as depicting a region inside or outside a patient's body, the method comprising:

acquiring a plurality of features associated with the plurality of video frames;

identifying a feature from the plurality of features for each of a classifier of a plurality of different classifiers, each classifier configured to classify a different feature than other classifiers of the plurality of different classifier;

generating a classification of each feature of the plurality of features using a respective classifier of the plurality of different classifiers;

providing the classification of each feature to a fusion model configured to output at least one classification prediction;

classifying, by the fusion model, at least one video frame of the plurality of video frames as depicting a region inside or outside the patient's body based upon the at least one classification prediction;

determining one or more intervals of consecutive classifications of the plurality of video frames depicting the region outside the patient's body; and in response to determining that a duration of the one or more intervals is greater than a threshold indicative of an inter-surgery period, excising the one or more intervals corresponding to the region outside the patient's body.

2. The computer-implemented method of claim 1, wherein, the at least one classification prediction comprises:

a first classification prediction by a first model implementation; and a second classification prediction by a second model implementation.

3. The computer-implemented method of claim 2, wherein, the plurality of features comprises:

at least one of color histogram features, blob features, image texture features, and image moment features; and features generated from a neural network, wherein, the first model implementation is configured to receive the at least one of color histogram features, blob features, image texture features, and image moment features, and wherein, the second model implementation is configured to receive the features generated from the neural network.

4. The computer-implemented method of claim 2, wherein classifying the video frame as depicting a region inside or outside the patient's body based upon the at least one classification prediction, comprises:

providing the first classification prediction and the second classification to a fusion model implementation.

5. The computer-implemented method of claim 2, wherein classifying the video frame as depicting a region inside or outside the patient's body based upon the at least one classification prediction, comprises:

providing the first classification prediction and the second classification to fusion logic.

6. The computer-implemented method of claim 1, wherein, classifying the video frame as depicting a region inside or outside the patient's body based upon the at least one classification prediction comprises applying a windowing filter to a plurality of video frame classification results.

7. The computer-implemented method of claim 1, the method further comprising:

generating an uncertainty prediction associated with the classification of the video frame as depicting a region inside or outside the patient's body, at least in part, by determining a plurality of entropies associated with the plurality of classification predictions.

8. The computer-implemented method of claim 1, wherein the threshold is a first threshold and the one or more intervals are one or more first intervals, the computer-implemented method further comprising:

determining one or more second intervals of consecutive classifications of the plurality video frames as depicting a region inside the patient's body;

in response to determining that the duration of the one or more second intervals is less than a second threshold indicative of a minimum surgery duration, excising the one or more intervals corresponding to the region inside the patient's body.

9. A non-transitory computer-readable medium comprising instructions configured to cause a computer system to perform a method, the method comprising:

acquiring a plurality of features associated with a plurality of video frames;

identifying a feature from the plurality of features for each of a classifier of a plurality of different classifiers, each classifier configured to classify a different feature than other classifiers of the plurality of different classifier;

generating a classification of each feature of the plurality of features using a respective classifier of the plurality of different classifiers;

providing the classification of each feature to a fusion model configured to output at least one classification prediction;

classifying, by the fusion model, at least one video frame of the plurality of video frames as depicting a region inside or outside a patient's body based upon the at least one classification prediction;

determining one or more intervals of consecutive classifications of the plurality of video frames depicting the region outside the patient's body; and in response to determining that a duration of the one or more intervals is greater than a threshold indicative of an inter-surgery period, excising the one or more intervals corresponding to the region outside the patient's body.

10. The non-transitory computer-readable medium of claim 9, wherein, the at least one classification prediction comprises:

a first classification prediction by a first model implementation; and a second classification prediction by a second model implementation.

11. The non-transitory computer-readable medium of claim 10, wherein, the plurality of features comprises:

at least one of color histogram features, blob features, image texture features, and image moment features; and features generated from a neural network, wherein, the first model implementation is configured to receive the at least one of color histogram features, blob features, image texture features, and image moment features, and wherein, the second model implementation is configured to receive the features generated from the neural network.

12. The non-transitory computer-readable medium of claim 10, wherein classifying the video frame as depicting a region inside or outside the patient's body based upon the at least one classification prediction, comprises:

providing the first classification prediction and the second classification to a fusion model implementation.

13. The non-transitory computer-readable medium of claim 10, wherein classifying the video frame as depicting a region inside or outside the patient's body based upon the at least one classification prediction, comprises:

providing the first classification prediction and the second classification to fusion logic.

14. The non-transitory computer-readable medium of claim 9, wherein, classifying the video frame as depicting a region inside or outside the patient's body based upon the at least one classification prediction comprises applying a windowing filter to a plurality of video frame classification results.

15. The non-transitory computer-readable medium of claim 9, the method further comprising:

generating an uncertainty prediction associated with the classification of the video frame as depicting a region inside or outside the patient's body, at least in part, by determining a plurality of entropies associated with the plurality of classification predictions.

16. The non-transitory computer-readable medium of claim 9, wherein the threshold is a first threshold and the one or more intervals are one or more first intervals, the method further comprising:

determining one or more second intervals of consecutive classifications of the plurality video frames as depicting a region inside the patient's body;

in response to determining that the duration of the one or more second intervals is less than a second threshold indicative of a minimum surgery duration, excising the one or more intervals corresponding to the region inside the patient's body.

17. A computer system comprising:

at least on processor; and at least one memory comprising instructions configured to cause the computer system to perform a method, the method comprising:

acquiring a plurality of features associated with a plurality of video frames;

identifying a feature from the plurality of features for each of a classifier of a plurality of different classifiers, each classifier configured to classify a different feature than other classifiers of the plurality of different classifier;

generating a classification of each feature of the plurality of features using a respective classifier of the plurality of different classifiers;

providing the classification of each feature to a fusion model configured to output at least one classification prediction;

classifying, by the fusion model, at least one video frame of the plurality of video frames as depicting a region inside or outside a patient's body based upon the at least one classification prediction;

determining one or more intervals of consecutive classifications of the plurality of video frames depicting the region outside the patient's body; and in response to determining that a duration of the one or more intervals is greater than a threshold indicative of an inter-surgery period, excising the one or more intervals corresponding to the region outside the patient's body.

18. The computer system of claim 17, wherein, the at least one classification prediction comprises:

a first classification prediction by a first model implementation; and a second classification prediction by a second model implementation.

19. The computer system of claim 18, wherein, the plurality of features comprises:

at least one of color histogram features, blob features, image texture features, and image moment features; and features generated from a neural network, wherein, the first model implementation is configured to receive the at least one of color histogram features, blob features, image texture features, and image moment features, and wherein, the second model implementation is configured to receive the features generated from the neural network.

20. The computer system of claim 18, wherein classifying the video frame as depicting a region inside or outside the patient's body based upon the at least one classification prediction, comprises:

providing the first classification prediction and the second classification to a fusion model implementation.

21. The computer system of claim 18, wherein classifying the video frame as depicting a region inside or outside the patient's body based upon the at least one classification prediction, comprises:

providing the first classification prediction and the second classification to fusion logic.

22. The computer system of claim 17, wherein, classifying the video frame as depicting a region inside or outside the patient's body based upon the at least one classification prediction comprises applying a windowing filter to a plurality of video frame classification results.

23. The computer system of claim 17, wherein the threshold is a first threshold and the one or more intervals are one or more first intervals, the method further comprising:

determining one or more second intervals of consecutive classifications of the plurality video frames as depicting a region inside the patient's body;

in response to determining that the duration of the one or more second intervals is less than a second threshold indicative of a minimum surgery duration, excising the one or more intervals corresponding to the region inside the patient's body.

* * * * *